(12) United States Patent
Li et al.

(10) Patent No.: US 7,053,234 B2
(45) Date of Patent: May 30, 2006

(54) ANTIBACTERIAL AGENTS

(75) Inventors: Leping Li, Burlingame, CA (US);
Xiaoqi Chen, San Mateo, CA (US);
Pingchen Fan, Newark, CA (US);
Jeffrey Thomas Mihalic, San Francisco, CA (US); Serena Cutler, Palo Alto, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 10/877,408

(22) Filed: Jun. 25, 2004

(65) Prior Publication Data

US 2004/0235911 A1    Nov. 25, 2004

Related U.S. Application Data

(63) Continuation of application No. 09/759,633, filed on Jan. 12, 2001, now Pat. No. 6,780,858.

(60) Provisional application No. 60/175,892, filed on Jan. 13, 2000.

(51) Int. Cl.
*C07C 275/28* (2006.01)
(52) U.S. Cl. .......................................................... 558/8
(58) Field of Classification Search ..................... 558/8
See application file for complete search history.

(56) References Cited

U.S. PATENT DOCUMENTS 3,347,874 A    10/1967    Eloy et al.
4,243,409 A    1/1981    Schmidt et al.

FOREIGN PATENT DOCUMENTS

JP    01013071 A2 *    1/1987
JP    02161430 A2 *    6/1990
JP    02201358 A2 *    8/1990

OTHER PUBLICATIONS

Gilchrist et al., J. Chem. Soc. Perk. Trans. 1: Org. Bio-org Chem. (1972-1999) (1976), vol. 20, pp. 2166-2170.*
Dondoni et al., J. Chem. Soc. Perk. Trans. 2: Phy. Org. Chem. (1972-1999) (1976), vol. 9, pp. 1036-1040.*
Agirbas, Hikmet et al., A convenient synthesis of 3,4-disubstituted-1,2,4-thiadiazole-5(4H)-thiones XP002167479 (abstract) and Phosphorus, Sulfur silicon Relat. Elem. (1998).
Agirbas, Hikmet et al., Reation of substituted benzamide oximes with chloroacetyl chloride and thiophosgene, XP002167480 (abstract) and Phosphorus, Sulfur Silicon Relat. Elm. (1999).
August, Bernd et al., ESR spectroscopic detection of benzoxadiazinyl radicals, Tetrahedron Let. (1979), XP002167474.
Aurich, Hans G. et al., Aminyl oxides (nitroxides). XX. Formation of aminyl oxides in the reaction of nitrile oxides with hydroxylamines, Chem. Ber. (1975) XP002167476.
Beltrame, Paolo et al., Kinetics of the acid-catalyzed addition of arylamines to aromatic nitrile oxides XP002167482 (abstract and Gazz. Chim. Ital. (1984)).
Freccero, Mauro et al., Cycloadditions with trophane and its derivatives. 7. Reactions of o,o'-disubstituted benzonitrile oxides with 8-azaheptafulvenes Heterocycles (1998), XP002167473.
Gilchrist, Thomas et al., Reversible cyclization of orgho-blocked N-arylnitroso imines, J. Chem. Soc., Chem. Commun. (1975) XP002167475.
Micromastoras, E.D. et al., Electron-impact induced fragmentatin of benzamidoximes XP002167483 (abstract) and Chem. Chron. (1974).
Oyama, Hiroshi et al., Electrochemical manufacture of benzenecarboxyimidamide derivative. XP002167477 (abstract) and JP 01215994 A (Aug. 29, 1989).
Oyama, Hiroshi et al., Preparation of O-(acylalkyl) benzanilideoximes as agrochemial fungicides XP002167481 (abstract) and JP 01 034954 A (Feb. 6, 1989).
Oyama, Hiroshi et al., Preparaton of 1,2,4-oxadiazin-5-ones as agrochemical microbicides. XP002167478 (abstract) and JP 03 148267 A (Jun. 25, 1991).
Yousif, N.M. et al., Reactions of alpha.,. bea. - spiroepoxyalkanones. Part IV. New and facile synthesis of tetrahydronaphthalen-2ol derivatives for biological evalutioan, Bul. Fac. Pharm. XP-001002117 (abstract) (1998).

(Continued)

*Primary Examiner*—Taofiq Solola
(74) *Attorney, Agent, or Firm*—Banner & Witcoff,Ltd.

(57) ABSTRACT

Hydroxyamidines and related compounds are provided which are suitable as antibacterial agents.

5 Claims, No Drawings

OTHER PUBLICATIONS

Chemical abstract XP002167487, CAS RN: 288246-41-3.
Chemical abstracts XP002167485, CAS RN: 288246-45-7.
Chemical abstracts XP002167486, CAS RN: 288246-40-2.
Chemical abstracts XP002167488, CAS RN: 96633-78-2.
Chemical abstracts XP002167484, CAS RN: 299202-70-3.
Ristano F. et al., 5-exo- Trigonal Cycization and [3,5] Rearrangement of N-Ary Benzamidoximes by Reaction with Nitrile Oxides, TETRAHEDRON, vol. 53, No. 3, pp. 1098-1098 (1997).

* cited by examiner

ANTIBACTERIAL AGENTS

CROSS REFERENCE TO RELATED APPLICATIONS

This application is a continuation of U.S. patent application Ser. No. 09/759,633, filed Jan. 12, 2001, now U.S. Pat. No. 6,780,858 which claims priority to U.S. patent application Ser. No. 60/175,892, filed Jan. 13, 2000. The disclosures of each of the above are incorporated herein by reference.

STATEMENT AS TO RIGHTS TO INVENTIONS MADE UNDER FEDERALLY SPONSORED RESEARCH AND DEVELOPMENT

Not applicable

BACKGROUND OF THE INVENTION

Resistance to currently available antibiotics has created a need for new antibiotic agents. Infections, caused by organisms such as *Staphylococcus aureus, Pseudomonas aeruginosa, Enterococcus faecium* and *Enterococcus faecalis*, have become increasingly resistant to currently approved antibiotics. For example, significant clinical problems include methicillin-resistant strains of *S. aureus*, which are resistant to all current antibiotics except vancomycin (a drug of last resort because of severe side effects), and a vancomycin-resistant strain of *E. faecium enterococci* which is now found world-wide. Even community-acquired organisms such as *Streptococcus pneumoniae* are increasingly resistant to antimicrobial agents, with a significant number of isolates being resistant to penicillin and extended-spectrum cephalosporins.

The emergence and spread of resistant bacterial organisms are primarily caused by acquisition of drug resistance genes, resulting in a broad spectrum of antibiotic resistance (e.g., extended-spectrum cephalosporin-resistant mutant .beta.-lactamases found in several bacterial organisms). Genetic exchange of multiple-resistance genes, by transformation, transduction and conjugation; combined with selective pressures in settings such as hospitals where there is heavy use of antibiotic therapies, enhance the survival and proliferation of antimicrobial agent-resistant bacterial strains occurring by, e.g., spontaneous mutants. Although the extent to which bacteria develop resistance to antimicrobial drugs and the speed with which they do so vary with different types of drugs, resistance has inevitably developed to all antimicrobial agents (see Gold and Moellering, Jr., 1996, New Eng. J. Med., 335(19):1445–1453).

To prevent or delay the buildup of a resistant pathogen population, different chemicals that are effective against a particular disease-causing bacterium must be available. Thus, there is a need to identify compounds which can penetrate and specifically kill the pathogenic bacterial cell, or arrest its growth without also adversely affecting its human, animal, or plant host.

One avenue for accomplishing this task involves the use of compounds targeting RNA polymerase. Accordingly, what is needed in the art are new compounds which are effective inhibitors of bacterial RNA polymerase and which are useful as antibacterial agents. The present invention provides such compounds along with methods for their use.

SUMMARY OF THE INVENTION

In one aspect, the present invention provides antibacterial compounds having the formula:

A-X-M-Y-B or a pharmaceutically acceptable salt thereof, wherein the letters A and B each independently represent a substituted or unsubstituted aryl group or a substituted or unsubstituted heteroaryl group. The letters X and Y each independently represent a group selected from:

a bond,

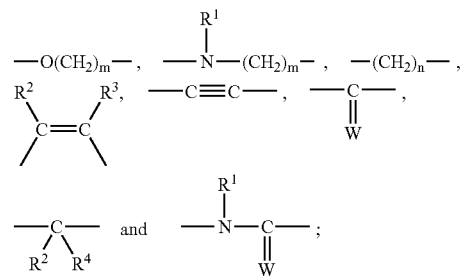

with the proviso that at least one of X or Y is a bond. In the above group of radicals, the subscript m is 0, 1 or 2; the subscript n is 1 or 2; W is selected from O, N—OR$^5$, N—NR$^1$R$^2$, N—NR$^1$C(O)R$^6$ and N—OC(O)R$^6$; wherein R$^1$, R$^2$, R$^3$, and R$^5$ each independently represent H, (C$_1$–C$_6$) alkyl, aryl, aryl(C$_1$–C$_6$)alkyl, heteroaryl or heteroaryl (C$_1$–C$_6$)alkyl; R$^4$ represents H, OH, (C$_1$–C$_6$)alkyl, (C$_1$–C$_6$) alkoxy, amino, (C$_1$–C$_6$)alkylamino, di(C$_1$–C$_6$)alkylamino, (C$_1$–C$_6$)acylamino, or (C$_1$–C$_8$)heteroalkyl; and R$^6$ represents H, (C$_1$–C$_6$)alkyl, (C$_1$–C$_6$)alkoxy, amino, (C$_1$–C$_6$)alkylamino, di(C$_1$–C$_6$)alkylamino, or (C$_1$–C$_8$)heteroalkyl. Returning to formula I, the letter M is a divalent linking group selected from:

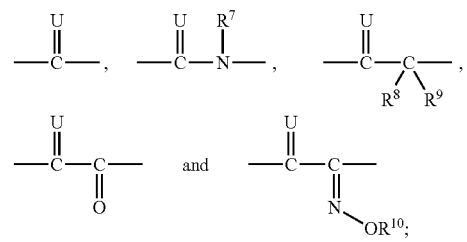

wherein the letter U represents a group selected from:

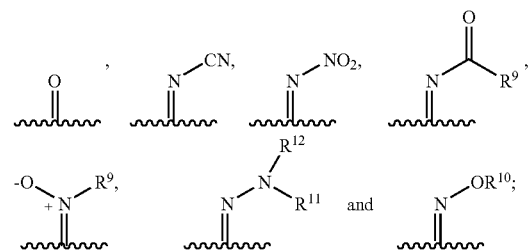

wherein $R^7$ and $R^8$ are independently H, OH, $(C_1-C_6)$alkyl, $(C_1-C_6)$alkoxy, amino, $(C_1-C_6)$alkylamino or di$(C_1-C_6)$alkylamino; $R^9$ is H, $(C_1-C_6)$alkyl, aryl, aryl$(C_1-C_6)$alkyl, heteroaryl or heteroaryl$(C_1-C_6)$alkyl; $R^{10}$ is H, $(C_1-C_6)$alkyl, aryl$(C_1-C_6)$alkyl or heteroaryl$(C_1-C_6)$alkyl; and $R^{11}$ and $R^{12}$ are independently H, $(C_1-C_6)$alkyl, aryl$(C_1-C_6)$alkyl, heteroaryl$(C_1-C_6)$alkyl, C(O)$R^{14}$, C(O)O$R^{14}$, C(O)—N$R^{14}R^{15}$, S(O)$_2R^{13}$ or S(O)$_2$N$R^{14}R^{15}$; wherein $R^{13}$ is $(C_1-C_6)$alkyl, $(C_1-C_6)$heteroalkyl, phenyl or substituted phenyl; and $R^{14}$ and $R^{15}$ are each independently H, $(C_1-C_6)$alkyl or $(C_1-C_6)$heteroalkyl.

In another aspect, the present invention provides pharmaceutical compositions comprising one or more of the above compounds in admixture with a pharmaceutically acceptable excipient.

In yet another aspect, the present invention provides methods for controlling bacterial growth on a surface comprising contacting the surface with a compound having the formula above.

In still another aspect, the present invention provides methods for treating or preventing bacterial growth in a subject by administering to the subject an effective amount of a compound having the formula above.

BRIEF DESCRIPTION OF THE DRAWINGS

Not applicable

DESCRIPTION OF THE INVENTION

Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)$_m$ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —CH$_2$CH$_2$CH$_2$CH$_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quatemized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)$_3$, —CH$_2$—CH$_3$, —CH$_2$—CH$_2$—S(O)$_2$—CH$_3$, —CH=CH—O—CH$_3$, —Si(CH$_3$)$_3$, CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —CH$_2$—CH$_2$—S—CH$_2$CH$_2$— and —CH$_2$—S—H$_2$—CH$_2$—NH—CH$_2$—. For heteroalkylene groups, heteroatoms can also occupy either or both of the chain termini. Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and 5, wherein the nitrogen and sulfur atoms are optionally oxidized, and the nitrogen atom(s) are optionally quatemized. The aryl groups that contain heteroatoms may be referred to as "heteroaryl" and can be attached to the remainder of the molecule through a heteroatom Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —NR', =O, =NR', =N—NR', —NR'R'', —SR', -halogen, —SiR'R''R''', —OC(O)R', —C(O)R', —CO$_2$R', CONR'R'', —OC(O)NR'R'', —NR''C(O)R', —NR'—C(O)NR''R''', —NR''C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R'', —CN and —CN and —NO$_2$ in a number ranging from zero to (2N+1), where N is the total number of carbon atoms in such radical. R', R' and R''' each independently refer to hydrogen, unsubstituted($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R'' are attached to the same nitrogen atom, they can be combined with the nitrogen atom to form a 5-, 6-, or 7-membered ring. For example, —NR'R'' is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the alkyl groups will have from 0–3 substituents, more preferably 0, 1, or 2 substituents, unless otherwise specified.

Similarly, substituents for the aryl and heteroaryl groups are varied and are selected from: -halogen, —NR', —OC(O)R', —NR'R'', —SR', —R', —CN, —NO$_2$, —CO$_2$R', —CONR'R'', —C(O)R', —OC(O)NR'R'', —NR''C(O)R', —NR''C(O)$_2$R', —NR'—C(O)NR''R''', —NH—C(NH$_2$)=NH, —NR'C(NH$_2$)=NH, —NH—C(NH$_2$)=NR', —S(O)R', —S(O)$_2$R', —S(O)$_2$NR'R'', —N$_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R', R'' and R''' are independently selected from hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl.

Two of the substituents on adjacent atoms of the aryl or heteroaryl ring may optionally be replaced with a substituent of the formula -T-C(O)—(CH$_2$)$_q$-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$-B-, wherein A and B are independently —CH$_2$—, —O—, —NH—, —S—, —S(O)—, —S(O)$_2$—, —S(O)$_2$ NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Description of the Embodiments

In one aspect, the present invention provides antibacterial compounds having the formula:

A-X-M-Y-B     (I)

or a pharmaceutically acceptable salt thereof, wherein the letters A and B each independently represent a substituted or unsubstituted aryl group or a substituted or unsubstituted heteroaryl group. The letters X and Y each independently represent a group selected from:
a bond,

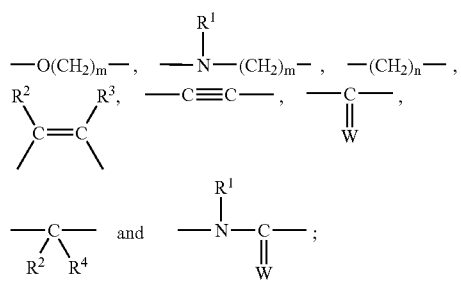

with the proviso that at least one of X or Y is a bond. In the above group of radicals, the subscript m is 0, 1 or 2; subscript n is 1 or 2; W is selected from O, N—OR$^5$, N—NR$^1$R$^2$, N—NR$^1$C(O)R$^6$ and N—OC(O)R$^6$; wherein R$^1$, R$^2$, R$^3$, and R$^5$ each independently represent H, (C$_1$–C$_6$) alkyl, aryl, aryl(C$_1$–C$_6$)alkyl, heteroaryl or heteroaryl (C$_1$–C$_6$)alkyl; R$^4$ represents H, OH, (C$_1$–C$_6$)alkyl, (C$_1$–C$_6$) alkoxy, amino, (C$_1$–C$_6$)alkylamino, di(C$_1$–C$_6$)alkylamino, (C$_1$–C$_6$)acylamino, or (C$_1$–C$_8$)heteroalkyl; and R$^6$ represents H, (C$_1$–C$_6$)alkyl, (C$_1$–C$_6$)alkoxy, amino, (C$_1$–C$_6$)alkylamino, di(C$_1$–C$_6$)alkylamino, or (C$_1$–C$_8$)heteroalkyl. Returning to formula I, the letter M is a divalent linking group selected from:

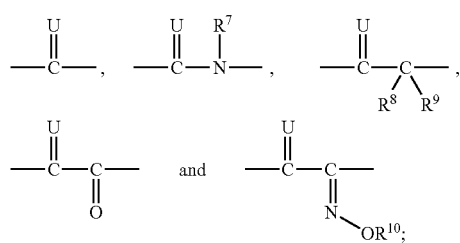

wherein the letter U represents a group selected from:

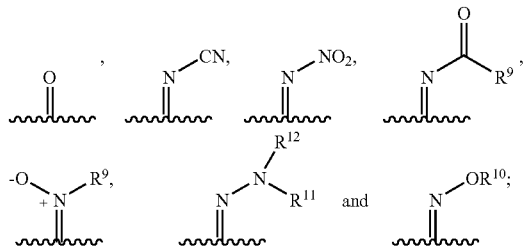

wherein R$^7$ and R$^8$ independently represent H, OH, (C$_1$–C$_6$) alkyl, (C$_1$–C$_6$)alkoxy, amino, (C$_1$–C$_6$)alkylamino or di(C$_1$–C$_6$)alkylamino; R$^9$ is H, (C$_1$–C$_6$)alkyl, aryl, aryl (C$_1$–C$_6$)alkyl, heteroaryl or heteroaryl(C$_1$–C$_6$)alkyl; R$^{10}$ is H, (C$_1$–C$_6$)alkyl, aryl(C$_1$–C$_6$)alkyl or heteroaryl(C$_1$–C$_6$) alkyl; and R$^{11}$ and R$^{12}$ are independently H, (C$_1$–C$_6$)alkyl, aryl(C$_1$–C$_6$)alkyl, heteroaryl(C$_1$–C$_6$)alkyl, C(O)R$^{14}$, C(O) OR$^{14}$, C(O)—NR$^{14}$R$^{15}$, S(O)$_2$R$^{13}$ or S(O)$_2$NR$^{14}$R$^{15}$; wherein R$^{13}$ is (C$_1$–C$_6$)alkyl, (C$_1$–C$_6$)heteroalkyl, phenyl or substituted phenyl; and R$^{14}$ and R$^{15}$ are each independently H, (C$_1$–C$_6$)alkyl or (C$_1$–C$_6$)heteroalkyl.

Within the groups provided above, the letters X and Y will preferably be independently selected from:
a bond,

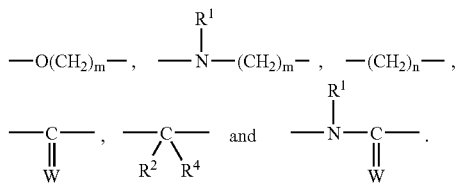

More preferably, X and Y will be selected from:
a bond,

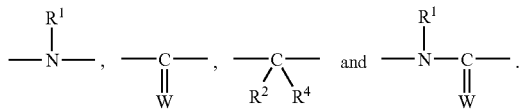

Still more preferably, X and Y are selected from:
a bond,

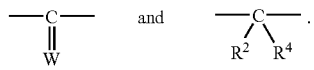

In the most preferred embodiments, X and Y each represent a bond.

In other preferred embodiments, the letter M represents

More preferably, M represents

wherein U represents a group selected from:

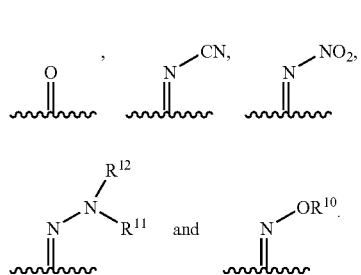

Still further preferred are those embodiments in which U represents a group selected from

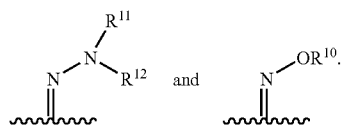

In a particularly preferred group of embodiments, the compound of formula I can be represented as formula II:

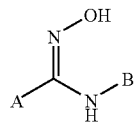

(II)

For the preferred compounds of formula (II), the letter A preferably represents a substituted or unsubstituted phenyl, substituted or unsubstituted naphthyl, substituted or unsubstituted quinolinyl, substituted or unsubstituted faranyl, substituted or unsubstituted thienyl, substituted or unsubstituted indolyl, substituted or unsubstituted benzimidazolyl, substituted or unsubstituted benzofuranyl, or substituted or unsubstituted benzothienyl. More preferably, A represents a substituted phenyl, substituted naphthyl, substituted quinolinyl, substituted furanyl, substituted thienyl, substituted indolyl, substituted benzimidazolyl, substituted benzofuranyl, or substituted benzothienyl. Still more preferably, the letter A represents a substituted phenyl having from one to three substituents selected from the group consisting of $(C_1-C_4)$ alkyl, $(C_1-C_4)$alkoxy, $(C_1-C_4)$haloalkyl, $(C_1-C_4)$haloalkoxy, halogen, phenyl, naphthyl, pyrrolyl, pyrazolyl and —$NR^{16}R^{17}$ wherein $R^{16}$ and $R^{17}$ are independently selected from the group consisting of hydrogen, $(C_1-C_8)$ alkyl and $(C_1-C_8)$heteroalkyl or are combined with the nitrogen atom to which each is attached to form a four-, five-, six- or seven-membered ring optionally having additional heteroatoms as ring members and optionally having additional substituents selected from the group consisting of $(C_1-C_8)$alkyl, $(C_1-C_8)$heteroalkyl and phenyl.

Still further preferred for compounds of formula II, are those in which the letter A represents a substituted phenyl group selected from:

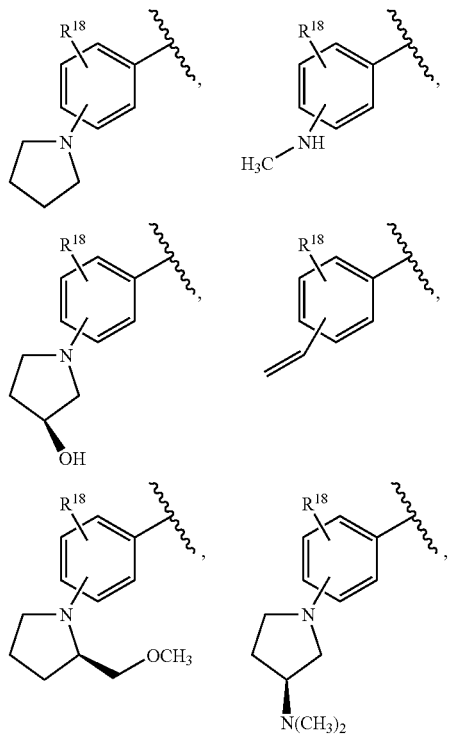

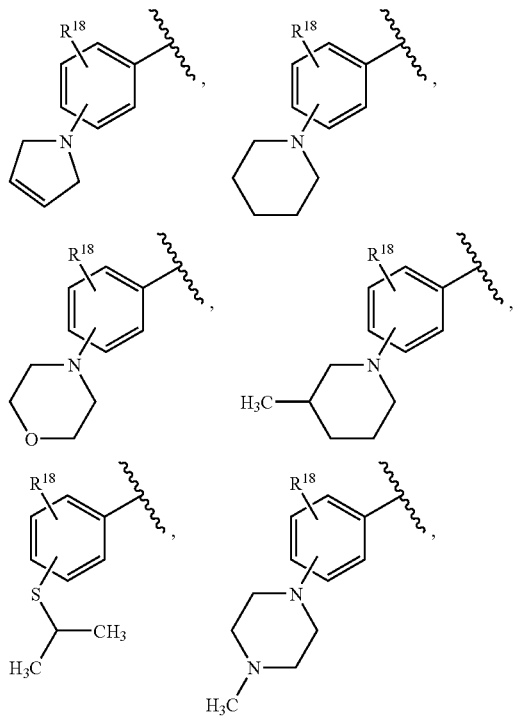

-continued

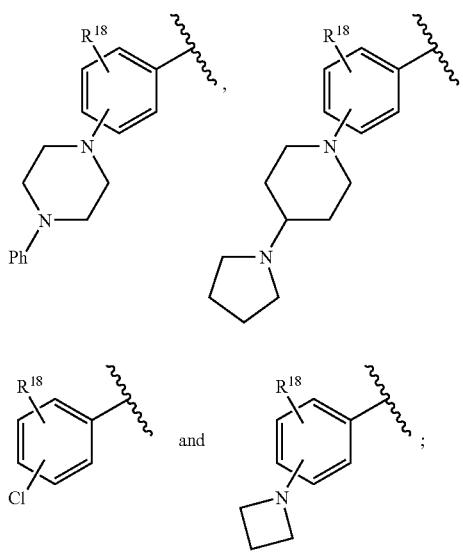

wherein $R^{18}$ represents $(C_1–C_4)$alkyl, $(C_1–C_4)$alkoxy, $(C_1–C_4)$heteroalkyl, $(C_1–C_4)$haloalkyl, $(C_1–C_4)$haloalkoxy and halogen.

Returning to formula II, the letter B is preferably a phenyl group substituted with from one to three substituents selected from the group consisting of $(C_1–C_4)$alkyl, $(C_1–C_4)$alkoxy, $(C_1–C_4)$heteroalkyl, $(C_1–C_4)$haloalkyl, $(C_1–C_4)$haloalkoxy, halogen, phenyl and phenoxy.

In a particularly preferred group of embodiments, the compounds are represented by formula II, wherein A is a phenyl group substituted with from one to three substituents selected from the group consisting of $(C_1–C_4)$alkyl, $(C_1–C_4)$alkoxy, $(C_1–C_4)$haloalkyl, $(C_1–C_4)$haloalkoxy, halogen and —$NR^{16}R^{17}$ wherein $R^{16}$ and $R^{17}$ are independently selected from the group consisting of hydrogen, $(C_1–C_8)$alkyl and $(C_1–C_8)$heteroalkyl or are combined with the nitrogen atom to which each is attached to form a four-, five-, six- or seven-membered ring optionally having additional heteroatoms as ring members and optionally having additional substituents selected from the group consisting of $(C_1–C_8)$alkyl, $(C_1–C_8)$heteroalkyl and phenyl, and B is a phenyl group substituted with from one to three substituents selected from the group consisting of $(C_1–C_4)$alkyl, $(C_1–C_4)$alkoxy, $(C_1–C_4)$heteroalkyl, $(C_1–C_4)$haloalkyl, $(C_1–C_4)$haloalkoxy, halogen, phenyl and phenoxy.

Synthesis of Hydroxyamidine and Related Derivatives

Compounds of the present invention can be prepared using readily available materials or known intermediates. The following schemes provide a variety of synthetic avenues for the production of the subject compounds. One of skill in the art will understand that additional methods are also useful. The groups Ar and Ar' are meant to indicate a substituted or unsubstituted aryl group or a substituted or unsubstituted heteroaryl group. Additionally, the groups provided as R, R' and R" are meant to indicate, in a very general sense, an alkyl or acyl radical (including substituted and heteroatom versions thereof). Scheme I illustrates the preparation of bisarylhydroxyamidine and related derivatives. An oxime I can be oxidized with a variety of halogenating agents, such as bleach, N-chlorosuccinimide (NCS), N-bromosuccinimide (NBS), to a halo oxime ii, Treatment of ii with a nucleophilic aryl amine, preferably in the presence of another tertiary amine base, such as triethylamine, in a polar solvent, such as dimethylformamide, provides iii. Alternatively, iii can be synthesized from an amide iv, Compound iv is converted to a more reactive intermediate v upon treatment with an activating reagent, such as phosphorous pentachloride, phosphoryl trichloride, triflic anhydride, or to vi upon treatment with phosphorous pentasulfide (or Lawesson's reagent). Reaction of the activated intermediate v or vi with hydroxyamine (or alkoxyamine) provides iii. Alternatively, reaction of v and vi with hydrazine or a substituted hydrazine leads to vii.

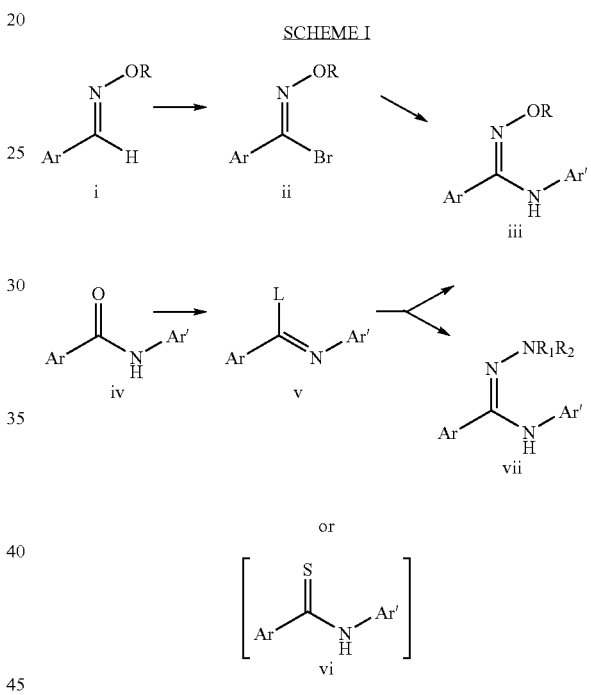

Scheme II outlines the preparation of various analogs bearing nonhydroxyamidine core structures. Starting from the readily accessible 1,3,5-trisubstituted benzenetrifluoride compound viii, the amino group selectively reacted with an arylisocyanate to produce the urea compound ix. The x group, which could be an amino, hydroxy, halo, or a carboxyl, was then functionalized in various ways to yield more elaborated analogs (such as xi and xii), as depicted in the synthetic scheme. Alternatively, by starting from a different and yet readily available starting material, such as structure xiii, the top part of the molecule was derivatized to introduce the desired substituents, such as an ether in structure xiv, leaving the lower half of the molecule for further structural manipulation. Specifically, the nitro group in xiv was reduced using $SnCl_2$ as the reducing agent or hydrogenation over Pd/C to the corresponding aniline xv. The aniline, in turn, was transformed in a variety of means, such as through acylation and alkylation to incorporate the aminoacetamide structure bearing the desired aryl groups.

SCHEME II

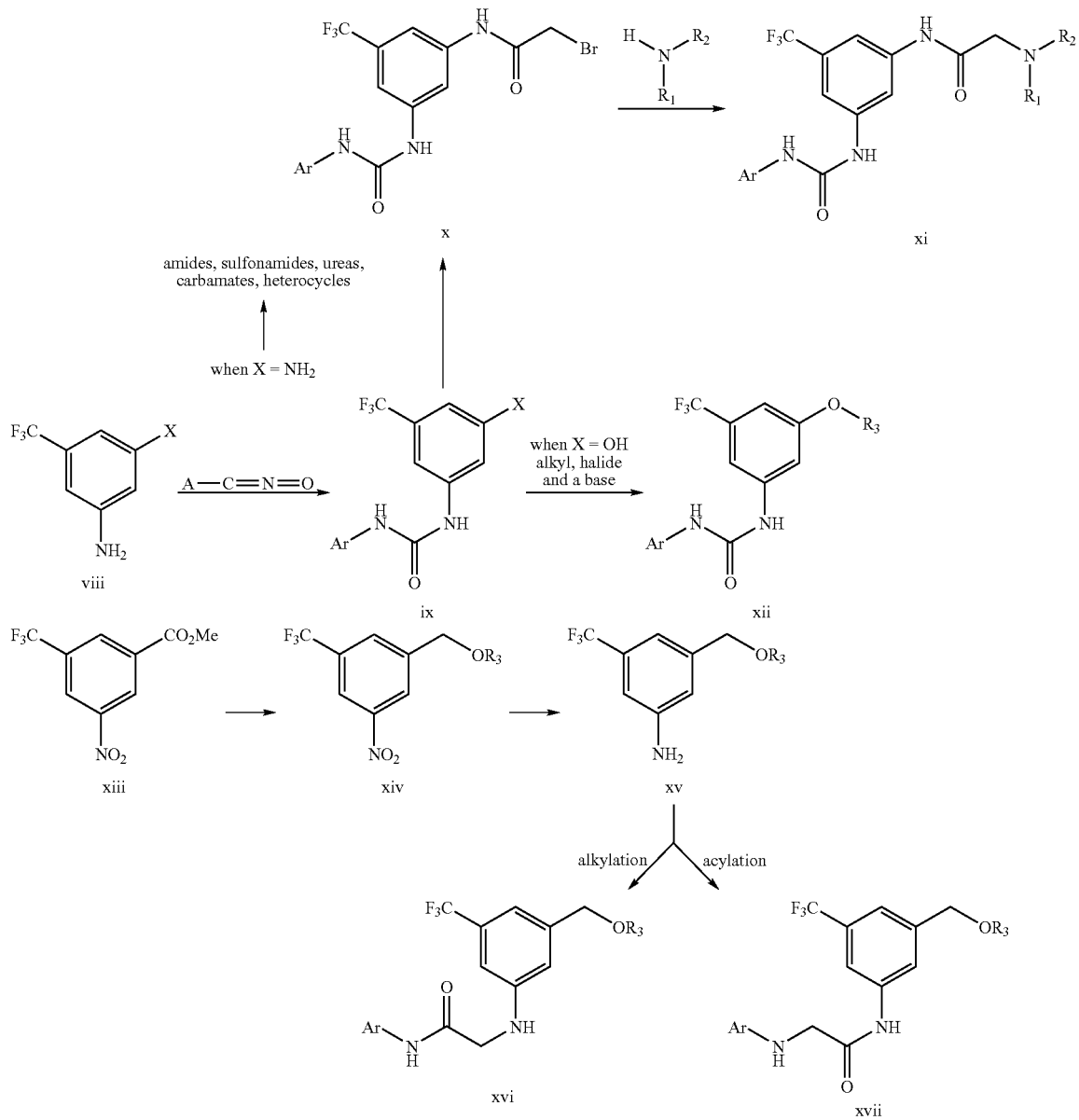

Evaluation of Compounds as Antibacterial Agents

The compounds of the present invention can be evaluated for antibacterial activity in a variety of assay formats known to those of skill in art. The specific assays used to select the most appropriate compound for use will typically depend on the targeted bacteria or infection. One common assay involves evaluation of the compounds as RNA polymerase inhibitors. In this assay, buffer (250 mM KCl, 5% Glycerol, 10 mM $MgCl_2$, 0.1 mg/ml BSA) is combined with 6 mM B-M.E., PT5 DNA template, and 1.3 ug/rxn $Sigma^{70}$ saturated E. coli RNA Polymerase (Epicenter). The compound is then added in a manner not to exceed 5% DMSO. Nucleotide triphosphates are then added at the following concentration: 250 uM ATP, CTP and UTP with 100 uM cold CTP and 50 uM alpha $^{32}P$ CTP. The mixture is incubated for 10 min at about 37° C. A [2×] loading buffer is added and the mixture is then run on a 6% urea denaturing PAGE until bromophenol blue reaches the edge of plate. The gel is soaked (about 20 minutes in 10% MeOH and 10% acetic acid, to remove urea), then dried (about 55 minutes at about 85° C. (BioRad Gel Drier)) and exposed to a Phospho Imaging Plate for 1 hour. The plate is then read on a Fujix Bas1000 Imaging System and quantified using MacBas v2.0 software. An IC50 (in uM) can be calculated as the concentration of a drug which reduces the enzyme activity to 50% of the control.

For MIC determinations for selected bacteria, log phase growing bacteria are re-suspended at $1\times10^5$ bacteria per mL in LB medium. The compound is added and two-fold dilutions are made. The final volume in the 96-well plate is about 100 uL. The plate is incubated at 37° C. in the dark with shaking. After 16 hours of incubation, growth is monitored by reading A600 or by visual inspection. MIC is defined as the minimum concentration of drug resulting in inhibition of visible growth of bacterial under the conditions described (above) in National Committee for Clinical Laboratory Standards 1993. Methods for dilution antimicrobial susceptibility tests for bacteria that grow aerobically. Approved standard M7-A3; National Committee for Clinical Laboratory Standards: Villanova, Pa.

Formulations and Administration of Antibacterial Agents

The compounds of the present invention can be prepared and administered in a wide variety of oral, topical and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of formula (I) or a pharmaceutically acceptable salt of a compound of formula (I).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment of bacterial infections, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The following examples are offered by way of illustration and are not intended to limit the scope of the invention.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or as noted M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer which scanned from 100 to 1500 daltons. All compounds

Example 1

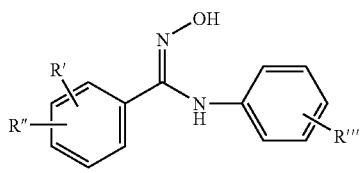

Compound of Formula (Z): R'=3-CF$_3$, R"=H, and R'''=H

Formation of Substituted N-aryl Benzamide

To a stirred solution of aniline (5.0 g, 53.7 mmol) and triethylamine (15 mL, 107 mmol) in CH$_2$Cl$_2$ (100 mL) at 0° C. was added a solution of 3-trifluoromethylbenzoyl chloride (9.5 g, 45.5 mmol, available from Aldrich Chemical Co.) in CH$_2$Cl$_2$ (100 mL) dropwise. After 30 min. of stirring at 0° C., reaction mixture was washed with 1 N HCl three times, dried over MgSO$_4$, filtered and concentrated to give the amide product, which was highly pure and was used without further purification.

Formation of Hydroxy Amidine

The mixture of N-phenyl 3-trifluoromethylbenzamide from above (4.0 g, 15.1 mmol) and phosphorous pentachloride (4.0 g, 1.25 equiv, 18.8 mmol) in 1,2-dichloroethane (100 mL) was heated at 70° C. for 5 h. After cooling to r.t.; solvent was evaporated under redued pressure, toluene was added and the mixture was evaporated again. The residual material was dissolved in acetonitrile and added to a solution of hydroxyamine prepared by stirring hydroxyamine hydrochloride salt (2.60 g, 37.5 mmol) and triethylamine (10.5 mL, 75 mmol) in acetonitrile at 0° C. for 1 h. After stirring overnight at 0° C. to r.t., the reaction mixture was diluted with ethyl acetate and washed with 0.5 N HCl and brine. The organic layer was dried over MgSO$_4$, filtered, and concentrated. The crude product was purified by flash chromatography on silica gel eluted with 6:1 to 3:1 hexane/AcOEt to give 2.5 g of pure product, in 59.2% yield. $^1$H (DMSO) δ 10.8 (s, 1H), 8.46 (s, 1H), 7.70 (d, J=8.0 Hz, 1H), 7.66 (s, 1H), 7.61 (d, J=8.0 Hz, 1H), 7.55 (t, J=8.0 Hz, 1H), 7.08 (t, J=7.4 Hz, 1H), 6.81 (dd, J 8.5, 7.4 Hz, 2H), 6.66 (d, J=8.5 Hz, 2H). MS (ES+): 280 [M+H]$^+$.

Example 2

Compound of Formula (Z): R'=3-CF$_3$, R"=H, and R'''=4-Cl

The title compound was prepared in 15% yield according to method described for Example 1, and substituting 4-chloroaniline for aniline.

$^1$H NMR (CDCl$_3$) δ 8.1(s, 1H), 7.76(s, 1H), 7.63(d, J=9 Hz, 1H), 7.52 (d, J=9.0 Hz, 1H), 7.42 (t, J=9.0 Hz, 1H), 7.22 (s, 1H), 7.09 (d, J=8.8 Hz, 2H), 6.60 (d, J=8.8 Hz, 2H). MS (ES+): 315 (M+H)$^+$. Anal. Calcd. for C$_{14}$H$_{10}$ClF$_3$O: C, 53.43; H, 3.20; N, 8.90. Found: C, 53.24; H, 3.32; N, 8.72.

Example 3

Compound of Formula (Z): R'=3-CF$_3$, R"=H, and R'''=4-CO$_2$Me

The title compound was prepared in 66% yield according to method described for Example 1 except substituting 4-methoxycarbonylaniline for aniline.

$^1$H NMR (CD$_3$OD) δ 7.76 (s, 1H), 7.74 (d, J=8.8 Hz, 2H), 7.67 (m, 2H), 7.52 (t, J=7.7 Hz, 1H), 6.69 (d, J=8.8 Hz, 2H), 3.81 (s, 3H). MS (ES+): 339 (M+H)$^+$. Anal. Calcd. for C$_{16}$H$_{13}$F$_3$N$_2$O$_3$: C, 56.81; H, 3.87; N, 8.28. Found: C, 56.88; H, 3.96; N, 8.25.

Example 4

Compound of Formula (Z): R'=3-CF$_3$, R"=H, and R'''=4-OMe

The title compound was prepared in 20% yield according to method described for Example 1 except substituting 4-methoxyaniline for aniline. $^1$H NMR (CDCl$_3$) δ 7.78 (s, 1H), 7.57 (d, J=7.9 Hz, 1H), 7.52 (d, J=7.9 Hz, 1H), 7.36(t, J=7.9 Hz, 1H), 7.29(s, 1H), 6.66 (s, 4H), 3.70 (s, 3H). MS (ES+): 311 (M+H)$^{30}$. Anal. Calcd. for C$_{15}$H$_{13}$F$_3$N$_2$O$_2$: C, 58.07; H, 4.22; N, 9.03. Found: C, 58.12; H, 4.21; N, 8.92.

Example 5

Compound of Formula (Z): R'=3-Cl, R"=4-Cl, and R'''=3-Cl

The title compound was prepared in 24% yield according to method described for Example 1 except substituting 3,4-dichlorobenzoyl chloride for 3-trifluoromethylbenzoyl chloride and substituting 3-chloroaniline for aniline.

$^1$H NMR (CDCl$_3$) δ 7.82 (s, 1H), 7.60 (s, 1H), 7.38 (d, J=8.3 Hz, 1H), 7.21 (d, J=8.4 Hz, 1H), 7.16 (s, 1H), 7.06 (t, J=8.0 Hz, 1H), 7.95 (d, J=8.0 Hz, 3H), 6.77(s, 1H), 6.48(d, J=8.0 Hz, 1H). MS (ES+): 315 (M+H)$^+$, MS (ES−): 313 (M−H)$^{31}$. Anal. Calcd. for C$_{13}$H$_9$C$_{13}$N$_2$O: C, 49.48; H, 2.87; N, 8.88. Found: C, 49.72; H, 2.96; N, 8.74.

Example 6

Compound of Formula (Z): R'=3-CF$_3$, R"=H, and R'''=3-Cl

The title compound was prepared in 69% yield according to method described for Example 1 except substituting 3-chloroaniline for aniline.

$^1$H NMR (CDCl$_3$) δ 8.85 (s, 1H), 7.77 (s, 1H), 7.65 (d, J=7.7 Hz, 1H), 7.56 (d, J=7.5 Hz, 1H), 7.44 (t, J=7.6 Hz, 1H), 7.27 (s, 1H), 7.02 (t, J=8.1 Hz, 1H), 6.93 (d, J=8.0 Hz, 1H), 6.72 (s, 1H), 6.47 (d, J=8.1 Hz, 1H). MS (ES+): 315 (M+H)$^+$, MS (ES−): 313 (M−H)$^−$. Anal. Calcd. for C$_{14}$H$_{10}$ClF$_3$N$_2$O: C, 53.43; H, 3.20; N, 8.90. Found: C, 53.59; H, 3.39; N, 8.67.

Example 7

Compound of Formula (Z): R'=3-SO$_2$CH$_3$, R"=H, and R'''=H

The title compound was prepared in 10% yield according to method described for Example 1 except substituting 3-methylsulfonylbenzoyl chloride for 3-trifluoromethylbenzoyl chloride.

¹H NMR (CD₃OD) δ 7.92 (s, 1H), 7.89 (d, J=8.0 Hz, 1H), 7.70 (d, J=7.8 Hz, 1H), 7.54 (t, J=8.1 Hz, 1H), 7.10 (t, J=7.8 Hz, 2H), 6.90 (t, 1H), 6.71 (d, J=8.6 Hz, 2H), 2.95(s, 3H). MS (ES+): 291 (M+H)⁺, MS (ES−): 289 (M−H)⁻. Anal. Calcd. for $C_{14}H_{14}N_2O_3S$: C, 57.92; H, 4.86; N, 9.65; S, 11.04. Found: C, 55.07; H, 4.79; N, 8.86; S, 9.88.

Example 8

Compound of Formula (Z): R'=3-SO₂NHPh, R"=H, and R'"=H

The title compound was prepared in 24% yield according to method described for Example 1 except substituting 3-phenylaminosulfonylbenzoyl chloride for 3-trifluoromethylbenzoyl chloride.

¹H NMR (CDCl₃) δ 8.26 (s, 1H), 8.09 (s, 1H), 7.73 (d, J=7.8 Hz, 1H), 7.41 (d, J=7.8 Hz, 2H), 7.27 (m, 2H), 7.12 (t, J=7.8 Hz, 2H), 6.98 (t, J=9.0 Hz, 1H), 6.85 (m, 3H), 6.67 (d, J=7.5 Hz, 2H), 6.56 (d, J=7.4 Hz, 2H). MS (ES+): 368 (M+H)⁺.

Example 9

Compound of Formula (Z): R'=3-Cl, R"=4-Cl, and R'"=H

The title compound was prepared in 19% yield according to method described for Example 1 except substituting 3,4-dichlorobenzoyl chloride for 3-trifluoromethylbenzoyl chloride.

¹H NMR (CD₃OD) δ 7.54 (s, 1H), 7.42 (d, J=8.4 Hz, 1H), 7.25 (d, J=8.4 Hz, 1H), 7.12 (t, J=7.4 Hz, 2H), 6.91 (t, 1H), 6.71 (d, J=7.5 Hz, 2H). MS (ES+): 281 (M+H)⁺. Anal. Calcd. for $C_{13}H_{10}Cl_2N_2O$: C, 55.54; H, 3.59; N, 9.96. Found: C, 55.32; H, 3.79; N, 9.77.

Example 10

Compound of Formula (Z): R'=3-CN, R"=H, and R'"=3-Cl

The title compound was prepared in 24% yield according to method described for Example 1 except substituting 3-cyanobenzoyl chloride for 3-trifluoromethylbenzoyl chloride and substituting 3-chloroaniline for aniline.

¹H NMR (DMSO) δ 11.00 (s, 1H), 8.72 (s, 1H), 7.85 (d, J=7.7 Hz, 1H), 7.82 (s, 1H), 7.67 (d, J=8.1 Hz, 1H), 7.55 (t, J=7.7 Hz, 1H), 7.06(t, J=8.8 Hz, 1H), 6.83 (d, J=8.8 Hz, 1H), 6.78(s, 1H), 6.47(d, J=7.8 Hz, 1H). MS (ES+): 272 (M+H)⁺.

Example 11

Compound of Formula (Z): R'=3-Cl, R"=H, and R'"=3-Cl

The title compound was prepared in 25% yield according to method described for Example 1 except substituting 3-chlorobenzoyl chloride for 3-trifluoromethylbenzoyl chloride and substituting 3-chloroaniline for aniline.

¹H NMR(DMSO) δ 10.90 (s, 1H), 8.64 (s, 1H), 7.45 (d, J=8.6 Hz, 1H), 7.44 (s, 1H), 7.37 (t, J=7.5 Hz, 1H), 7.32 (d, J=7.7 Hz, 1H), 7.07 (t, J=8.1 Hz, 1H), 6.82 (d, J=7.9 Hz, 1H), 6.77 (s, 1H), 6.49 (d, J=8.2 Hz, 1H). MS (ES+): 281 (M+H)⁺, MS (ES−): 279 (M−H)⁻. Anal. Calcd. for $C_{13}H_{10}Cl_2N_2O$: C, 55.54; H, 3.59; N, 9.96. Found: C, 55.49; H, 3.68; N, 9.81.

Example 12

Compound of Formula (Z): R'=3-CO₂CH₃, R"=H, and R'"=H

The title compound was prepared in 38% yield according to method described for Example 1 except substituting 3-methoxycarbonylbenzoyl chloride for 3-trifluoromethylbenzoyl chloride.

¹H NMR (DMSO) δ 10.70 (s, 1H), 8.39 (s, 1H), 8.01 (s, 1H), 7.92 (d, J=7.7 Hz, 1H), 7.58 (d, J=8 Hz, 1H), 7.46 (t, J=7.7 Hz, 1H), 7.06 (t, J=8.0 Hz, 2H), 6.78 (t, J=8.0 Hz, 1H), 6.64 (d, J=7.7 Hz, 2H), 3.82 (s, 3H). MS (ES+): 271 (M+H)⁺. Anal. Calcd. for $C_{15}H_{14}N_2O_3$: C, 66.66; H, 5.22; N, 10.36. Found: C, 66.78; H, 5.34; N, 9.92.

Example 13

Compound of Formula (Z): R'=3-NO₂, R"=4-Cl, and R'"=3-Cl

Following procedures described in Example 1, substituting 3-chloroaniline for aniline and substituting 4-chloro-3-nitrobenzoyl chloride for 3-trifluoromethylbenzoyl chloride the title compound was obtained in 80.0% yield. ¹H (DMSO) δ 11.2 (s, 1H), 8.78 (s, 1H), 8.09 (s, 1H), 7.75 (d, J=8.4 Hz, 1H), 7.62 (d, J=8.4 Hz, 1H), 7.10 (t, J=7.7 Hz, 1H), 6.86 (d, J=7.7 Hz, 1H), 6.85 (s, 1H), 6.68 (d, J=7.7 Hz, 2H). MS (ES+): 328 (M+H)⁺.

Example 14

Compound of Formula (Z): R'=3-NO₂, R"=4-pyrrolidin-1-yl, and R'"=3-Cl

The title compounds was prepared by heating a sample of the compound (0.5 g, 1.51 mmol) from Example 13 was heated with pyrrolidine (5 equiv.) in DMSO (3 mL) at 80° C. for 4 hr followed by typical aqueous washings and chromatographic purification.

¹H NMR (CDCl₃) δ 7.84 (d, J=2.0 Hz, 1 H), 7.30 (dd, J=2.1 Hz, J=9.0 Hz, 2 H), 7.06 (t, J=8 Hz, 1 H), (dm, J=9.0 Hz, 1 H), 6.81 (t, J=2.0 Hz, 1 H), 6.77 (d, J=9 Hz, 1 H), 6.58 (dm, J=8.1 Hz, 1 H), 3.20 (m, 4 H), 1.97 (m, 4 H). MS (ES+): 361 (M+H)⁺.

Example 15

Compound of Formula (Z): R'=3-NO₂, R"=4-Cl, and R'"=H

Following procedures described in Example 1 except substituting 4-chloro-3-nitrobenzoyl chloride for 3-trifluoromethylbenzoyl chloride the title compound was obtained in 65.8% yield.

¹H (DMSO) δ 11.0 (s, 1H), 8.54 (s, 1H), 8.03 (s, 1H), 7.70 (d, J=8.4 Hz, 1H), 7.55 (d, J=8.4 Hz, 1H), 7.11 (t, J=7.7 Hz, 2H), 6.84 (d, J=7.7 Hz, 1H), 6.68 (d, J=7.7 Hz, 2H). MS (ES+): 292 (M+H)⁺.

Example 16

Compound of Formula (Z): R'=3-CF₃, R"=4-F, and R'"=H

The desired compound was prepared according to the method of Example 1 except substituting 4-fluoro-3-trifluoromethylbenzoyl chloride for 3-trifluoromethylbenzoyl chloride (35.6% yield).

¹H (DMSO) δ 10.8 (s, 1H), 8.49 (s, 1H), 7.69 (d, J=7.5 Hz, 1H), 7.65 (m, 1H), 7.48 (t, J=7.5 Hz, 1H), 7.09 (t, J=8.0 Hz, 2H), 6.82 (t, J=8.0 Hz, 1H), 6.67(d, J=8.0 Hz, 2H). MS (ES+): 299 (M+H)+.

Example 17

Compound of Formula (Z): R'=3-CF$_3$, R"=4-F, and R'''=3-Cl

The desired compound was prepared according to the method of Example 1 except substituting 4-fluoro-3-trifluoromethylbenzoyl chloride for 3-trifluoromethylbenzoyl chloride and substituting 3-chloroaniline for aniline (31.7% yield).

¹H (DMSO) δ 11.0 (s, 1H), 8.73 (s, 1H), 7.75 (d, J=6.9 Hz, 1H), 7.68 (m, 1H), 7.50 (t, J=6.9 Hz, 1H), 7.09 (t, J=8.0 Hz, 1H), 6.85 (d, J=8.0 Hz, 1H), 6.80(s, 1H), 6.48 (d, J=8.0 Hz, 1H). MS (ES+): 333 (M+H)+.

Example 18

Compound of Formula (Z): R'=3-CF$_3$, R"=4-N$_3$, and R'''=3-Cl

Step 18a. Following procedures described in of Example 1 except substituting 4-fluoro-3-trifluoromethylbenzoyl chloride for 3-trifluoromethylbenzoyl chloride and substituting 3-chloroaniline for aniline the corresponding N-3-chlorophenyl 4-fluoro-3-trifluoromethylbenzamide was obtained.

Step 18b. A sample of the amide from above was treated in DMSO with NaN$_3$ in DMSO at 110° C. for 4 hr. After cooling to room temperature, the reaction mixture was diluted with ethyl acetate and washed thoroughly with water and brine. The organic layer was dried over MgSO$_4$, filtered and concentrated to give 3-chlorophenyl 4-azido-3-trifluoromethylbenzamide.

Step 18c. The mixture of N-3-chlorophenyl 4-azido-3-trifluoromethylbenzamide from Step 18b (5.8 g, 17.0 mmol) and phosphorous pentachloride (4.4 g, 1.25 equiv., 21.2 mmol) in 1,2-dichloroethane (100 mL) were heated at 70° C. for 5 h. After cooling to r.t., solvent was evaporated under reduced pressure. Toluene was added and was evaporated again. The residual material was dissolved in acetonitrile (50 mL) and was added to the solution of hydroxyamine prepared by stirring hydroxyamine hydrochloride salt (4.0 g, 57.5 mmol) and triethylamine (16 mL, 115 mmol) in acetonitrile (50 mL) at 0° C. for 1 h. After stirring overnight at 0° C. to r.t., the reaction mixture was diluted with ethyl acetate and was washed with 0.5 N HCl and brine. Organic layer was dried over MgSO$_4$, filtered, and concentrated. The crude product was purified by flash chromatography on silica gel eluted with 6:1 to 3:1 hexane/AcOEt to give pure product, 4.5 g, in 70% yield.

¹H (DMSO) δ 11.1 (s, 1H), 8.69 (s, 1H), 7.71 (s, 1H), 7.68 (d, J=8.4 Hz, 1H), 7.55 (d, J=8.4 Hz, 1H), 7.01 (t, J=8.0 Hz, 1H), 6.83 (d, J=8.0 Hz, 1H), 6.81(s, 1H), 6.48 (d, J=8.0 Hz, 1H). MS (ES+): 358 (M+H)+.

Example 19

Compound of Formula (Z): R'=3-CF$_3$, R"=4-NH$_2$, and R'''=3-Cl

To a solution of the azido-substituted compound (325 mg, 0.91 mmol) from Example 18 above in EtOH-THF (6/1 mL) at 0° C. was added a freshly prepared solution of SnCl$_2$.2H$_2$O (308 mmg, 1.37 mmol, 1.5 equiv.) in 2N NaOH. TLC analysis revealed completion of reaction in 30 min. The resulted slurry was filtered through a Celite pad, which was rinsed with ethyl acetate. The filtrate was diluted with brine and ethyl acetate. The layers were separated, organic phase was washed with brine twice, dried over MgSO4, filtered and concentrated. The crude product was purified by flash chromatography on silica gel eluted with 3:1 hexane/AcOEt to give pure product, 233 mg, in 77% yield. ¹H (DMSO) δ 10.5 (s, 1H), 8.43 (s, 1H), 7.37 (s, 1H), 7.25 (d, J=8.5 Hz, 1H), 7.08 (t, J=7.7 Hz, 1H), 6.81 (d, J=8.5 Hz, 1H), 6.77 (s, 1H), 6.76 (d, J=7.7 Hz, 1H), 6.53 (d, J=7.7 Hz, 1H), 5.8 (s, 2H). MS (ES+): 330 (M+H)+.

Example 20

Compound of Formula (Z): R'=3-CF$_3$, R"=4-NH-NH$_2$, and R'''=3-Cl

A sample of the 4-F compound (0.5 g, 1.51 mmol) from Example 17 was heated with hydrazine monohydrate (0.75 mL) in DMSO (3 mL) at 80° C. for 4 hr. The title compound was obtained following typical aqueous washings and chromatographic purification in 85% yield.

¹H (DMSO) δ 10.5 (s, 1H), 8.42 (s, 1H), 7.42 (s, 1H), 7.39 (d, J=7.5 Hz, 1H), 7.32 (t, J=7.5 Hz, 1H), 7.08 (d, J=7.5 Hz, 1H), 6.97 (s, 1H), 6.78 (d, J=7.2 Hz, 1H), 6.75 (s, 1H), 6.51 (d, J=7.2 Hz, 1H), 4.25 (s, 2H). MS (ES+): 345 (M+H)+.

Example 21

Compound of Formula (Z): R'=3-CF$_3$, R"=4-morpholin-1-yl, and R'''=H

A sample of the 4-F compound from Example 16 was heated with morpholine (5 equiv.) in DMSO at 80° C. for 4 hr. The title compound was obtained following typical aqueous washings and chromatographic purification.

¹H NMR (DMSO): δ 10.7 (s, 1H), 8.37 (s, 1H), 7.64 (s, 1H), 7.57 (d, J=8.4 Hz, 1H), 7.46 (d, J=8.4 Hz, 1H), 7.09 (t, J=7.3 Hz, 2H), 6.82 (t, J=7.3 Hz, 1H), 6.68 (d, J=7.3 Hz, 2H), 3.69 (t, J=3.0 Hz, 4H), 2.86 (t, J=3.0 Hz, 4H). MS (ES): 366 [M+H]+.

Example 22

Compound of Formula (Z): R'=3-CF$_3$, R"=4-pyrrolidin-1-yl, and R'''=H

A mixture of the 4-F compound from Example 16 (0.035 g, 0.117 mmol) and pyrrolidine (0.068 ml, 0.82 mmol) in DMSO (1 ml) was heated to 100° C. overnight. The mixture was poured into brine and extracted with EtOAc. The organic layer was separated, washed with brine, dried with anhydrous Na$_2$SO$_4$, concentrated by rotary evaporation and purified by flash chromatography on silica gel with a gradient elution of 30–40% EtOAc/hexanes to yield the title compound as a white solid (0.038 g, 95%).

¹H NMR (DMSO-d$_6$): δ 10.43 (s, 1H), 8.20 (s, 1H), 7.57 (s, 1H), 7.35 (d, J=9.1 Hz, 1H), 7.10 (m, 2H), 6.94 (d, J=9.1 Hz, 1H), 6.79 (m, 1H), 6.70 (d, J=9.1 Hz, 2H), 3.30 (m, 4H), 1.90 (m, 4H). MS (ES): 350 [M+H]+.

Example 23

Compound of Formula (Z): R'=3-CF$_3$, R"=4-(3-methyl)piperidin-1-yl, and R'''=H

The title compound was synthesized according to the procedures used for Example 22 of above starting from the compound of Example 16 (0.06 g, 0.2 mmol), 3-methylpiperidine (0.234 ml, 2 mmol) and DMSO (1 ml). The reaction was conducted at 120° C. for 24 hrs. Purification was performed by flash chromatography on silica gel with a gradient elution of 30–40% EtOAc/hexanes to yield the desired compound as an oil (0.029 g, 38%).

$^1$H NMR (CDCl$_3$): δ 7.73 (s, 1H), 7.45 (d, J=8.4 Hz, 1H), 7.25 (m, 1 H), 7.12 (m, 3H), 6.95 (m, 1H), 6.68 (d, J=8.4 Hz, 2H), 3.03 (m, 2H), 2.59 (m, 1H), 2.29 (t, J=8.7 Hz, 1H), 1.73 (m, 5H), 0.99 (m, 1H), 0.88 (d, J=6.2 Hz, 3H). MS (ES): 378 [M+H]$^+$.

Example 24

Compound of Formula (Z): R'=3-CF$_3$, R"=4-(4-methyl)piperidin-1-yl, and R'''=H

The title compound was synthesized according to the procedures used for Example 22 starting from a sample of compound from Example 16 (0.06 g, 0.2 mmol), 4-methylpiperidine (0.236 ml, 2 mmol) and DMSO (1 ml). The reaction was conducted at 120° C. for 24 hrs. Purification was performed by flash chromatography on silica gel with a gradient elution of 30–40% EtOAc/hexanes to the title compound as an oil (0.027 g, 36%).

$^1$H NMR (CDCl$_3$) δ 7.73 (s, 1H), 7.46 (d, J=8.4 Hz, 1H), 7.25 (m, 1 H), 7.14 (m, 3H), 6.95 (t, J=7.7 Hz, 1H), 6.68 (d, J=8.5 Hz, 2H), 3.08 (d, J=11.7 Hz, 2H), 2.66 (t, J=11.7 Hz, 2H), 1.67 (d, J=11.9 Hz, 2 H), 1.40 (m, 4H), 0.97 (d, J=6.2 Hz). MS (ES): 378 [M+H]$^+$.

Example 25

Compound of Formula (Z): R'=3-CF$_3$, R"=4-(4-methyl)piperazin-1-yl, and R'''=H

Synthesized according to the same procedure as was used for Example 22 starting from the compounds of Example 16 (0.12 g, 0.4 mmol), 1-methylpiperazine (0.311 ml, 2.8 mmol) and DMSO (1.5 ml). The reaction was conducted at 120° C. for 2 days and then 140° C. for another 24 hrs. Purification was performed by flash chromatography on silica gel with a gradient elution of 5–25% MeOH/CH$_2$Cl$_2$ to yield the title compound as a white solid (0.138 g, 91%).

$^1$H NMR (DMSO) δ 10.68 (s, 1H), 8.36 (s, 1H), 7.63 (s, 1H), 7.55 (d, J=8.4 Hz, 1H), 7.43 (d, J=8.4 Hz, 1H), 7.09 (t, J=7.9 Hz, 2H), 6.81 (t, J=7.9 Hz, 1H), 6.66 (d, J=7.6 Hz, 2H), 2.86 (m, 4H), 2.43 (m, 4H), 2.21 (s, 3H). MS (ES): 379 [M+H]$^+$.

Example 26

Compound of Formula (Z): R'=3-CF$_3$, R"=4-(4-phenyl)piperazin-1-yl, and R'''=H

The title compound was synthesized according to the procedures used for Example 22 starting from the compounds of Example 16 (0.06 g, 0.2 nmmol), 1-phenylpiperazine(0.206 ml, 2 mmol) and DMSO (1 ml). The reaction was conducted at 120° C. for 24 hrs. Purification was performed by flash chromatography on silica gel with a gradient elution of 30–40% EtOAc/hexanes to yield the title compound as a solid (0.027 g, 23%).

$^1$H NMR (CDCl$_3$) δ 7.79 (s, 1H), 7.81 (d, J=7.5 Hz, 1H), 7.25 (m, 4H), 7.15 (dd, J=7.9, 7.9 Hz, 2H), 6.97 (m, 4H), 6.89 (dd, 6.8, 6.8 Hz, 1H), 6.71 (d, J=7.5 Hz, 2H), 3.31 (m, 4H), 3.11 (m, 4H). MS (ES): 441 [M+H]$^+$.

Example 27

Compound of Formula (Z): R'=3-CF$_3$, R"=4-piperidin-1-yl, and R'''=H

The title compound was synthesized according to the procedures used for the synthesis of Example 22 starting from the compounds of Example 16 (0.06 g, 0.2 mmol), piperidine (0.198 ml, 2 mmol) and DMSO (1 ml). The reaction was conducted at 120° C. for 24 hrs. Purification was performed by flash chromatography on silica gel with a gradient elution of 30–40% EtOAc/hexanes to yield the title compound as an oil (0.036 g, 50%).

$^1$H NMR (DMSO) δ 10.66 (s, 1H), 8.34 (s, 1H), 7.62 (s, 1H), 7.54 (d, J=8.4 Hz, 1H), 7.40 (d, J=8.4 Hz, 1H), 7.09 (dd, J=8.4, 8.4 Hz, 2H), 6.81 (dd, J=7.5 Hz, 1H), 6.66 (d, J=7.4 Hz, 2H), 2.80 (m, 4H), 1.45–2.70 (m, 6H). MS (ES): 364 [M+H]$^+$.

Example 28

Compound of Formula (Z): R'=3-CF$_3$, R"=4-azetidinyl, and R'''=H

The title compound was synthesized according to the same procedure used Example 22 starting from the compounds of Example 16 (0.12 g, 0.4 mmol), azetidine (0.189 ml, 2.8 mmol) and DMSO (1.5 ml). The reaction was conducted at 110° C. for 14 hrs. Purification was performed by flash chromatography on silica gel with a gradient elution of 30–40% EtOAc/hexanes to yield product as a white solid (0.09 g, 67%).

$^1$H NMR (DMSO) δ 10.39 (s, 1H), 8.18 (s, 1H), 7.48 (s, 1H), 7.34 (d, J=8.7 Hz, 1H), 7.08 (dd, J=7.7, 7.7 Hz, 2H), 6.79 (dd, J=7.5, 7.5 Hz, 1H), 6.66 (d, J=8.3 Hz, 2H), 6.47 (d, J=8.7 Hz, 1H), 2.80 (m, 4H), 1.45–2.70 (m, 6H). MS (ES): 336 [M+H]$^+$.

Example 29

Compound of Formula (Z): R'=3-CF$_3$, R"=4-(S)-(2-methoxymethyl)pyrrolidin-1yl, and R'''=H The title compound was synthesized according to the same procedure for Example 22 starting from the compounds of Example 16, (S)(+)-2-methoxymethylpyrrolidine (0.346 ml, 2.8 mmol) and DMSO (1.5 ml). The reaction was conducted at 120° C. for 2 days. Purification was performed by flash chromatography on silica gel with a gradient elution of 30–45% EtOAc/hexanes to yield product as an oil (0.04 g, 25%).

$^1$H NMR (DMSO) δ 10.55 (s, 1H), 8.29 (s, 1H), 7.58 (s, 1H), 7.45 (d, J=7.6 Hz, 1H), 7.31 (d, J=7.6 Hz, 1H), 7.08 (dd, J=7.6, 7.6 Hz, 2H), 6.80 (dd, J=7.6, 7.6 Hz, 1H), 6.67 (d, J=7.6 Hz, 2H), 4.33 (t, J=5.6 Hz, 1H), 3.87 (m, 1H), 3.40 (m, 1H), 3.21 (m, 1H), 3.11 (s, 3H), 2.95 (m, 1H), 2.1 (m, 1H), 1.65–1.90 (m, 3H). MS (ES): 394 [M+H]$^+$.

Example 30

Compound of Formula (Z): R'=3-CF$_3$, R"=4-[(R)-3-dimethylamino]pyrrolidin-1yl, and R'"=H The title compound was synthesized according to the same procedure used for Example 22 starting from the compounds of Example 16 (0.12 g, 0.4 mmol), (R)(+)-3-dimethylaminopyrrolidine (0.355 ml, 2.8 mmol) and DMSO (1.5 ml). The reaction was conducted at 120° C. for 24 hrs. Purification was performed by flash chromatography on silica gel with a gradient elution of 5–25% MeOH/CH$_2$Cl$_2$ to yield desired product as a white solid (0.105 g, 67%).

$^1$H NMR (DMSO) δ 10.45 (s, 1H), 8.22 (s, 1H), 7.56 (s, 1H), 7.36 (d, J=11.1 Hz, 1H), 7.09 (dd, J=8.3, 8.3 Hz, 2H), 6.95 (d, J=8.3 Hz, 1H), 6.80 (d, J=6.9 Hz, 1H), 6.67 (d, J=7.6 Hz, 1H), 3.3–3.5 (m, 2H), 3.22 (t, J=8.3 Hz, 1H), 2.71 (quint, J=7.8 Hz, 1H), 2.16 (s, 6H), 2.09 (m, 1H), 1.74 (quint, J=9.4 Hz, 1H). MS (ES): 393 [M+H]$^+$.

Example 31

Compound of Formula (Z): R'=3-CF$_3$, R"=4-[(±)-2-methyl]pyrrolidin-1-yl, and R'"=H Synthesized according to the same procedure as was used for Example 22 starting from the compounds of Example 16 (0.12 g, 0.4 mmol), 2-methylpyrrolidine (0.286 ml, 2.8 mmol) and DMSO (1.5 ml). The reaction was conducted at 120° C. for 1.5 days. Purification was performed by flash chromatography on silica gel with a gradient elution of 25–35% EtOAc/hexanes to yield product as a white solid (0.09 g, 62%).

$^1$H NMR (DMSO) δ 10.5 (s, 1H), 8.22 (s, 1H), 7.59 (s, 1H), 7.43 (d, J=8.3 Hz, 1H), 7.19 (d, J=8.7 Hz, 1H), 7.09 (dd, J=7.9, 7.9 Hz, 2H), 6.80 (dd, J=7.8, 7.8 Hz, 1H), 6.67 (d, J=7.6 Hz, 2H), 3.72 (m, 1H), 3.46 (m, 1H), 2.95 (m, 1H), 2.11 (m, 1H), 1.86 (m, 1H), 1.75 (m, 1H), 1.50 (m, 1H), 0.95 (d, J=6.0 Hz, 3H). MS (ES): 364 [M+H]$^+$.

Example 32

Compound of Formula (Z): R"=3-CF$_3$, R"=4-[(R)-3-hydroxy]pyrrolidin-1-yl, and R'"=H Synthesized according to the same procedure as was used for Example 22 starting from the compounds of Example 16 (0.12 g, 0.4 mmol), (R)(+)-3-pyrrolidinol (0.233 ml, 2.8 mmol) and DMSO (1.5 ml). The reaction was conducted at 120° C. overnight. Purification was performed by flash chromatography on silica gel with a gradient elution of 60–100% EtOAc/hexanes to give product as a white solid (0.1 g, 68%).

$^1$H NMR (DMSO) δ 10.41 (s, 1H), 8.20 (s, 1H), 7.56 (s, 1H), 7.34 (d, J=8.9 Hz, 1H), 7.09 (dd, J=7.6, 7.6 Hz, 2H), 6.90 (d, J=8.8 Hz, 1H), 6.79 (dd, J=7.3, 7.3 Hz, 1H), 6.68 (d, J=8.4 Hz, 2H), 4.96 (d, J=3.2 Hz, 1H), 4.33 (m, 1H), 3.4–3.6 (m, 2H), 3.28 (m, 1H), 3.10 (d, J=10.6, 1H), 1.96 (m, 1H), 1.84 (m, 1H). MS (ES): 366 [M+H]$^+$.

Example 33

Compound of Formula (Z): R'=3-CF$_3$, R"=4-[(S)-2-hydroxymethyl]pyrrolidin-1-yl, and R'"=H Synthesized according to the same procedure as was used for Example 22 starting from the compounds of Example 16 (0.12 g, 0.4 mmol), (S)(+)-2-hydroxymethylpyrrolidine (0.276 ml, 2.8 mmol) and DMSO (1.5 ml). The reaction was conducted at 120° C. overnight. Purification was performed by flash chromatography on silica gel with a gradient elution of 60–100% EtOAc/hexanes to give product as a white solid (0.05 g, 33%).

$^1$H NMR (DMSO) δ 10.54 (s, 1H), 8.27 (s, 1H), 7.56 (s, 1H), 7.42 (d, J=8.7 Hz, 1H), 7.25 (d, J=8.6 Hz, 1H), 7.09 (dd, J=7.9, 7.9 Hz, 2H), 6.81 (dd, J=7.4, 7.4 Hz, 1H), 6.67 (d, J=7.6 Hz, 2H), 4.52 (t, J=5.0 Hz, 1H), 3.77 (m, 1H), 3.43 (m, 1H), 3.16 (m, 2H), 2.99 (m, 1H), 2.10 (m, 1H), 1.74 (m, 3 H). MS (ES): 380 [M+H]$^+$.

Example 34

Compound of Formula (Z): R'=3-CF$_3$, R"=4-(4-pyrrolidin-1-yl)piperidin-1-yl, and R'"=H Synthesized according to the same procedure as was used for Example 22 starting from the compounds of Example 16 (0.12 g, 0.4 mmol), 4-(1-pyrrolidinyl)piperidine (0.432 g, 2.8 mmol) and DMSO (1.5 ml). The reaction was conducted at 120° C. for 2.5 days. Purification was performed by flash chromatography on silica gel with a gradient elution of 0–10% NH$_4$OH in 30% MeOH/CH$_2$Cl$_2$ to yield product as a white solid (0.105 g, 61%).

$^1$H NMR (DMSO) δ 10.68 (s, 1H), 8.34 (s, 1H), 7.62 (s, 1H), 7.52 (d, J=8.5 Hz, 1H), 7.38 (d, J=8.5 Hz, 1H), 7.09 (dd, J=7.9, 7.9 Hz, 2H), 6.80 (dd, J=7.7, 7.7 Hz, 1H), 6.65 (d, J=8.4 Hz, 2H), 2.97 (m, 2H), 2.72 (m, 2H), 2.10 (m, 1H), 1.89 (m, 4H), 1.67 (m, 6H), 1.50 (m, 2H). MS (ES): 433 [M+H]$^+$.

Example 35

Compound of Formula (Z): R'=3-CF$_3$, R"=4-pyrrolin-1-yl, and R'"=H

Synthesized according to the same procedure as was used for Example 22 starting from the compounds of Example 16 (0.12 g, 0.4 mmol), pyrroline (0.215 ml, 2.8 mmol) and DMSO (1.5 ml). The reaction was conducted at 130° C. for 1.5 days. Purification was performed by flash chromatography on silica gel with a gradient elution of 30–45% EtOAc/hexanes to yield product as a white solid (0.062 g, 45%).

$^1$H NMR (DMSO) δ 10.44 (s, 1H), 8.23 (s, 1H), 7.61 (s, 1H), 7.36 (d, J=8.8 Hz, 1H), 7.09 (dd, J=7.4, 7.4 Hz, 2H), 6.93 (d, J=8.8 Hz, 1H), 6.80 (dd, J=7.8, 7.8 Hz, 1H), 6.68 (dd, J=8.4, 8.4 Hz, 2H), 5.97 (s, 2H), 4.20 (s, 4H). MS (ES): 348 [M+H]$^+$.

Example 36

Compound of Formula (Z): R'=3-CF$_3$, R"=4-cyclobutylamino, and R'"=H

Synthesized according to the same procedure used for Example 22 starting from the compounds of Example 16 (0.12 g, 0.4 mmol), cyclobutylamine (0.239 ml, 2.8 mmol) and DMSO (1.5 ml). The reaction was conducted at 130° C. for 24 hrs. Purification was performed by flash chromatography on silica gel with a gradient elution of 30–40% EtOAc/hexanes to yield product as a white solid (0.1 g, 72%).

$^1$H NMR (DMSO) δ 10.36 (s, 1H), 8.17 (s, 1H), 7.41 (s, 1H), 7.33 (d, J=8.9 Hz, 1H), 7.08 (dd, J=7.9, 7.9 Hz, 2H), 6.79 (dd, J=7.2, 7.2 Hz, 1H), 6.66 (m, 3H), 5.37 (d, J=6.2 Hz, 1H), 3.91 (m, 1H), 2.32 (m, 2H), 1.97 (m, 2H), 1.69 (m, 2H). MS (ES): 350 [M+H]$^+$.

Example 37

Compound of Formula (Z): R'=3-CF$_3$, R"=4-cyclopentylamino, and R'"=3-Cl

Synthesized according to the same procedure as was used Example 22 starting from the compounds of Example 17 (0.1 g, 0.3 mmol), cyclopentylamine (0.201 ml, 2.1 mmol) and DMSO (1.2 ml). The reaction was conducted at 130° C. for 20 hrs. Purification was performed by flash chromatography on silica gel with a gradient elution of 30–35% EtOAc/hexanes to yield product as a white solid (0.08 g, 67%).
$^1$H NMR (DMSO) δ 10.54 (s, 1H), 8.45 (s, 1H), 7.45 (s, 1H), 7.39 (d, J=8.9 Hz, 1H), 7.07 (dd, J=7.3, 7.3 Hz, 1H), 6.82 (m, 3H), 6.51 (d, J=7.3 Hz, 1H), 4.89 (d, J=5.6 Hz, 1H), 3.87 (m, 1H), 1.97 (m, 2H), 1.43–1.70 (m, 6H). MS (ES): 398 [M+H]$^+$.

Example 38

Compound of Formula (Z): R'=3-CF$_3$, R"=4-pyrrolidin-1-yl, and R'"=3-Cl

Synthesized according to the same procedure as was used for Example 22 starting from the compounds of Example 17 (0.1 g, 0.3 mmol), pyrrolidine (0.175 ml, 2.1 mmol) and DMSO (1.2 ml). The reaction was conducted at 110° C. overnight. Purification was performed by flash chromatography on silica gel with a gradient elution of 30–35% EtOAc/hexanes to give product as a white solid (0.06 g, 52%).
$^1$H NMR (DMSO) δ 10.61 (s, 1H), 8.48 (s, 1H), 7.59 (s, 1H), 7.38 (d, J=8.9 Hz, 1H), 7.07 (dd, J=8.3, 8.3 Hz, 1H), 6.96 (d, J=8.3 Hz, 1H), 6.80 (m, 2H), 6.50 (d, J=8.3 Hz, 1H), 3.35 (m, 4H), 1.89 (m, 4H). MS (ES): 384 [M+H]$^+$.

Example 39

Compound of Formula (Z): R'=3CF$_3$, R"=4-piperidin-1-yl, and R'"=3-Cl

Synthesized according to the same procedure as was used for Example 22 starting from the compounds of Example 17 (0.1 g, 0.3 mmol), piperidine (0.208 ml, 2.1 mmol) and DMSO (1.2 ml). The reaction was conducted at 130° C. for 24 hrs. Purification was performed by flash chromatography on silica gel with a gradient elution of 30–35% EtOAc/hexanes to yield product as a solid (0.05 g, 42%).
$^1$H NMR (DMSO) δ 10.85 (s, 1H), 8.62 (s, 1H), 7.64 (s, 1H), 7.58 (d, J=8.3 Hz, 1H), 7.43 (d, J=8.3 Hz, 1H), 7.08 (dd, J=8.6, 8.6 Hz, 1H), 6.83 (d, J=8.4 Hz, 1H), 6.74 (s, 1H), 6.50 (d, J=8.3 Hz, 1 H), 2.82 (m, 4H), 1.61 (m, 4H), 1.52 (m, 2H). MS (ES): 398 [M+H]$^+$.

Example 40

Compound of Formula (Z): R'=3-CF$_3$, R"=4-pyrrolin-lyl, and R'"=3-Cl

Synthesized according to the same procedure as was used for Example 22 starting from the compounds of Example 17 (0.1 g, 0.3 mmol), 3-pyrroline (0.208 ml, 2.1 mmol) and DMSO (1.2 ml). The reaction was conducted at 120° C. for 24 hrs. Purification was performed by flash chromatography on silica gel with 30% EtOAc/hexanes as eluent to yield product as a solid (0.08 g, 87%).
$^1$H NMR (DMSO) δ 10.6 (s, 1H), 8.50 (s, 1H), 7.64 (s, 1H), 7.41 (d, J=8.9 Hz, 1H), 7.08 (dd, J=8.4, 8.4 Hz, 1H), 6.96 (d, J=8.9 Hz, 1H), 6.80 (m, 2H), 6.52 (d, J=7.6 Hz, 1H), 5.98 (s, 2H), 4.22 (s, 4H). MS (ES): 382 [M+H]$^+$.

Example 41

Compound of Formula (Z): R'=3-CF$_3$, R"=4-benzylamino, and R'"=3-Cl

Synthesized according to the same procedure as was used for Example 22 starting from the compounds of Example 17 (0.1 g, 0.3 mmol), benzylamine (0.23 ml, 2.1 mmol) and DMSO (1.2 ml). The reaction was conducted at 120° C. for 1.5 days. Purification was performed by flash chromatography on silica gel with a gradient elution of 30–35% EtOAc/hexanes to yield product as a white solid (0.08 g, 64%).
$^1$H NMR (DMSO) δ 10.50 (s, 1H), 8.41 (s, 1H), 7.45 (s, 1H), 7.15–7.35 (m, 6H), 7.05 (dd, J=8.0, 8.0 Hz, 1H), 6.80 (d, J=8.3 Hz, 1H), 6.72 (s, 1H), 6.59 (dd, J=9.1, 9.1 Hz, 2H), 6.51 (d, J=8.3 Hz, 1H), 4.65 (d, J=5.9 Hz, 2H). MS (ES): 420 [M+H]$^+$.

Example 42

Compound of Formula (Z): R'=3-CF$_3$, R"=4-(tetrahydrofur-2-yl)amino, and R'"=3-Cl Synthesized according to the same procedure as was used for Example 22 starting from the compounds of Example 17 (0.1 g, 0.3 mmol), tetrahydrofurylamine (0.217 ml, 2.1 mmol) and DMSO (1.2 ml). The reaction was conducted at 130° C. for 1.5 days. Purification was performed by flash chromatography on silica gel with a gradient elution of 35–45% EtOAc/hexanes to give product as a white solid (0.045 g, 36%). $^1$H NMR (DMSO) δ 10.54 (s, 1H), 8.45 (s, 1H), 7.45 (s, 1H), 7.36 (d, J=8.3 Hz, 1H), 7.07 (dd, J=8.3, 8.3 Hz, 1H), 6.86 (d, J=8.8 Hz, 1H), 6.78 (m, 2H), 6.51 (d, J=8.3 Hz, 1H), 5.41 (m, 1H), 4.04 (m, 1H), 3.75 (m,1H), 3.63 (m, 1H), 3.29 (m, 1H), 3.18 (m, 1H), 1.75–2.0 (m, 3H), 1.59 (m, 1H). MS (ES): 414 [M+H]$^+$.

Example 43

Compound of Formula (Z): R'=3-CF$_3$, R"=4-(3-dimethylamino)propylamino, and R'"=3-Cl Synthesized according to the same procedure as was used for Example 22 starting from the compounds of Example 17 (0.1 g, 0.3 mmol), 3,3-dimethylaminopropylamine (0.264 ml, 2.1 mmol) and DMSO (1.2 ml). The reaction was conducted at 130° C. for 1.5 days. Purification was performed by flash chromatography on silica gel with a gradient elution of 2.5–5% NH$_4$OH in 30% MeOH/CH$_2$Cl$_2$ to give product as an oil (0.035 g, 28%).
$^1$H NMR (DMSO) δ 10.51 (s, 1H), 8.44 (s, 1H), 7.44 (s, 1H), 7.37 (d, J=8.3 Hz, 1H), 7.07 (dd, J=8.3, 8.3 Hz, 1H), 6.79 (m, 2H), 6.72 (m, 2H), 6.51 (d, J=8.3 Hz, 1H), 3.21 (m, 2H), 2.38 (t, J=5.0 Hz, 2H), 2.16 (s, 6H), 1.71 (m, 2H). MS (ES): 415 [M+H]$^+$.

Example 44

Compound of Formula (Z): R'=3-CF$_3$, R"=4-azetidino, and R'''=3-Cl

Synthesized according to the same procedure as was used for Example 22 starting from the compounds of Example 17 (0.1 g, 0.3 mmol), azetidine (0.25 g, 4.38 mmol) and DMSO (1.2 ml). The reaction was conducted at 110° C. for 18 hrs. Purification was performed by flash chromatography on silica gel with a gradient elution of 30–40% EtOAc/hexanes to yield product as an oil (0.022 g, 20%).

$^1$H NMR (DMSO) δ 10.57 (s, 1H), 8.47 (s, 1H), 7.51 (s, 1H), 7.38 (d, J=8.3 Hz, 1H), 7.07 (dd, J=8.3, 8.3 Hz, 1H), 6.79 (m, 2H), 6.51 (m, 2H), 4.02 (m, 4H), 2.26 (m, 2H). MS (ES): 370 [M+H]$^+$.

Example 45

Compound of Formula (Z): R'=3-CF$_3$, R"=4-[(R)-(+)-3-hydroxy]pyrrolidin-1-yl, and R'''=3-Cl Synthesized according to the same procedure as was used for Example 22 starting from the compounds of Example 17 (0.1 g, 0.3 mmol), (R)-(+)-3-pyrrolidinol (0.175 ml, 2.1 mmol) and DMSO (1.2 ml). The reaction was conducted at 120° C. overnight. Purification was performed by flash chromatography on silica gel with a gradient elution of 60–80% EtOAc/hexanes to yield product as a white solid (0.09 g, 75%).

$^1$H NMR (DMSO) δ 10.60 (s, 1H), 8.48 (s, 1H), 7.59 (s, 1H), 7.37 (d, J=8.3 Hz, 1H), 7.08 (dd, J=8.4, 8.4 Hz, 1H), 6.94 (d, J=8.9 Hz, 1H), 6.80 (m, 2H), 6.50 (d, J=8.3 Hz, 1H), 4.97 (d, J=3.4 Hz, 1H), 4.35 (s, 1H, broad), 3.52 (m, 2H), 3.29 (m, 1H), 3.11 (d, J=11.1 Hz, 1H), 1.96 (m, 1H), 1.85 (m, 1H). MS (ES): 400 [M+H]$^+$.

Example 46

Compound of Formula (Z): R'=3-CF$_3$, R"=4-cyclopropylmethylamino, and R'''=3-Cl Synthesized according to the same procedure as was used for Example 22 starting from the compounds of Example 17 (0.1 g, 0.3 mmol), cyclopropylmethyl amine (0.182 ml, 2.1 mmol) and DMSO (1.2 ml). The reaction was conducted at 130° C. for 20 hrs. Purification was performed by flash chromatography on silica gel with a gradient elution of 30–35% EtOAc/hexanes to give rpoduct as an oil (0.08 g, 69%).

$^1$H NMR (DMSO) δ 10.52 (s, 1H), 8.44 (s, 1H), 7.44 (s, 1H), 7.37 (d, J=8.3 Hz, 1H), 7.08 (dd, J=8.3, 8.3 Hz, 1H), 6.81 (m, 3H), 6.80 (m, 2H), 6.52 (d, J=8.3 Hz, 1H), 5.58 (m, 1H), 4.35 (s, 1H, broad), 3.52 (m, 2H), 3.07 (m, 2H), 1.09 (m, 1H), 0.43 (m, 2H), 0.24 (m, 2H). MS (ES): 384 [M+H]$^+$.

Example 47

Compound of Formula (Z): R'=3-CF$_3$, R"=4-(3-hydroxy)propylamino, and R'''=3-Cl Synthesized according to the same procedure as was used for Example 22 starting from the compounds of Example 17 (0.1 g, 0.3 mmol), 3-amino-1-propanol (0.161 ml, 2.1 mmol) and DMSO (1.2 ml). The reaction was conducted at 130° C. for 20 hrs. Purification was performed by flash chromatography on silica gel with a gradient elution of 60–90% EtOAc/hexanes to yield product as a white solid (0.07 g, 60%).

$^1$H NMR (DMSO) δ 10.51 (s, 1H), 8.44 (s, 1H), 7.44 (s, 1H), 7.38 (d, J=8.3 Hz, 1H), 7.08 (dd, J=8.3, 8.3 Hz, 1H), 6.79 (m, 3H), 6.80 (m, 2H), 6.51 (d, J=8.3 Hz, 1H), 5.88 (m, 1H), 4.65 (m, 1H), 3.50 (m, 2H), 3.25 (m, 2H), 1.70 (m, 2H). MS (ES): 388 [M+H]$^+$.

Example 48

Compound of Formula (Z): R'=3-CF$_3$, R"=4-(2-methoxyethyl)amino, and R'''=3-Cl

Synthesized according to the same procedure as was used for Example 22 starting from the compounds of Example 17 (0.1 g, 0.3 mmol), 2-methoxyethylamine (0.183 ml, 2.1 mmol) and DMSO (1.2 ml). The reaction was conducted at 130° C. for 20 hrs. Purification was performed by flash chromatography on silica gel with a gradient elution of 45–60% EtOAc/hexanes to yield the title compound as a white solid (0.065 g, 56%).

$^1$H NMR (DMSO) δ 10.54 (s, 1H), 8.45 (s, 1H), 7.44 (s, 1H), 7.38 (d, J=8.3 Hz, 1H), 7.08 (dd, J=8.3, 8.3 Hz, 1H), 6.81 (m, 3H), 6.51 (d, J=8.3 Hz, 1H), 5.48 (m, 1H), 3.49 (t, J=5.4 Hz, 2H), 3.36 (m, 2H), 3.27 (s, 3H). MS (ES): 388 [M+H]$^+$.

Example 49

Compound of Formula (Z): R'=3-CF$_3$, R"=4-(3-methylamino)pyrrolidin-1-yl, and R'''=3-Cl Synthesized according to the same procedure as was used for Example 22 starting from the compounds of Example 17 (0.1 g, 0.3 mmol), 3-methylaminopyrrolidine (0.224 ml, 2.1 mmol) and DMSO (1.2 ml). The reaction was conducted at 100° C. overnight. Purification was performed by flash chromatography on silica gel with a gradient elution of 0–5% NH$_4$OH in 30% MeOH/CH$_2$Cl$_2$ to yield the title compound as a white solid (0.05 g, 40%).

$^1$H NMR (DMSO) δ 10.62 (s, 1H), 8.49 (s, 1H), 7.59 (s, 1H), 7.39 (d, J=8.3 Hz, 1H), 7.08 (dd, J=8.3, 8.3 Hz, 1H), 6.97 (d, J=8.3 Hz, 1H), 6.80 (m, 2H), 6.50 (d, J=8.3 Hz, 1H), 3.1–3.55 (m, 6H), 2.31 (s, 3H), 2.05 (m, 1H), 1.80 (m, 1H). MS (ES): 413 [M+H]$^+$.

Example 50

Compound of Formula (Z): R'=3-CF$_3$, R"=4-propylamino, and R'''=3-Cl

Synthesized according to the same procedure as was used for Example 22 starting from the compounds of Example 17 (0.1 g, 0.3 mmol), propylamine (0.173 ml, 2.1 mmol) and DMSO (1.2 ml). The reaction was conducted at 130° C. overnight. Purification was performed by flash chromatography on silica gel with a gradient elution of 30–35% EtOAc/hexanes to yield the title compound as an oil (0.05 g, 45%).

$^1$H NMR (DMSO) δ 10.51 (s, 1H), 8.43 (s, 1H), 7.43 (s, 1H), 7.36 (d, J=8.3 Hz, 1H), 7.07 (dd, J=8.3, 8.3 Hz, 1H), 6.77 (m, 3H), 6.52 (d, J=8.3 Hz, 1H), 5.64 (m, 1H), 3.15 (m, 2H), 1.53 (m, 2H), 0.87 (t, J=7.4 Hz, 3H). MS (ES): 372 [M+H]$^+$.

Example 51

Compound of Formula (Z): R'=3-CF$_3$, R"=4-(3-amino)pyrrolidin-1-yl, and R'"=3-Cl Synthesized according to the same procedure as was used for Example 22 starting from the compounds of Example 17 (0.1 g, 0.3 mmol), 3-aminopyrrolidine (0.173 ml, 2.1 mmol) and DMSO (1.2 ml). The reaction was conducted at 100° C. for 20 hrs. Purification was performed by flash chromatography on silica gel with a gradient elution of 0–5% NH$_4$OH in 30% MeOH/CH$_2$Cl$_2$ to yield the title compound as a white solid (0.075 g, 63%).

$^1$H NMR (DMSO) δ 10.60 (s, 1H), 8.48 (s, 1H), 7.58 (s, 1H), 7.38 (d, J=8.3 Hz, 1H), 7.08 (dd, J=8.3, 8.3 Hz, 1H), 6.93 (d, J=8.8 Hz, 1H), 6.80 (m, 2H), 6.51 (d, J=8.3 Hz, 1H), 3.50 (m, 3H), 3.28 (m, 3H), 3.04 (m, 1H), 2.03 (m, 1H), 1.70 (m, 1H). MS (ES): 399 [M+H]$^+$.

Example 52

Compound of Formula (Z): R'=3-CF$_3$, R"=4-(3-hydroxy)pyrrolidin-1-yl, and R'"=3-Cl Synthesized according to the same procedure as was used for Example 22 starting from the compounds of Example 17 (0.1 g, 0.3 mmol), 3-pyrrolidinol (0.175 ml, 2.1 mmol) and DMSO (1.2 ml). The reaction was conducted at 100° C. for 20 hrs. Purification was performed by flash chromatography on silica gel with a gradient elution of 60–80% EtOAc/hexanes to yield the title compound as a white solid (0.083 g, 69%).

$^1$H NMR (DMSO-d$_6$): δ 10.60 (s, 1H), 8.48 (s, 1H), 7.58 (s, 1H), 7.38 (d, J=8.3 Hz, 1H), 7.06 (dd, J=8.4, 8.4 Hz, 1H), 6.94 (d, J=9.0 Hz, 1H), 6.80 (m, 2H), 6.51 (d, J=8.3 Hz, 1H), 4.96 (s, 1H), 4.35 (s, 1H, broad), 3.54 (m, 2H), 3.29 (m, 1H), 3.11 (d, J=11.1 Hz, 1H), 1.96 (m, 1H), 1.84 (m, 1H). MS (ES): 400 [M+H]$^+$.

Example 53

Compound of Formula (Z): R'=3-CF$_3$, R"=4-pentylamino, and R'"=3-Cl

Synthesized according to the same procedure as was used for Example 22 starting from the compounds of Example 17 (0.1 g, 0.3 mmol), n-pentylamine (0.243 ml, 2.1 mmol) and DMSO (1.2 ml). The reaction was conducted at 130° C. overnight. Purification was performed by flash chromatography on silica gel with 30% EtOAc/hexanes to yield the title compound as an oil (0.083 g, 69%).

$^1$H NMR (DMSO) δ 10.51 (s, 1H), 8.44 (s, 1H), 7.43 (s, 1H), 7.37 (d, J=8.3 Hz, 1H), 7.07 (dd, J=8.4, 8.4 Hz, 1H), 6.77 (m, 3H), 6.52 (d, J=8.3 Hz, 1H), 4.96 (s, 1H), 3.61 (m, 1H), 3.17 (m, 2H), 1.51 (m, 2H), 1.29 (m, 4H), 0.86 (t, J=6.8 Hz, 3H). MS (ES): 400 [M+H]$^+$.

Example 54

Compound of Formula (Z): R'=3-CF$_3$, R"=4-allylamino, and R'"=3-Cl

Synthesized according to the same procedure as was used for Example 22 starting from the compounds of Example 17 (0.1 g, 0.3 mmol), allylamine (0.158 ml, 2.1 mmol) and DMSO (1.2 ml). The reaction was conducted at 130° C. overnight. Purification was performed by flash chromatography on silica gel with a gradient elution of 30–35% EtOAc/hexanes to yield the title compound as an oil (0.08 g, 72%).

$^1$H NMR (DMSO) δ 10.52 (s, 1H), 8.44 (s, 1H), 7.44 (s, 1H), 7.34 (d, J=8.3 Hz, 1H), 7.07 (dd, J=8.1, 8.1 Hz, 1H), 6.79 (d, J=8.2 Hz, 1H), 6.75 (s, 1H), 6.68 (d, J=9.0 Hz, 1H), 6.52 (d, J=8.3 Hz, 1H), 6.04 (t, J=5.5 Hz, 1H), 5.82 (m, 1H), 5.10 (m, 2H), 3.86 (m, 2H). MS (ES): 370 [M+H]$^+$.

Example 55

Compound of Formula (Z): R'=3-CF$_3$, R"=4-(1,2,3,6-tetrahydro)pyridin-1-yl, and R'"=3-Cl Synthesized according to the same procedure as was used for Example 22 starting from the compounds of Example 17 (0.1 g, 0.3 mmol), 1,2,3,6-tetrahydropyridine (0.192 ml, 2.1 mmol) and DMSO (1.2 ml). The reaction was conducted at 130° C. for 24 hrs. Purification was performed by flash chromatography on silica gel with a gradient elution of 30–35% EtOAc/hexanes to yield the title compound as a white solid (0.035 g, 30%).

$^1$H NMR (DMSO) δ 10.86 (s, 1H), 8.63 (s, 1H), 7.67 (s, 1. H), 7.58 (d, J=8.3 Hz, 1H), 7.07 (dd, J=8.1, 8.1 Hz, 1H), 6.83 (d, J=8.2 Hz, 1H), 6.76 (s, 1H), 6.52 (d, J=8.3 Hz, 1H), 5.80 (m, 2H), 3.42 (m, 2H), 2.99 (m, 2H), 2.18 (m, 2H). MS (ES): 396 [M+H]$^+$.

Example 56

Compound of Formula (Z): R'=3-CF$_3$, R"=4-[(R)-3-trifluoroacetomido]pyrrolidin-1-yl, and R'"=3-Cl Synthesized according to the same procedure as was used for Example 22 starting from the compounds of Example 17 (0.1 g, 0.3 mmol), (3R)-(+)-3-(trifluoroacetamido)pyrrolidine hydrochloride (0.459 g, 2.1 mmol), NEt$_3$ (0.585 ml, 4.2 mmol) and DMSO (2 ml). The reaction was conducted at 100° C. for 18 hrs. Purification was performed by flash chromatography on silica gel with a gradient elution of 40–60% EtOAc/hexanes to give the title compound as a white solid (0.02 g, 13%).

$^1$H NMR (DMSO) δ 10.65 (s, 1H), 9.66 (d, J=6.7 Hz, 1H), 8.51 (s, 1H), 7.61 (s, 1H), 7.43 (d, J=8.3 Hz, 1H), 7.07 (dd, J=8.1, 8.1 Hz, 1H), 7.00 (d, J=8.2 Hz, 1H), 6.80 (m, 2H), 6.51 (d, J=8.3 Hz, 1H), 4.41 (m, 1H), 3.60 (m, 1H), 3.3–3.5 (m, 3H), 2.20 (m, 1H), 2.02 (m, 1H). MS (ES): 495 [M+H]$^+$.

Example 57

Compound of Formula (Z): R'=3-CF$_3$, R"=4-pyrrol-1-yl, and R'"=3-Cl

A sample compound from Example 19 (0.033 g, 0.1 mmol), 2,5-dimethoxytetrahydrofuran (0.065 ml, 0.5 mmol) and HOAc (1 ml) was heated to 70° C. for 45 min. The mixture was allowed to cool to room temperature, poured into sat. NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 30–35% EtOAc/hexanes to give the title compound as an oil (0.03 g, 79%).

$^1$H NMR (DMSO) δ 11.11 (s, 1H), 8.76 (s, 1H), 7.88 (s, 1H), 7.73 (d, J=8.3 Hz, 1H), 7.50 (d, J=8.2 Hz, 1H), 7.11 (dd, J=8.2, 8.2 Hz, 1H), 6.93 (m, 2H), 6.87 (m, 2H), 6.53 (d, J=8.2 Hz, 1H), 6.24 (m, 2H). MS (ES): 380 [M+H]$^+$.

Example 58

Compound of Formula (Z): R'=3-CF$_3$, R"=4-[(R)-3-acetomido]pyrrolidin-1-yl, and R'"=Cl Synthesized according to the same procedure as was used for Example 22 starting from the compounds of Example 17 (0.1 g, 0.3 mmol), 3-(N-acetyl-N-methylamino)pyrrolidine (0.269 g, 2.1 mmol) and DMSO (1.2 ml). The reaction was conducted at 120° C. for 18 hrs. Purification was performed by flash chromatography on silica gel with a gradient elution of 0–10% MeOH/EtOAc to yield the title compound as a white solid (0.103 g, 78%).

$^1$H NMR (DMSO) δ 10.62 (s, 1H), 8.49 (s, 1H), 8.10 (d, J=5.6 Hz, 1H), 7.60 (s, 1H), 7.40 (d, J=8.3 Hz, 1H), 7.07 (dd, J=8.1, 8.1 Hz, 1H), 6.96 (d, J=8.2 Hz, 1H), 6.80 (m, 2H), 6.51 (d, J=8.3 Hz, 1H), 4.27 (m, 1H), 3.55 (m, 1H), 3.44 (m, 1H), 3.35 (m, 1H), 3.15 (m, 1H), 2.10 (m, 1H), 1.83 (m, 1H), 1.80 (s, 1H). MS (ES): 441 [M+H]$^+$.

Example 59

Compound of Formula (Z): R'=3-CF$_3$, R"=4-cyclopropylamino, and R'"=3-Cl

Synthesized according to the same procedure as was used for Example 22 starting from the compounds of Example 17 (0.1 g, 0.3 mmol), cyclopropylamine (0.146 ml, 2.1 mmol) and DMSO (1.2 ml). The reaction was conducted at 120° C. for 2 days. Purification was performed by flash chromatography on silica gel with a gradient elution of 60–80% EtOAc/hexanes to give the title compound as a white solid (0.05 g, 45%).

$^1$H NMR (DMSO) δ 10.56 (s, 1H), 8.46 (s, 1H), 7.44 (m, 2H), 7.60 (s, 1H), 7.16 (d, J=8.3 Hz, 1H), 7.08 (dd, J=8.1, 8.1 Hz, 1H), 6.79 (m, 2H), 6.51 (d, J=8.3 Hz, 1H), 5.99 (s, 1H), 2.42 (m, 1H), 0.75 (m, 2H), 0.50 (m, 2H). MS (ES): 370 [M+H]$^+$.

Example 60

Compound of Formula (Z): R'=3-CF$_3$, R"=4-cyclopentylthio, and R'"=3-Cl

A sample of the compound from Example 17 (0.1 g, 0.3 mmol), cyclopentyl mercaptan (0.225 ml, 2.1 mmol), NaHCO$_3$ (0.14 g) and DMSO (1.2 ml) was heated to 90° C. overnight. The mixture was allowed to cool to room temperature, poured into brine and extracted with EtOAc. The organic layer was separated, washed with brine, dried with anhydrous Na$_2$SO$_4$, concentrated by rotary evaporation and purified by flash chromatography on silica gel with 30% EtOAc/hexanes to yield the title compound as a white solid (0.128 g, 100%).

$^1$H NMR (DMSO) δ 10.93 (s, 1H), 8.67 (s, 1H), 7.70 (s, 1H), 7.63 (d, J=8.3 Hz, 1H), 7.53 (d, J=8.3 Hz, 1H), 7.08 (dd, J=8.1, 8.1 Hz, 1H), 6.83 (d, J=8.2 Hz, 1H), 6.77 (s, 1H), 6.51 (d, J=8.3 Hz, 1H), 3.84 (quint, J=6.3 Hz, 1H), 2.09 (m, 2H), 1.70 (m, 2H), 1.58 (m, 2H), 1.50 (m, 2H). MS (ES): 415 [M+H]$^+$.

Example 61

Compound of Formula (Z): R'=3-CF$_3$, R"=4-isopropylthio, and R'"=3-Cl

Synthesized according to the same procedure used for Example 60 starting from a sample of compound from Example 22 (0.08 g, 0.24 mmol), 2-propanethiol (0.156 ml, 1.68 mmol), NaHCO$_3$ (0.115 g) and DMSO (1 ml). The reaction was conducted at 90° C. overnight. Purification was performed by flash chromatography on silica gel with a gradient elution of 35–40% EtOAc/hexanes to give the title compound as a white solid (0.073 g, 78%).

$^1$H NMR (DMSO) δ 10.95 (s, 1H), 8.70 (s, 1H), 7.72 (s, 1H), 7.66 (d, J=8.3 Hz, 1H), 7.53 (d, J=8.3 Hz, 1H), 7.09 (dd, J=8.1, 8.1 Hz, 1H), 6.84 (d, J=8.2 Hz, 1H), 6.74 (s, 1H), 6.51 (d, J=8.3 Hz, 1H), 3.68 (sept, J=6.3 Hz, 1H), 1.25 (d, J=6.6 Hz, 1H). MS (ES): 389 [M+H]$^+$.

Example 62

Compound of Formula (Z): R'=3-CF$_3$, R"=4-ethylthio, and R'"=3-Cl

Synthesized according to the same procedure used for Example 60 starting from a sample of compound from Example 22 (0.08 g, 0.24 mmol), ethanethiol (0.125 ml, 1.68 mmol), NaHCO$_3$ (0.115 g) and DMSO (1 ml). The reaction was conducted at 90° C. overnight. Purification was performed by flash chromatography on silica gel with a gradient elution of 35–40% EtOAc/hexanes to yield the title compound as a white solid (0.073 g, 78%).

$^1$H NMR (DMSO) δ 10.92 (s, 1H), 8.70 (s, 1H), 7.70 (s, 1H), 7.56 (m, 2H), 7.08 (d, J=8.3 Hz, 1H), 6.82 (d, J=8.1 Hz, 1H), 6.78 (s, 1H), 6.74 (s, 1H), 6.51 (d, J=8.3 Hz, 1H), 3.08 (q, J=7.3 Hz, 2H), 1.23 (dt, J=7.3 Hz, 1H). MS (ES): 375 [M+H]$^+$.

Example 63

Compound of Formula (Z): R'=3-Cl, R"=4-Cl, and R'"=4-F

The title compound was prepared following procedures described for Example 1 except substituting 3,4-dichlorobenzoyl chloride for 3-trifluoromethylbenzoyl chloride and substituting 4-flroroaniline for aniline. $^1$H NMR (CDCl$_3$) δ 7.54 (d, J=2.0 Hz, 1 H), 7.32 (d, J=8.3 Hz, 1 H), 7.14 (dd, J=2.0 Hz, J=8 Hz, 1 H), 6.86 (m, 2 H), 6.67 (m, 2 H). MS (ES+): 299 (M+H, 100).

Example 64

Compound of Formula (Z): R'=3-CF$_3$, R"=4-Cl, and R'"=3-Cl

Step 64a. 4-Chloro-3-trifluoromethylbenzaldehyde (0.315 g, 1.51 mmol, purchased from Aldrich Chemical Co.) and hydroxyamine hydrochloride (0.315 g, 4.53 mmol) were stirred in methanol (5 mL) at 0° C. for 1 h. The reaction mixture was diluted with ethyl acetate and was washed with water and saturated NaCl solution. Organic layer was dried with Na2SO4, filtered and concentrated to give the oxime intermediate.

Step 64b. The oxime was dissolved in DMF(3 mL) and was treated with N-bromosucinimide (0.325 g, 1.83 mmol) at 0° C. The starting oxime reacted completely in one hour, at which time excess 3-chloroaniline (5 equiv.) and triethylamine (3 equiv.) were added. Stir continued at 0° C. overnight. The reaction mixture was diluted with ethyl acetate and was washed with water and saturated NaCl solution. Organic layer was dried over MgSO$_4$, filtered, and concentrated. The crude product was purified by flash chromatography on silica gel eluted with 6:1 to 3:1 hexane/AcOEt to give pure product, 51.5 mg, in 10% yield.

$^1$H (DMSO) δ 11.1 (s, 1H), 8.75 (s, 1H), 7.83 (s, 1H), 7.70 (d, J=8.4 Hz, 1H), 7.63 (d, J=8.4 Hz, 1H), 7.21 (t, J=8.0 Hz, 1H), 6.85 (d, J=8.0 Hz, 1H), 6.82 (s, 1H), 6.50 (d, J=8.0Hz, 1H). MS (ES): 350 [M+H]$^+$.

Example 65

Compound of Formula (Z): R'=3-CF$_3$, R"=4-Cl, and R'"=H

Following procedures described for Example above and substituting 3-chloroaniline with aniline in Step 64b, the title compound was obtained in 11.5% yield.

$^1$H (DMSO) δ 10.9 (s, 1H), 8.5 (s, 1H), 7.77 (s, 1H), 7.67 (d, J=8.4 Hz, 1H), 7.57 (d, J=8.4 Hz, 1H), 7.11 (t, J=7.4 Hz, 2H), 6.83 (t, J=7.4 Hz, 1H), 6.67 (d, J=7.4 Hz, 2H). MS (ES): 315 [M+H]$^+$.

Example 66

Compound of Formula (Z): R'=3-OCF$_2$CHF$_2$, R"=H, and R'"=3-Cl

The title compound was synthesized following procedures described for Example 1 except substituting 3-tetrafluoroethoxybenzoyl chloride for 3-trifluoromethylbenzoyl chloride and substituting 3-chloroaniline for aniline. $^1$H NMR (DMSO) δ 10.9 (s, 1H), 8.66 (s, 1H), 7.47 (t, J=7.8 Hz, 1H), 7.38 (d, J=7.8 Hz, 1H), 7.30 (d, J=7.8 Hz, 1H), 7.24 (s, 1H), 7.07 (t, J=8.0 Hz, 1H), 6.82 (d, J=8.1 Hz, 1H), 6.76 (t, J=55 Hz, 1H), 6.73 (s, 1H), 6.50 (d, J=8.0 Hz, 1H). MS (ES): 363 [M+H]$^+$.

Example 67

Compound of Formula (Z): R'=3-OCF$_2$CHF$_2$, R"=H, and R'"=3-F

The title compound was synthesized following procedures described for Example 1 except substituting 3-tetrafluoroethoxybenzoyl chloride for 3-trifluoromethylbenzoyl chloride and substituting 3-fluroaniline for aniline.

$^1$H NMR (DMSO): δ 10.9 (s, 1H), 8.65 (s, 1H), 7.44 (t, J=8.0 Hz, 1H), 7.38 (d, J=7.6 Hz, 1H), 7.30 (d, J=7.6 Hz, 1H), 7.22 (s, 1H), 7.08 (q, J=7.8 Hz, 1H), 6.75 (t, J=50 Hz, 1H), 6.59 (dd, J=7.8, 7.6 Hz, 1H), 6.45 (d, J=7.8 Hz, 1H), 64.2 (d, J=7.6 Hz, 1H). MS (ES): 347 [M+H]$^+$.

Example 68

Compound of Formula (Z): R'=3-Br, R"=H, and R'"=H

Following procedures described in Example 1 and substituting 3-bromobenzoyl chloride for 3-trifluoromethylbenzoyl chloride the title compound was prepared in 30% yield.

$^1$H (DMSO) δ 10.7 (s, 1H), 8.36 (s, 1H), 7.53 (m, 2H), 7.29 (m, 2H), 7.09 (dd, J=8.0, 8.0 Hz, 2H), 6.81 (dd, J=8.1, 8.1 Hz, 1H), 6.65 (d, J=7.5 Hz, 2H). MS (ES): 291 [M+H]$^+$.

Example 69

Compound of Formula (Z): R'=3-phenyl, R"=H, and R'"=H

General procedures for Suzuki coupling of the compound from Example 68 and the respective boronic acid: To a flask containing aq. K2CO3 (0.4 ml, 2.0 M), EtOH (0.2 ml) and toluene (2 ml) was added a sample of compound of Example 68 (0.136 g, 0.5 mmol), PhB(OH) 2 (0.091 g, 0.75 mmol) and Pd(PPh3)4 (0.115 g, 0.1 mmol). The mixture was stirred for 2 hrs at 1000C under a nitrogen atmosphere. It was then cooled to r.t. and poured into water. The mixture was extracted with EtOAc. The organic layer was separated, washed with brine, dried with anhydrous Na2SO4, concentrated by rotary evaporation and purified by flash chromatography on silica gel with a gradient elution of 25–35% EtOAc/hexanes to yield the title compound as a white solid (0.085 g, 59%). 1H NMR (DMSO) δ 10.58 (s, 1H), 8.34 (s, 1H), 7.63 (d, J=10.0 Hz, 1H), 7.60 (s, 1H), 7.50 (d, J=7.0 Hz, 2H), 7.38 (m, 5H), 7.06 (m, 2H), 6.79 (m, 1H), 6.71 (d, J=7.56, 2 H). MS (ES): 289 [M+H]$^+$.

Example 70

Compound of Formula (Z): R'=3-pyrid-3-yl, R"=H, and R'"=H

Synthesized according to the same procedure used Example 69 starting from a sample of compound of Example 68 (0.136 g, 0.5 mmol), aq. K$_2$CO$_3$ (0.4 ml, 2.0M), pyridine-3-boronic acid (0.092 g, 0.75 mmol) and Pd(PPh$_3$)$_4$ (0.155 g, 0.14 mmol) in EtOH (0.2 ml) and toluene (2 ml). The mixture was stirred overnight under a nitrogen atmosphere at 100° C. Purification was performed by flash chromatography on silica gel with EtOAc as the eluent to yield the title compound as a white solid (0.040 g, 28%).

$^1$H NMR (DMSO) δ 10.61 (s, 1H), 8.70 (s, 1H), 8.55 (d, J=4.4 Hz, 1H), 8.37 (s, 1H), 7.93 (d, J=8.3 Hz, 1H), 7.68 (d, J=7.7 Hz, 1H), 7.64 (s, 1H), 7.43(m, 3H), 7.07 (dd, J=8.3, 8.3 Hz, 2H), 6.79 (dd, J=7.7, 7.7 Hz, 1H), 6.71 (d, J=7.6 Hz, 2H). MS (ES): 290 [M+H]$^+$.

Example 71

Compound of Formula (Z): R'=3-naphthal-2-yl, R"=H, and R'"=H

Synthesized according to the same procedure used Example 69 starting from a sample of compound of Example 68 (0.136 g, 0.5 mmol), aq. K$_2$CO$_3$ (0.4 ml, 2.0M), 2-naphthaleneboronic acid (0.129 g, 0.75 mmol) and Pd(PPh$_3$)$_4$ (0.055 g, 0.05 mmol) in EtOH (0.2 ml) and toluene (2 ml). The mixture was stirred under a nitrogen atmosphere for 1.5 hrs at 100° C. Purification was performed by flash chromatography on silica gel with a gradient elution of 30–45% EtOAc/hexanes to give the title compound as a white solid (0.065 g, 38%).

$^1$H NMR (DMSO) δ 10.60 (s, 1H), 8.38 (s, 1H), 8.04 (s, 1H), 7.95 (m, 3H), 7.76 (m, 2H), 7.70 (d, J=8.4 Hz, 1H), 7.53 (m, 2H), 7.46 (dd, J=7.4, 7.4 Hz, 1H), 7.40 (d, J=7.4 Hz, 1H),7.10 (dd, J=7.6, 7.6 Hz, 2H), 6.80 (dd, J=7.6, 7.6 Hz, 1H), 6.74 (d, J=7.8 Hz, 2H). MS (ES): 339 [M+H]$^+$.

Example 72

Compound of Formula (Z): R'=3-CF$_3$, R"=4-propyn-1-yl, and R'"=3-Cl

Step 72a. The N-3-chlorophenyl 4-azido-3-trifluoromethylbenzamide compound from Step 18c was reduced under 1 atm of hydrogen in the presence of Pd/ in ethanol to the give the corresponding 4-aminobenzamide, which was used without purification in Step 72b.

Step72b. 4-Amino-N-(3-chlorophenyl)-3-trifluoromethylbenzamide (5.25 g, 16.7 mmol) was suspended in a solution of methanol/water 1:1 (400 mL) and cooled to –10° C. Next, concentrated HCl (20 mL) was added followed by a dropwise addition of an aqueous solution of NaNO$_2$(1.50 g, 21.7 mmol). After stirring for 45 min. at –10° C., an aqueous solution of sodium iodide (3.51 g, 23.4 mmol) was added dropwise, and the solution was allowed to slowly warm to room temperature over a period of 2 h. The dark solution was then extracted with ether, washed with a saturated solution of Na$_2$S$_2$O$_3$, brine, and dried over Na$_2$SO$_4$. Excess solvent was removed using reduced pressure, and the remaining material was purified using flash chromatography (silica) eluting with a 4:1 solution of hexane and ethyl actetate. Similar fractions were pooled and concentrated to give 3.2 g (45%) of corresponding 4-iodo product (off-white solid). MS (ES+): 426 (M+H, 100).

Step 72c. A general procedure for the Negishi cross coupling. Under an atmosphere of nitrogen, a THF solution of zinc bromide (10 eq.) was added dropwise to a solution of Grignard reagent (10 eq.) at room temperature. After stirring for 2 h, the aryl iodide (1 eq.) from Step 72c was added followed by the addition of (Dppf)$_2$PdCl$_2$ (0.05 eq.). The solution was then allowed to stir overnight at room temperature. The reaction was quenched with a saturated sol of NH$_4$Cl, and the resulting mixture was extracted with ether, washed with brine, and dried over Na$_2$SO$_4$. Excess solvent was removed using reduced pressure, and the resulting residue was purified on silica eluting with a 20% ethyl acetate/hexane solution. Starting with propynyl Grignard the title compound was obtained.

$^1$H NMR (CDCl$_3$) δ 8.59 (s, 1 H), 7.74 (s, 1 H), 7.41 (m, 2 H), 7.19 (s, 1 H), 7.01 (t, J=8 Hz, 1 H), 6.92 (m, 1 H), 6.73 (t, J=2 Hz, 1 H), 6.43 (m1 H), 2.08 (s, 3H). MS (ES+): 353(M+H, 100).

Example 73

Compound of Formula (Z): R'=3-CF$_3$, R"=4-vinyl, and R'"=3-Cl

The title compound was prepared following conditions of Step 72c of Example 72 except using vinyl Grignard.

$^1$H NMR (CDCl$_3$) δ 7.73 (d, J=6.2 Hz, 1 H), 7.53–7.64 (m, 1 H), 7.42–7.49 (m, 1 H), 7.02 (m, 2 H), 6.94 (m, 1 H), 6.75 (dt, J=2.1 Hz, J=18.4 Hz, 1H), 6.46 (m, 1 H), 5.78 (d, J=17.3 Hz, 1 H), 5.45 (d, J=11.5 Hz, 1 H). MS (ES+): 341 (M+H, 100).

Example 74

Compound of Formula (Z): R'=3-CF$_3$, R"=4-(2-methyl)prop-1-enyl, and R'"=3-Cl

The title compound was prepared following conditions of Step 72c of Example 72 except using 2-methylbutenyl Grignard.

$^1$H NMR (CDCl$_3$) δ 7.75 (s, 1 H), 7.43 (d, J=8 Hz, 1 H), 7.26 (s, 1 H), 7.20 (d, J=8.0 Hz, 1 H), 7.02 (t, J=8.0 Hz, 1 H), 6.91 (m, 1 H), 6.69 (t, J=2.0 Hz, 1 H), 6.48 (m, 1 H), 6.37 (s, 1 H). MS (ES+): 369 (M+H, 100).

Example 75

Compound of Formula (Z): R'=3-CF$_3$, R"=4-isobutyl, and R'"=3-Cl

A sample of the compound from Example 74 was hydrogenated under 1 atm of H$_2$ and in the presence of Pd/C to give the title compound.

$^1$H NMR (CDCl$_3$) δ 7.73 (d, J=1.4 Hz, 1 H), 7.41 (dd, J=1.4Hz, J=8.0 Hz, 1 H), 7.23 (d, J=7.9 Hz, 1 H), 7.01 (t, J=8.0 Hz, 1 H), 6.91 (dm, J=8 Hz, 1 H), 6.66 (t, J=2.0 Hz, 1 H), 6.47 (dm, J=8.1 Hz, 1 H), 2.63 (d, J=7.3 Hz, 2 H), 1.92 (qn, J=6.8 Hz, 1 H), 0.88 (d, J=6.6 Hz, 6 H). MS (ES+): 371 (M+H, 100).

Example 76

Compound of Formula (Z): R'=3-CF$_3$, R"=4-allyl, and R'"=3-Cl

The title compound was prepared following conditions of Step 72c of Example 72 and using allyl Grignard.

$^1$H NMR (CDCl$_3$) δ 7.72 (s, 1 H), 7.44 (d, J=7.5 Hz, 1 H), 7.33 (s, 1 H), 7.28 (d, J=8 Hz, 1 H), 7.04 (t, J=8.0 Hz, 1 H), 6.95 (dm, J=8.0 Hz, 1 H), 6.73 (t, J=2.0 Hz, 1 H), 6.49 (dm, J=8.0 Hz), 5.89 (m, 1 H), 5.11 (dd, J=1.4 Hz, J=10 Hz, 1 H), 5.02 (dd, J=1.5 Hz, J=17 Hz, 1 H), 3.53 (d, J=6.3 Hz, 2 H). MS (ES+): 355 (M+H, 100).

Example 77

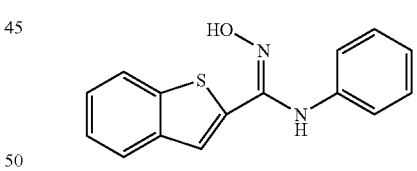

77

Benzothiophene-2-carboxylic acid was treated with 1.5 equivalents of oxalyl chloride in dichloromethane in the presence of a catalytic amount of DMF to form benzothiophene-2-carbonyl chloride. Following procedures described for Example 1 and substituting this acyl chloride for 3-trifluoromethylbenzoyl chloride, compound 77 was prepared in 23% yield.

$^1$H NMR (DMSO) δ 10.94 (s, 1H), 8.41 (s, 1H), 7.91 (d, J=8.4 Hz, 1H), 7.74 (d, J=8.6 Hz, 1H), 7.34 (m, 2H), 7.29 (s, 1H), 7.14 (t, J=7.2 Hz, 1H), 6.82 (m, 3H). MS (ES+): 269 (M+H), MS (ES–): 267 (M–H). Anal. Calcd. for C$_{15}$H$_{12}$N$_2$OS: C, 67.14; H, 4.51; N, 10.44; S, 11.95. Found: C, 65.83; H, 4.51; N, 10.15; S, 11.67.

Example 78

Compound 78 was synthesized in a manner similar to compound 77.

¹H NMR (CDCl₃) δ 9.17 (s, 1 H), 7.63 (d, J=1.8 Hz, 1 H) 7.36 (s, 1 H), (dd, J=1.5 Hz, J=6.5 Hz, 1 H), 7.05 (t, J=8 Hz, 2 H), 6.94 (t, J 8 Hz, 2 H), 6.62 (d, J=7.5 Hz, 2 H), MS (ES+): 366(M+H, 100).

Example 79

Compound 79 was synthesized in a manner similar to compound 77.

¹H NMR (CDCl₃) δ 9.24 (s, 1 H), 7.64 (s, 1 H), 7.24 (m, 2 H), 7.02 (d, J=8.7 Hz,1 H), 6.95 (t, J=8.0 Hz, 1 H), 6.89 (dm, J=8.0 Hz, 1 H),6.75 (s, 1 H), 6.46 (dm, J=7.9 Hz, 1 H). MS (ES+): 400 (M+H, 100).

Example 80

Compound 80 was synthesized in a manner similar to compound 77.

¹H NMR (CDCl₃) δ 7.61(d, J=2.0 Hz, 1 H), 7.37 (dd, J=2.0 Hz, J=8.5 Hz, 1 H), 7.20–7.28 (m, 3 H), 7.05 (t, J=7.0 Hz, 1 H), 6.86 (d, J=7.6 Hz, 2 H), 6.60 (d, J=3.6 Hz, 1 H), 6.57 (d, J=3.6 Hz, 1 H). MS (ES+): 358 (M+H, 100).

Example 81

Compound 81 was synthesized in a manner similar to compound 77.

¹H NMR (DMSO) δ 10.7 (s, 1H), 8.59 (s, 1H), 8.56 (s, 1H), 7.75 (d, J=8.8 Hz, 2H), 7.65 (d, J=8.8 Hz, 2H), 6.95 (t, J=8.5 Hz, 2H), 6.75 (t, J=8.5 Hz, 1H), 6.52 (d, J=8.5 Hz, 2H), 1.72 (s, 3H). MS (ES+): 343 (M+H, 100).

Example 82

Compound 82 was synthesized in a manner similar to compound 77.

¹H NMR (DMSO) δ 10.6 (s, 1H), 8.38 (s, 1H), 7.97 (s, 1H), 7.88 (d, J=8.3 Hz, 2H), 7.83 (d, J=8.6 Hz, 1H), 7.51 (m, 2H), 7.45 (d, J=8.5 Hz, 1H), 7.02 (t, J=8.0 Hz, 2H), 6.75 (t, J=7.8 Hz, 1H), 6.68 (d, J=7.6 Hz, 2H). MS (ES+): 263 (M+H), MS (ES−): 261 (M−H). Anal. Calcd. for C₁₇H₄₁N₂O: C, 77.84; H, 5.38; N, 10.68. Found: C, 77.73; H, 5.68; N, 10.19.

Example 83

Compound 83 was synthesized in a manner similar to compound 77.

¹H NMR (DMSO) δ 10.8 (s, 1H), 8.82 (s, 1H), 7.97 (d, J=8.0 Hz, 1H), 7.77 (d, J=8.4 Hz, 1H), 7.60 (t, J=8.4 Hz, 1H), 7.06 (t, J=7.7 Hz, 1H), 6.80 (t, J=7.7 Hz, 1H), 6.70 (d, J=7.7 Hz, 2H). MS (ES+): 263 [M+H]⁺.

Example 84

Compound 84 was synthesized in a manner similar to compound 77.

¹H NMR (DMSO) δ 10.7 (s, 1H), 8.30 (s, 1H), 7.88 (s, 1H), 7.85 (d, J=7.5 Hz, 1H), 7.65 (t, J=7.5 Hz, 1H), 7.63 (d, J=7.5 Hz, 1H), 7.58 (d, J=7.5 Hz, 1H), 7.20 (t, J=7.2 Hz, 1H), 7.08 (d, J=17 Hz, 1H), 6.95 (s, 1H), 6.85 (d, J=17 Hz, 1H), 6.81 (d, J=7.2 Hz, 1H).

Example 85

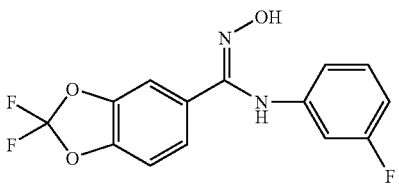

Compound 85 was synthesized in a manner similar to compound 77.

$^1$H NMR (DMSO) δ $^1$H NMR (DMSO) δ 10.8 (s, 1H), 8.63 (s, 1H), 7.42 (s, 1H), 7.38 (d, J=8.4 Hz, 1H), 7.21 (d, J=8.4 Hz, 1H), 7.08 (q, J=7.8 Hz, 1H), 6.59 (t, J=7.5 Hz, 1H), 6.50 (d, J=11.2 Hz, 1H), 6.38 (d, J=7.8 Hz, 1H). MS (ES+): 311 [M+H]$^+$.

Example 86

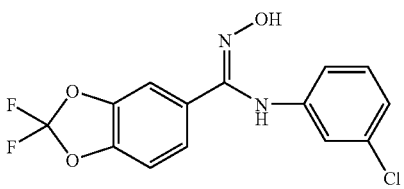

Compound 86 was synthesized in a manner similar to compound 77.

$^1$H NMR (DMSO) δ $^1$H NMR (DMSO) δ 10.9 (s, 1H), 8.63 (s, 1H), 7.43 (s, 1H), 7.39 (d, J=8.4 Hz, 1H), 7.21 (d, J=8.4 Hz, 1H), 7.05 (t, J=8.0 Hz, 1H), 6.83 (d, J=8.0 Hz, 1H), 6.80 (s, 1H), 6.48 (d, J=8.0 Hz, 1H). MS (ES+): 327 [M+H]$^+$.

Example 87

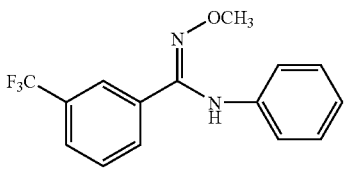

The title compound was prepared in 76% yield following methods developed for Example 1 except substituting methoxyamine hydrochloride for hydroxyamine hydrochloride in Step 1b.

$^1$H NMR (DMSO) δ 8.70 (s, 1H), 7.71 (d, J=8.0 Hz, 1H), 7.64 (s, 1H), 7.58 (d, J=8.0 Hz, 1H), 7.54 (t, J=8.0 Hz, 1H), 7.09 (t, J=7.5 Hz, 2H), 6.85 (t, J=7.5 Hz, 1H), 6.68 (t, J=7.5 Hz, 2H), 3.87 (s, 3H). MS (ES+): 295 [M+H]$^+$.

Example 88

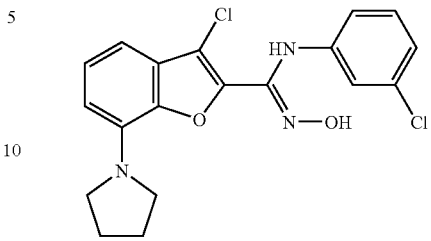

Step 88a. To a dichloroethane solution of 7-pyrrolidin-1-yl-benzofaran-2-carboxylic acid (3-chloro-phenyl)-amide (343 mg, 1 μM) was added phosphorous pentachloride (210 mg, 1.2 mmol), and the mixture was stirred at 75° C. for 2 hours. The solvent was removed under vacuum, the mixture was treated with 5 ml of toluene and then was evaporated to dryness under vacuum. The residue was dissolved in acetonitrile and was added to another flask containing 210 mg (3 mmol) hydroxylamine hydrochloride and triethyl amine 701 μL (5 mmol) in acetonitrile at 0° C. The mixture was allowed to stir overnight. The reaction mixture was diluted with ethyl acetate, washed with 1 N HCl (2×) and brine. The organic layer was dried over MgSO$_4$, filtered and stripped. The crude product was purified by flash chromatography on silica gel eluted with hexane/ethyl acetate (20:1) to give 43 mg of 3-chloro-N-(3-chloro-phenyl)-N'-hydroxy-7-pyrrolidin-1-yl-benzofuran-2-carboxamidine in 13% yield.

$^1$H NMR (CDCl$_3$) δ 7.24 (d, J=8.9Hz, 1H), 7.09 (d, J=8.1 Hz, 1H), 7.05 (d, J=8.0 Hz, 1H), 7.00 (s, 1H), 6.89 (d, J=8.1 Hz, 1H), 6.85 (s, 1H), 6.66 (d, J=8.0 Hz, 1H), 3.31 (s, 4H), 1.97 (s, 4H). MS (ES+): 390 (M+H, 100).

Example 89

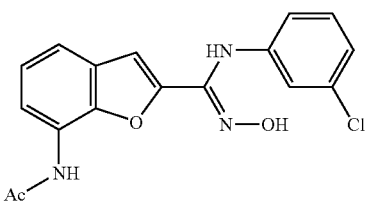

Step 89a: To a solution of N-(3-chloro-phenyl)-N'-hydroxy -5-bromo-7-nitro-benzofuran-2-carboxamidine 2.0 g (4.9 mmol) and 1.8 ml of dihydropyran (9.8 mmol) in 10 mL of dichloromethane at room temperature with stirring under N$_2$ was added 113 mg (0.245 mmol) of camphorsonic acid. The resulting solution was stirred at room temperature for 2 h followed by addition of 34 μL of triethyl amine: The resulting residue was diluted with ethyl acetate, washed with 1 N HCl (2×), saturate sodium bicarbonate solution and brine. The organic layer was dried over MgSO$_4$, filtered and stripped. The crude product was purified by flash chromatography on silica gel eluted with 5–10% methanol/dichloromethane to give 2.2 g of 3-chloro-N-(3-chloro-phenyl)-hydroxy-5-bromo-7-nitro-N-(tetrahydro-pyran-2-yloxy)-benzofuran-2-carboxamidine in 91% yield.

Step 89b: To a methanol solution of N-(3-chloro-phenyl)-hydroxy-5-bromo-7-nitro-N-(tetrahydro-pyran-2-yloxy)-benzofuran-2-carboxamidine was added 200 mg of Pd/C.

The resulted solution was stirred under 1 atm of hydrogen for 2 h. The Pd/C was filtered off through a celite pad and the organic solution was concentrated under vacuum. The product was used for next reaction directly without further purification.

Step 89c: To a dichloromethane solution of 42 mg of N-(3-chloro-phenyl)-hydroxy-7-amino-N-(tetrahydro-pyran-2-yloxy)- benzofuran-2-carboxamidine was 200 µl of pyridine and 200 µl of acetic anhydride. The resulted solution was stirred at room temperature for 20 min. The reaction mixture was concentrated under vacuum. The crude product was purified by flash chromatography on silica gel eluted with 5–10% methanol/dichloromethane to give 43 mg of N-{2-[N-(3-chloro-phenyl)-N-(tetrahydro-pyran-2-yloxy)-carbamimidoyl]-benzofuran-7-yl}-acetamide in 99% yield.

Step 89d: To a methanol solution of N-{2-[N-(3-chloro-phenyl)-N-(tetrahydro-pyran-2-yloxy)-carbamimidoyl]-benzofuran-7-yl}-acetamide was added 200 mg of acidic Dowex resin. The resulted solution was stirred at reflux temperature for 1 h. The reaction mixture was filtered and concentrated under vacuum. The crude product was purified using a chromatotron and eluting with hexane/ethyl acetate (8:2) to give 25 mg N-{2-[N-(3-chloro-phenyl)-N'-hydroxy-carbamimidoyl]-benzofuran-7-yl}-acetamide in 73% yield.

$^1$H NMR (CD$_3$OD) δ 7.85 (dd, J1=2.1 Hz, J2=8.0 Hz, 2H), 7.29 (d, J=8.9 Hz, 1H), 7.21 (dd, J1=8.1 Hz, J2=2.0 Hz, 1H), 7.04 (t, J=8.0 Hz, 1H), 6.93 (d, J= 8.1 Hz, 1H), 6.86 (t, J=2.1 Hz, 1H), 6.67 (d, J1=8.0 Hz, J2=2.0 Hz, 1H), 2.16 (s, 3H). MS (ES+): 344 (M+H, 100).

Example 90

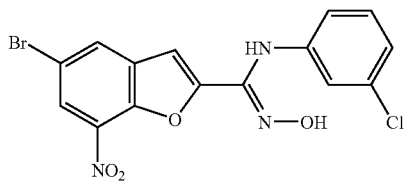

Following the procedures described for Example 88, substituting 5-bromo-7-nitro-benzofuran-2-carboxylic acid (3-chloro-phenyl)-amide for 7-pyrrolidin-1-yl-benzofuran-2-carboxylic acid (3-chloro-phenyl)-amide, the corresponding N-(3-chloro-phenyl)-N'-hydroxy -5-bromo-7-nitro-benzofuran-2-carboxamidine was obtained, 46 mg in 46% yield.

$^1$H NMR (CDCl$_3$) δ 8.40 (d, J=2.1 Hz, 1H), 8.36 (d, J=2.1 Hz, 1H), 7.66 (m, 1H), 7.52 (m, 1H), 7.07 (d, J=8.8 Hz, 1H), 6.99 (s, 1H), 6.95 (dm, J=8.2 Hz, 1H), 6.88 (d, J=2.1 Hz, 1H), 6.66 (dm, J=8.0 Hz, 1H). MS (ES+): 410 (M+H, 100).

Example 91

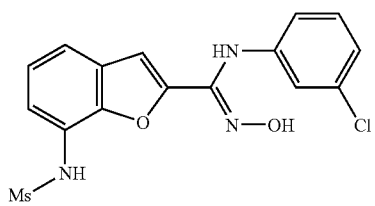

Following the procedures described for Example 89, substituting methanesulfonyl chloride for acetic anhydride in Step 89c, the corresponding N-(3-chloro-phenyl)-N'-hydroxy-7-methanesulfonylamino-benzofuran-2-carboxamidine was obtained, 32 mg, 76.0% yield.

$^1$H NMR (CDCl$_3$) δ 8.11 (bs, 1H), 7.26 (m, 1H), 7.13(s, 1H), 7.07 (t, J=6.9 Hz, 1H), 6.98 (d, J=6.9 Hz, 1H), 6.88 (t, J=1.9 Hz, 1H), 6.60 (dd, J1=2.1 Hz, J2=8.0 Hz, 1H), 6.65 (s, 3H). MS (ES+): 380 (M+H, 100).

Example 92

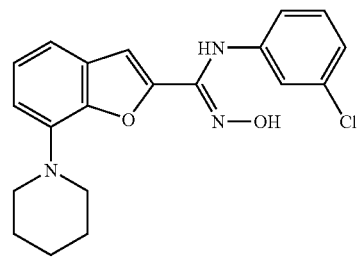

Following the procedures described for Example 88, substituting 7-piperidin-1-yl-benzofuran-2-carboxylic acid (3-chloro-phenyl)-amide for 7-pyrrolidin-1-yl-benzofuran-2-carboxylic acid (3-chloro-phenyl)-amide in Example 88, the N-(3-Chloro-phenyl)-N'-hydroxy-7-piperidin-1-yl-benzofuran-2-carboxamidine was obtained, 52 mg, 28.0% yield.

$^1$H NMR (CDCl$_3$) δ 7.29 (d, J=7.4 Hz, 1H), 7.24 (m, 1H), 7.07 (m, 3H), 6.98 (d, J=7.4 Hz, 1H), 6.91(t, J=1.8 Hz, 1H), 6.82 (s, 1H), 6.66 (dm, J=7.3 Hz, 1H), 3.10 (m, 4H), 1.74 (m, 4H), 1.57 (m, 2H). MS (ES+): 370(M+H, 100).

Example 93

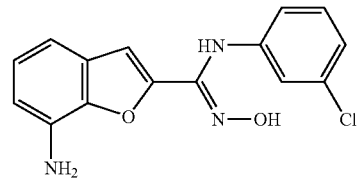

To a methanol solution of 32 mg of N-(3-chloro-phenyl)-hydroxy-7-amino-N-(tetrahydro-pyran-2-yloxy)-benzofuran-2-carboxamidine was 200 mg of acidic Dowex resin. The resulted solution was stirred at reflux temperature for 1 h. The reaction mixture was filtered and concentrated under vacuum. The crude product was purified using a chromatotron and eluting with 5–10% methanol/dichloromethane to give 18 mg of 7-amino-N-(3-chloro-phenyl)-N'-hydroxy-benzofuran-2-carboxamidine in 62% yield.

$^1$H NMR (CDCl$_3$) δ 7.98 (s, 1H), 7.54 (d, J=8.0 Hz, 1H), 7.46 (m, 2H), 7.38 (d, J=8.0 Hz, 1H), 7.33 (m, 1H), 7.04 (t, J=8.2 Hz, 1H), 6.93 (d, J=8.0 Hz, 1H), 6.82 (s, 1H), 6.60 (dm, J=7.9 Hz, 4H). MS (ES+): 302(M+H, 100).

Example 94

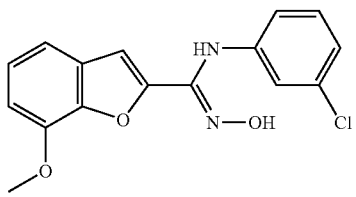

Following the procedures described for Example 88, substituting 7-methoxy-benzofuran-2-carboxylic acid (3-chloro-phenyl)-amide for 7-pyrrolidin-1-yl-benzofuran-2-carboxylic acid (3-chloro-phenyl)-amide in Example 88, N-(3-chloro-phenyl)-N'-hydroxy-7-methoxy-benzofiiran-2-carboxamidine was obtained 152 mg, 32% yield.

$^1$H NMR (CDCl$_3$) δ 7.16 (m, 2H), 7.04 (d, J=7.2 Hz, 1H), 6.92 (d, J=7.2 Hz, 1H), 6.89 (d, J=2.0 Hz, 1H), 6.82 (s, 1H), 6.80 (t, J=6.2 Hz, 1H), 6.68 (dm, J=7.0 Hz, 1H), 3.90 (s, 3H). MS (ES+): 317(M+H, 100).

Example 95

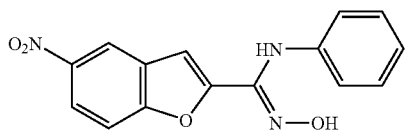

Following the procedures described for Example 88, substituting 5-nitro-benzofuran-2-carboxylic acid phenylamide for 7-pyrrolidin-1-yl-benzofuran-2-carboxylic acid (3-chloro-phenyl)-amide in Example 88 N-hydroxy-5-nitro-N'-phenyl-benzofuran-2-carboxamidine was obtained 36 mg, 27% yield.

$^1$H NMR (CDCl$_3$) δ 8.47 (d, J=2.0 Hz, 1H), 8.23 (d, J1=7.6 Hz, J2=2.4 Hz, 1H), 7.51 (d, J=9.2 Hz, 1H), 7.21 (d, J=8.0 Hz, 1H), 7.09 (d, J=7.6 Hz, 1H), 6.90 (d, J=8.7 Hz, 1H), 6.89 (s, 1H). MS (ES+): 298(M+H, 100).

Example 96

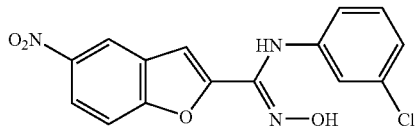

Following the procedures described for Example 88, substituting 5-nitro-benzofuran-2-carboxylic acid (3-chloro-phenyl)-amide for 7-pyrrolidin-1-yl-benzofuran-2-carboxylic acid (3-chloro-phenyl)-amide in Example 88, N-(3-Chloro-phenyl)-N'-hydroxy-5-nitro-benzofuran-2-carboxamidine was obtained 45 mg, 48% yield.

$^1$H NMR (CDCl$_3$) δ 8.48 (d, J=2.0 Hz, 1H), 8.24 (dd, J1=8.0 Hz, J2=2.0 Hz, 1H), 7.51 (d, J=8.8 Hz, 1H), 7.09 (d, J=7.6 Hz, 1H), 6.98 (dm, J=7.2 Hz, 1H), 6.91 (t, J=2.1 Hz, 1H), 6.89 (s, 1H), 6.67 (dm, J=8.0 Hz, 1H). MS (ES+): 331 (M+H, 100).

Example 97

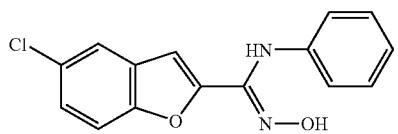

Following the procedures described for Example 88, substituting 5-chloro-benzofuran-2-carboxylic acid phenylamide for 7-pyrrolidin-1-yl-benzofuran-2-carboxylic acid (3-chloro-phenyl)-amide in Example 88 N-hydroxy-5-chloro-N'-phenyl-benzofuran-2-carboxamidine was obtained 52 mg, 42% yield.

$^1$H NMR (CDCl$_3$) δ 7.50 (d, J=2.0 Hz, 1H), 7.34 (d, J=8.4 Hz, 1H), 7.25 (dd, J1=7.6 Hz, J2=2.0 Hz, 1H), 7.21 (t, J=7.6 Hz, 2H), 7.10 (bs, 1H), 7.05 (t, J=7.8 Hz, 1H), 6.87 (dm, J=8.0 Hz, 1H), 6.74 (s, 1H). MS (ES+): 287 (M+H, 100).

Example 98

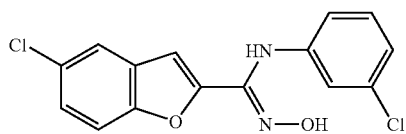

Following the procedures described for Example 88, substituting 5-chloro-benzofuran-2-carboxylic acid (3-chloro-phenyl)-amide for 7-pyrrolidin-1-yl-benzofuran-2-carboxylic acid (3-chloro-phenyl)-amide in Example 88, N-(3-Chloro-phenyl)-N'-hydroxy-5-chloro-benzofuran-2-carboxamidine was obtained 64 mg, 52% yield.

$^1$H NMR (CDCl$_3$) δ 7.53 (d, J=2.0 Hz, 1H), 7.34 (d, J=8.8 Hz, 1H), 7.27 (dd, J1=8.2 Hz, J2=2.4 Hz, 1H), 7.09 (t, J=8.0 Hz, 2H), 6.98 (dm, J=7.2 Hz, 1H), 6.90 (t, J=2.0 Hz, 1H), 6.83 (s, 1H), 6.67 (dm, J=7.2 Hz, 1H). MS (ES+): 321 (M+H, 100).

Example 99

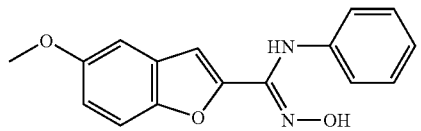

Following the procedures described for Example 88, substituting 5-methoxy-benzofuran-2-carboxylic acid phenylamide for 7-pyrrolidin-1-yl-benzofuran-2-carboxylic acid (3-chloro-phenyl)-amide in Example 88 N-hydroxy-5-methoxy-N'-phenyl-benzofuran-2-carboxamidine was obtained 36 mg, 43% yield.

$^1$H NMR (CDCl$_3$) δ 7.30 (d, J=9.0 Hz, 1H), 7.20 (t, J=8.0 Hz, 2H), 7.03 (t, J=7.6 Hz, 1H), 6.98 (d, J=2.8 Hz, 1H), 6.91 (dd, J1=8.9 Hz, J2=2.4Hz, 1H), 6.87 (d, J=6.8 Hz, 2H), 6.78 (d, J=2.0 Hz, 1H), 3.82 (s, 3H). MS (ES+): 283 (M+H, 100).

Example 100

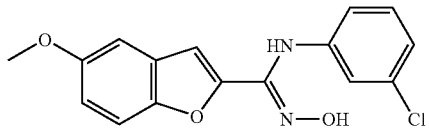

Following the procedures described for Example 88, substituting 5-methoxy-benzofuran-2-carboxylic acid (3-chloro-phenyl)-amide for 7-pyrrolidin-1-yl-benzofuran-2-carboxylic acid (3-chloro-phenyl)-amide in Example 88, N-(3-Chloro-phenyl)-N'-hydroxy-5-methoxy-benzofuran-2-carboxamidine was obtained 51 mg, 34% yield.

$^1$H NMR (CDCl$_3$) δ 7.30 (d, J=8.9 Hz, 1H), 7.27 (bs, 1H), 7.06 (t, J=8.0 Hz, 1H), 6.98 (dm, J=7.6 Hz, 1H), 6.93 (dd, J1=9.2 Hz, J2=2.8 Hz, 1H), 6.89 (t, J=2.0 Hz, 2H), 6.86 (s, 1H), 6.65 (dm, J=7.6 Hz, 1H), 3.82 (s, 3H). MS (ES+): 317 (M+H, 100).

Example 101

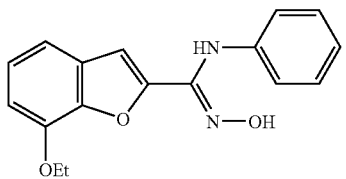

Following the procedures described for Example 88, substituting 7-ethoxy-benzofuran-2-carboxylic acid phenylamide for 7-pyrrolidin-1-yl-benzofuran-2-carboxylic acid (3-chloro-phenyl)-amide in Example 88, N-hydroxy-7-ethoxy-N'-phenyl-benzofuran-2-carboxamidine was obtained 43 mg, 42% yield.

$^1$H NMR (CDCl$_3$) δ 7.19 (t, J=8.0 Hz, 2H), 7.13 (s, 1H), 7.11 (d, J=2.0 Hz, 1H), 7.02 (t, J=8.0 Hz, 1H), 6.89 (d, J=8.0 Hz, 1H), 6.83 (s, 1H), 6.82 (dd, J1=3.6 Hz, J2=5.6 Hz, 1H), 4.09 (q, J=6.8 Hz, 2H), 1.34 (t, J=6.8 Hz, 1H). MS (ES+): 297 (M+H, 100).

Example 102

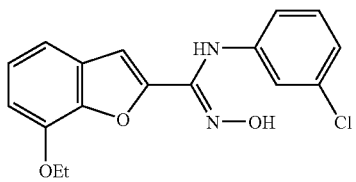

Following the procedures described for Example 88, substituting 5-ethoxy-benzofuran-2-carboxylic acid (3-chloro-phenyl)-amide for 7-pyrrolidin-1-yl-benzofuran-2-carboxylic acid (3-chloro-phenyl)-amide in Example 88, N-(3-Chloro-phenyl)-N'-hydroxy-5-ethoxy-benzofuran-2-carboxamidine was obtained (54 mg, 45% yield).

$^1$H NMR (CDCl$_3$) δ 7.15 (s, 1H), 7.14 (d, J=8.0 Hz, 2H), 7.07 (t, J=8.0 Hz, 2H), 6.98 (dm, J=8.0 Hz, 1H), 6.92 (t, J=2.0 Hz, 1H), 6.90 (s, 1H), 6.84 (dd, J1=6.0 Hz, J2=2.4 Hz, 1H), 6.89 (dm, J=8.0 Hz, 1H), 4.11 (q, J=6.8 Hz, 2H), 1.36 (t, J=6.8 Hz, 1H). MS (ES+): 331 (M+H, 100).

Example 103

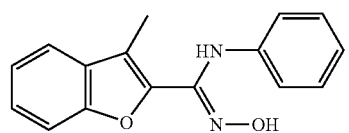

Following the procedures described for Example 88, substituting 3-methyl-benzofuran-2-carboxylic acid phenylamide for 7-pyrrolidin-1-yl-benzofuran-2-carboxylic acid (3-chloro-phenyl)-amide in Example 88, N-hydroxy-3-methyl-N'-phenyl-benzofuran-2-carboxamidine was obtained (2 mg, 57% yield).

$^1$H NMR (CDCl$_3$) δ 7.53 (d, J=7.8 Hz, 1H) 7.37 (d, J=7.6 Hz, 1H), 7.31 (dt, J1=6.8 Hz, J2=1.2 Hz, 1H), 7.27 (dt, J1=7.6 Hz, J2=1.2 Hz, 1H), 7.12 (t, J=8.4 Hz, 2H), 6.95 (t, J=7.2 Hz, 1H), 6.73 (d, J=7.6 Hz, 2H), 2.29 (s, 3H). MS (ES+): 267 (M+H, 100).

Example 104

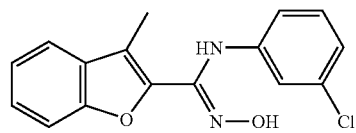

Following the procedures described for Example 88, substituting 3-methyl-benzofuran-2-carboxylic acid (3-chloro-phenyl)-amide for 7-pyrrolidin-1-yl-benzofuran-2-carboxylic acid (3-chloro-phenyl)-amide in Example 88, N-(3-Chloro-phenyl)-N'-hydroxy-3-methyl-benzofuran-2-carboxamidine was obtained (62 mg, 54% yield).

$^1$H NMR (CDCl$_3$) δ 7.55 dm, J=8.0 Hz, 1H), 7.38 (d, J=7.6 Hz, 1H), 7.33 (t, J=7.8 Hz, 1H), 7.27 (dt, J1=7.6 Hz, J2=1.2 Hz, 1H), 7.00 (t, J=8.0 Hz, 1H), 6.92 (dm, J=8.2 Hz, 1H), 6.81 (t, J=2.0 Hz, 1H), 6.53 (dm, J=7.6 Hz, 1H), 2.32 (s, 3H). MS (ES+): 301 (M+H, 100).

Example 105

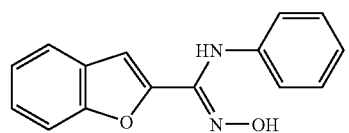

Following the procedures described for Example 88, substituting benzofuran-2-carboxylic acid phenylamide for 7-pyrrolidin-1-yl-benzofuran-2-carboxylic acid (3-chloro-phenyl)-amide in Example 88 N-hydroxy-N'-phenyl-benzofuran-2-carboxamidine was obtained (125 mg, 40% yield).

$^1$H NMR (CDCl$_3$) δ 7.55 (d, J=7.6 Hz, 1H), 7.42 (d, J=8.0 Hz, 2H), 7.31 (t, J=8.0 Hz, 1H), 7.24 (s, 1H), 7.21 (m, 1H), 7.17 (d, J=8.0 Hz, 2H), 7.03 (t, J=7.2 Hz, 1H), 6.87 (m, 3H). MS (ES+): 253 (M+H, 100).

Example 106

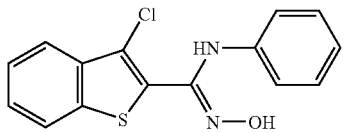

Following the procedures described for Example 88, substituting 3-chloro-benzo[b]thiophene-2-carboxylic acid phenylamidefor 7-pyrrolidin-1-yl-benzofuran-2-carboxylic acid (3-chloro-phenyl)-amide in Example 88, 3-chloro-N-hydroxy-N'-phenyl-benzo[b]thiophene-2-carboxamidine was obtained (162 mg, 62% yield).

$^1$H NMR (CDCl$_3$) δ 7.78 (m, 2H), 7.43 (m, 3H), 7.12 (t, J=7.8 Hz, 2H), 6.95 (t, J=7.8 Hz, 1H), 6.81 (d, J=7.8 Hz, 2H). MS (ES+): 303 (M+H, 100).

Example 107

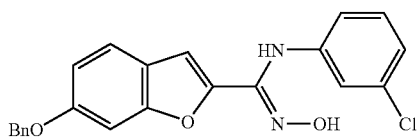

Following the procedures described for Example 88, substituting 6-benzyloxy-benzofuran-2-carboxylic acid (3-chloro-phenyl)-amide for 7-pyrrolidin-1-yl-benzofuran-2-carboxylic acid (3-chloro-phenyl)-amide in Example 88, 6-Benzyloxy-N-(3-chloro-phenyl)-N'-hydroxy-benzofuran-2-carboxamidine was obtained (51 mg, 43% yield).

$^1$H NMR (CDCl$_3$) δ 7.43 (m, 4H), 7.36 (d, J=8.4 Hz, 1H), 7.33 (tt, J1=6.8 Hz, J=1.2 Hz, 1H), 7.10 (m, 1H), 7.08 (t, J=8.0 Hz, 1H), 7.01 (m, 1H), 6.98 (d, J=2.0 Hz, 1H), 6.95 (t, J=2.0 Hz, 1H), 6.92 (d, J=2.2 Hz, 1H), 6.82 (s, 1H), 6.68 (dm, J=6.8 Hz, 1H), 5.07 (s, 2H). MS (ES+): 393 (M+H, 100).

Example 108

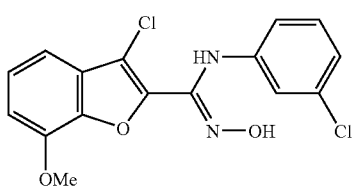

Following the procedures described for Example 88, substituting 7-methoxy-benzofuran-2-carboxylic acid (3-chloro-phenyl)-amide for 7-pyrrolidin-1-yl-benzofuran-2-carboxylic acid (3-chloro-phenyl)-amide in Example 88, 3-chloro-N-(3-chloro-phenyl)-N'-hydroxy-7-methoxy-benzofuran-2-carboxamidine was obtained 1(6 mg, 15% yield).

$^1$H NMR (CDCl$_3$) δ 7.16 (m, 2H), 7.23 (m, 1H), 7.13 (d, J=8.4 Hz, 1H), 7.09 (m, 1H), 7.06 (dt, J1=1.5 Hz, J2=8.0 Hz, 1H), 6.99 (d, J=5.6 Hz, 1H), 6.98 (s, 1H), 6.91 (t, J=1.5 Hz, 1H), 6.74 (t, J=8.4 Hz, 1H), 6.67 (dm, J=8.0 Hz, 1H), 3.86 (s, 3H). MS (ES+): 351 (M+H, 100).

Example 109

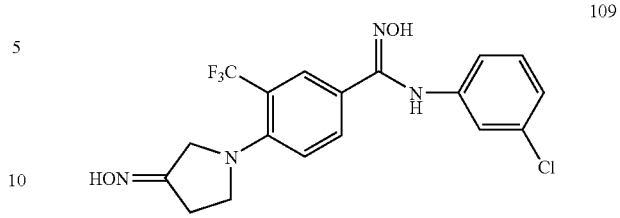

109

Compound of Formula (Z): R'=3-CF$_3$, R"=4-(3-hydroxy-imino-pyrolidin-1-yl, and R'''=Cl. Step a. A sample of the compound from Example 52 (0.524 g, 1.31 mmol) was treated with (iPr)$_3$SiCl (0.364 ml, 1.7 rnmol), NEt$_3$ (0.293 ml, 2.1 mmol) and DMAP (0.020 g, 0.16 mmol) in DCM (6 mL) overnight at rt. The reaction mixture was then poured into water and extracted with EtOAc. The organic layer was separated, washed with brine, dried with anhydrous Na$_2$SO$_4$, concentrated by rotary evaporation and purified by flash chromatography on silica gel with a gradient elution of 35–45% EtOAc/hexanes to afford the TIPS compound as a white solid (0.34 g, 47%).

To a mixture of DMSO (0.131 mL, 1.84 mmol) and DCM (5 mL) at −78° C. under a nitrogen atmosphere was added (COCl)$_2$ (0.46 mL, 2.0 M in DCM) via syringe. The solution was stirred for 15 min at the low temperature. The TIPS protected compound from Step a above (0.34 g, 0.613 mmol) was added to the above solution. Stir continued at the low temperature for an additional hour, at which time, NEt$_3$ (0.388 mL, 2.79 mmol) was added and the solution was allowed to warm to rt. It was then poured into water and extracted with EtOAc. The organic layer was separated, washed with brine, dried with anhydrous Na$_2$SO$_4$, concentrated by rotary evaporation and purified by flash chromatography on silica gel with 20% EtOAc/hexanes as the eluent to yield the corresponding ketone as a white solid (0.240 g, 71%).

The above ketone (0.066 g, 0.12 mmol) was stirred with hydroxyamine hydrochloride (0.033 g, 0.47 mmol) in MeOH (1 mL) at rt. After 1 hr, the reaction was complete. It was then poured into sat. NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 70–90% EtOAc/hexanes to yield the title compound as a white solid (0.045 g, 91%). $^1$H NMR (DMSO-d$_6$): δ 10.77 (s, 1H), 10.70 (s, 1H), 8.58 (s, 1H), 7.65 (d, J=2.2 Hz, 1H), 7.52 (d, J=7.8 Hz, 1H), 7.28 (d, J=8.9 Hz, 1H), 7.08 (dd, J=8.1, 8.1 Hz, 1H), 6.79 (m, 2 H), 6.50 (d, J=8.9 Hz, 1H), 3.92 (m, 2H), 3.37 (m, 2H), 2.64 (m, 2H). MS (ES): 413 [M+H]$^+$.

Example 110

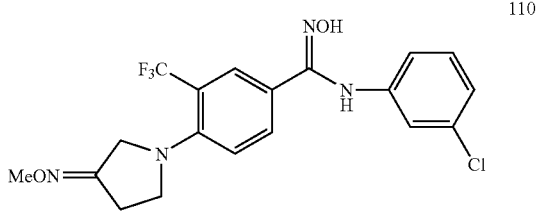

110

Compound of Formula (Z): R'=3-CF$_3$, R"=4-(3-methoxy-imino-pyrolidin-1-yl, and R'''=Cl. The title compound was prepared by treating a sample of the ketone intermediate obtained in Step a of Example 200 (0.066 g, 0.12 mmol) and substituting methoxyamine hydrochloride (0.030 g, 0.36 mmol) for hydroxyamine hydrochloride in Step b. $^1$H NMR (DMSO-d$_6$): δ 10.78 (s, 1H), 8.59 (s, 1H), 7.65 (d, J=2.1 Hz, 1H), 7.53 (d, J=8.9 Hz, 1H), 7.28 (d, J=8.8 Hz, 1H), 7.08 (dd, J=8.0, 8.0 Hz, 1H), 6.80 (m, 2 H), 6.50 (d, J=8.9 Hz, 1H), 3.92 (m, 2H), 3.78 (s, 3H), 3.37 (m, 2H), 2.68 (m, 2H). MS (ES): 427 [M+H]$^+$.

Example 111

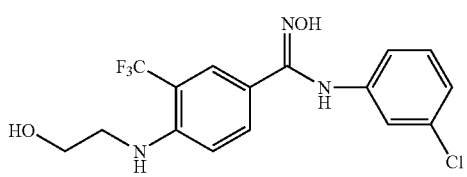

Compound of Formula (Z): R'=3-CF$_3$, R"=4-(2-hydroxyethylamino)-, and R'''=Cl. A mixture of the compound from Example 17 (0.080 g, 0.24 mmol) and 2-aminoethanol (0.101 ml, 1.68 mmol) in DMSO (1 mL) was heated to 125° C. for 24 hrs. The mixture was then cooled to rt, poured into water and extracted with EtOAc. The organic layer was separated, washed with brine, dried with anhydrous Na$_2$SO$_4$, concentrated by rotary evaporation and purified by flash chromatography on silica gel with a gradient elution of 70–90% EtOAc/hexanes to yield the title compound as a yellowish solid (0.036 g, 40%). 1H NMR (DMSO-d$_6$): δ 10.54 (s, 1H), 8.45 (s, 1H), 7.45 (d, J=2.1, 1H), 7.38 (d, J=8.8 Hz, 1H), 7.08 (dd, J=7.7, 7.7 Hz, 1H), 6.80 (m, 3H), 6.52 (d, J=7.4 Hz, 1H), 5.48 (s, 1H), 4.86 (t, J=6.6 Hz, 1H), 3.57 (m, 2H), 3.22 (m, 2H). MS (ES): 374 [M+H]$^+$.

Example 112

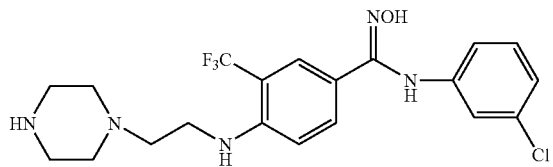

Compound of Formula (Z): R'=3-CF$_3$, R"=4-[2-(1-piperazino)ethylamino]-, and R'''=Cl. Following the same procedure as was used in Example 202 except substituting 1-(2-aminoethyl)piperazine for 2-aminoethanol, the title compound was obtained $^1$H NMR (DMSO-d$_6$): δ 10.55 (s, 1H), 8.45 (s, 1H), 7.45 (d, J=1.9 Hz, 1H), 7.39 (d, J=10.5 Hz, 1H), 7.07 (dd, J=7.2, 7.2 Hz, 1H), 6.79 (m, 3H), 6.52 (d, J=8.9 Hz, 1 H), 5.70 (m, 1H), 5.20 (m, 2H), 2.70 (m, 4H), 2.54 (m, 2H), 2.35 (m, 4H). MS (ES): 442 [M+H]$^+$.

Example 113

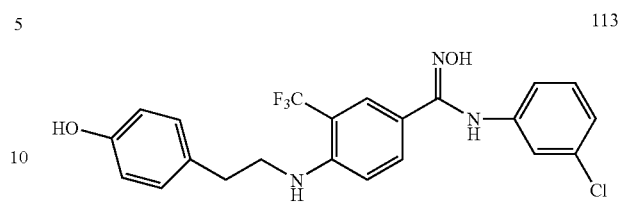

Compound of Formula (Z): R'=3-CF$_3$, R"=4-[2-(4-hydroxyphenyl)ethylamino]-, and R'''=Cl. Following the same procedure as was used in Example 202 except substituting tyromine for 2-aminoethanol, the title compound was obtained $^1$H NMR (DMSO-d$_6$): δ 10.53 (s, 1H), 9.16 (s, 1H), 8.46 (s, 1H), 7.45 (s, 1H), 7.39 (d, J=7.8 Hz, 1H), 7.05 (m, 3H), 6.82 (m, 3H), 6.69 (m, 2H), 6.5 (d, J=7.2 Hz, 1H), 5.50 (m, 1H), 3.38 (m, 2H), 2.73 (t, J=5.5 Hz, 2H). MS (ES): 450 [M+H]$^+$.

Example 114

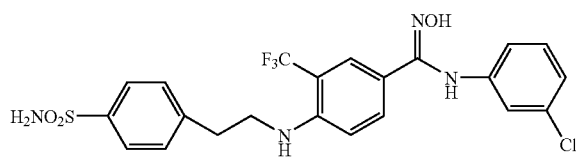

Compound of Formula (Z): R'=3-CF$_3$, R"=4-[2-(4-sulfomoylphenyl)ethylamino]-, and R'''=Cl. Following the same procedure as was used in Example 202 except substituting 4-(2-aminoethyl)benzenesulfonamide for 2-aminoethanol, the title compound was obtained $^1$H NMR (DMSO-d$_6$): δ 10.56 (s, 1H), 8.48 (s, 1H), 7.45 (m, 2H), 7.46 (m, 3H), 7.43 (d, J=9.4 Hz, 1H), 7.30 (m, 2H), 7.10 (dd, J=6.7, 6.7 Hz, 1H), 6.94 (d, J=10.0 Hz, 1H), 6.82 (m, 2H), 6.56 (d, J=8.9 Hz, 1H), 5.73 (m, 1H), 3.47 (m, 2H), 2.95 (t, J=8.3 Hz, 2H). MS (ES): 513 [M+H]$^+$.

Example 115

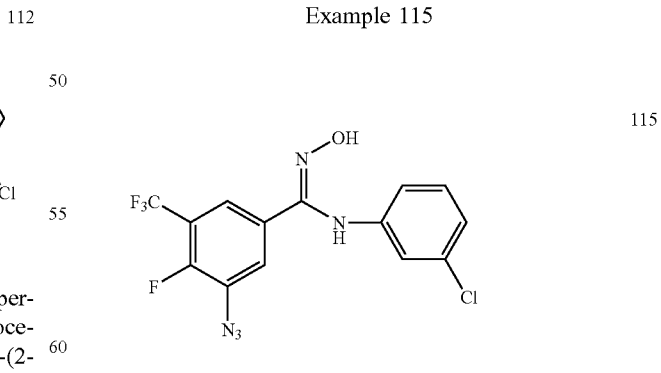

Step a. Methyl 4-fluro-3-trifluoromethylbenzoate (8.80 g, 39.6 mmol, from Oakwood Products, Inc. West Cloumbia, S.C.) was stirred with conc. H$_2$SO$_4$ (60 mL) and fumaric HNO$_3$ (60 mL) overnight at rt. The mixture was then cooled with ice, poured onto ice-water and extracted with EtOAc. The organic layer was separated, washed with brine, dried with anhydrous Na$_2$SO$_4$, concentrated by rotary evaporation and purified by flash chromatography on silica gel with a gradient elution of 10–20% EtOAc/hexanes to afford a greenish oil (8.50 g, 80%).

Step b. The nitrobenzoate compound from above (8.40 g, 31.46 mmol) was reduced by heating with SnCl$_2$.2H$_2$O (28.40 g, 126 mmol) in EtOAc (220 mL) at 85° C. for two hrs. After cooled to rt, it was basicified with sat. NaHCO$_3$ and extracted with EtOAc. The whole was filtered. The organic layer was separated, washed with brine, dried with anhydrous Na$_2$SO$_4$, concentrated by rotary evaporation and purified by flash chromatography on silica gel with a gradient elution of 30–50% EtOAc/hexanes to afford aniline as a white solid (6.58 g, 88%).

Step c. The aniline compound from Step b above (6.11 g, 25.78 mmol) was added to 6N HCl (400 mL) to obtain a suspension. After cooled to −5∼−10° C., NaNO$_2$ (2.135 g, 30.94 mmol, dissolved in water) was added. After the mixture was maintained at the same temperature for 30 min, NaN$_3$ (3.35 g, 51.56 mmol, suspended in water) was added in portions. Upon finishing addition, the mixture was warmed to rt and stayed for 1 hr at rt. It was then extracted with EtOAc. The organic layer was separated, washed with brine, dried with anhydrous Na$_2$SO$_4$, concentrated by rotary evaporation and purified by flash chromatography on silica gel eluting with 20% EtOAc/hexanes to afford azide as a yellowish solid (3.08 g, 45%).

Step d. The azido substituted benzoate from above (3.08 g, 11.70 mmol) was hydrolyzed by treatment with LiOH.H$_2$O (0.983 g, 23.42 mmol) at rt for 40 min in a mixed solvent of THF (70 mL), MeOH (70 mL) and water (35 mL). It was then poured into 5% HCl and extracted with EtOAc. The organic layer was separated, washed with brine, dried with anhydrous Na$_2$SO$_4$, concentrated by rotary evaporation and purified by flash chromatography on silica gel eluting with a gradient elution of 0–10% MeOH/EtOAc to afford acid as a greenish solid (2.90 g, 99%). The material contained a 12% minor product arising from the methoxy substitution of the fluorine atom. The latter was readily separated in the following steps.

Step e. The acid from above (1.150 g, 5 mmol) was then treated with (COCl)$_2$ (5.0 mL, 2.0 M/DCM) in DCM (30 mL) in the presence of 3 drops of DMF as catalyst for 2 hrs or until bubbles ceased. The solvent was then removed. The acyl chloride thus obtained (in DCM) was added to another flask at 0° C. containing 3-chloroaniline (0.582 mL, 5.5 mmol), TEA (2.10 mL, 15 mmol) in DCM (50 mL). The mixture was warmed to rt and stirred for 1 hr at rt. It was then poured into water and extracted with EtOAc. The organic layer was separated, washed with brine, dried with anhydrous Na$_2$SO$_4$, concentrated by rotary evaporation and purified by flash chromatography on silica gel with a gradient elution of 10–30% EtOAc/hexanes to afford amide as a white solid (0.220 g, 13%, not optimized).

Step f. Amide from above (0.220 g, 0.61 mmol) was then heated with PCl$_5$ (0.192 g, 0.92 mmol) in 6 ml of 1,2-dichloroethane to 70° C. in a sealed flask for 5 hrs. It was then cooled to rt and the solvent removed. The residue was stirred with NH$_2$OH.HCl (0.127 g, 1.83 mmol) and TEA (0.51 mL, 3.66 mmol) in acetonitrile (4 mL) for 4 hrs at rt. It was then poured into 5% HCl and extracted with EtOAc. The organic layer was separated, washed with brine, dried with anhydrous Na$_2$SO$_4$, concentrated by rotary evaporation and purified by flash chromatography on silica gel with a gradient elution of 20–35% EtOAc/hexanes to afford the title compound as a yellowish solid (0.090 g, 39%). $^1$H NMR (DMSO-d$_6$): δ 11.08 (s, 1H), 8.76 (s, 1H), 7.58 (d, J=7.9 Hz, 1H), 7.42 (d, J=6.0 Hz, 1H), 7.10 (dd, J=8.0, 8.0 Hz, 1H), 6.85 (m, 2H), 6.51 (d, J=9.7 Hz, 1H). MS (ES): 372 [M−H]$^+$.

Example 116

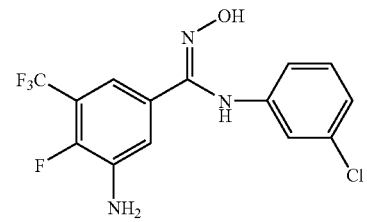

A sample of the compound from Example 115 (0.300 g, 0.8 mmol) in THF (1 mL) and EtOH (6 mL) at 0° C. was added a premixed solution of SnCl$_2$.2H$_2$O (0.271 g, 1.2 mmol) and 4.33 mL of 2M NaOH at 0° C. slowly. After 10 min, the mixture was filtered. The filtrate was collected, poured into water and extracted with EtOAc. The organic layer was separated, washed with brine, dried with anhydrous Na$_2$SO$_4$, concentrated by rotary evaporation and purified by flash chromatography on silica gel with a gradient elution of 50–80% EtOAc/hexanes to afford the title compound as an wax (0.208 g, 75%). $^1$H NMR (DMSO-d$_6$): δ 10.82 (s, 1H), 8.58 (s, 1H), 7.09 (m, 2H), 6.80 (m, 3H), 6.48 (d, J=7.8 Hz, 1H), 5.75 (s, 2H). MS (ES): 348 [M+H]$^+$.

Example 117

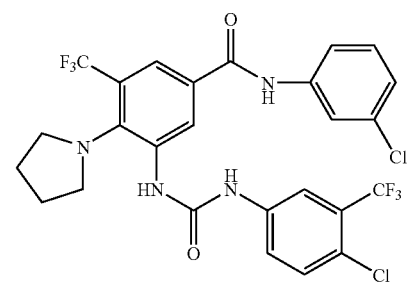

Step a. 4-Chloro-5-nitro-3-trifluoromethylbenzoic acid (5.03 g, 18.7 mmol, prepared from the nitration of 4-chloro-3-trifluoromethylbenzoic acid under the conditions described in Step a of Example 115) was treated with (COCl)$_2$ (18.7 mL, 2.0 M/DCM) in DCM (100 mL) in the presence of 2 drops of DMF as catalyst for 2.5 hrs. The solvent was then removed. The obtained acyl chloride (in DCM) was added to another flask at 0° C. containing 3-chloroaniline (1.95 ml, 18.7 mmol), TEA (7.82 mL, 56.1 mmol) in DCM (200 mL). The mixture was then warmed to rt and stayed for 1 hr at rt. It was then poured into water and extracted with EtOAc. The organic layer was separated, washed with brine, dried with anhydrous Na$_2$SO$_4$, concentrated by rotary evaporation and purified by flash chromatography on silica gel with a gradient elution of 20–30% EtOAc/hexanes to afford amide as a yellowish solid (6.80 g, 96%).

Step b. A sample of the amide from above (0.050 g, 0.132 mmol) was also heated with pyrrolidine (1.30 g, 3.43 mmol) in DMSO (15 mL) for 2 hrs at 50° C. It was then cooled to rt, poured into water and extracted with EtOAc. The organic layer was separated, washed with brine, dried with anhydrous Na$_2$SO$_4$, concentrated by rotary evaporation and purified by flash chromatography on silica gel eluting with 20% EtOAc/hexanes to afford the pyrrolino-substituted compound as a bright yellow solid (1.28 g, 90%).

Step c. A sample of this compound (1.28 g, 3.37 mmol), SnCl$_2$·2H$_2$O (3.04 g, 13.47 mmol) and EtOAc (80 mL) was heated to 80° C. in a sealed flask for 40 min. It was then cooled to rt, basified with sat. NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 30–50% EtOAc/hexanes to afford an aniline as a yellow solid (0.375 g, 29%).

Step d. A mixture of the aniline from above (0.030 g, 0.078 mmol), 3,4-dichlorophenylisocyanate (0.060 g, 0.32 mmol) in DCM (1.5 mL) was heated in a sealed vial to 70° C. for 1 hr. It was then cooled to rt, quenched with MeOH, poured into water and extracted with EtOAc. The organic layer was separated, washed with brine, dried with anhydrous Na$_2$SO$_4$, concentrated by rotary evaporation and purified by flash chromatography on silica gel with a gradient elution of 30–50% EtOAc/hexanes to afford the urea compound as a white solid (0.030 g, 67%). $^1$H NMR (DMSO-d$_6$): δ 10.53 (s, 1H), 9.83 (s, 1H), 8.76 (d, J=1.8 Hz, 1H), 8.15 (s, 1H), 7.94 (m, 3H), 7.70 (d, J=11.1 Hz, 1H), 7.55 (d, J=8.8 Hz, 1H), 7.38 (m, 2H), 7.18 (d, J=8.9 Hz, 1H), 3.15 (m, 4H), 2.03 (m, 4H). MS (ES): 571 [M+H]$^+$.

Example 118

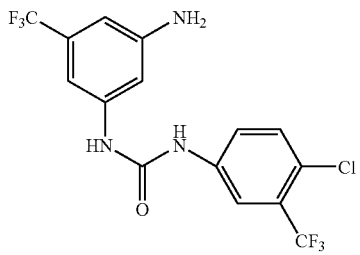

To a solution of 3,5-diaminobenzotrifluoride (2.114 g, 12 mmol) in DCM (30 mL) at 0° C. was added 4-chloro-3-(trifluoromethyl)phenyl isocyanate (2.659 g, 12 mmol in DCM) dropwise. The mixture was warmed to rt and stirred for 1 hr at rt. It was then quenched with MeOH, poured into water and extracted with EtOAc. The organic layer was separated, washed with brine, dried with anhydrous Na$_2$SO$_4$, concentrated by rotary evaporation and purified by flash chromatography on silica gel with a gradient elution of 10–30% CH$_3$CN/DCM to afford 118 as a white solid (4.10 g, 86%). $^1$H NMR (DMSO-d$_6$): δ 9.09 (s, 1H), 8.88 (s, 1H), 8.12 (s, 1H), 7.61 (m, 2H), 7.00 (s, 1H), 6.88 (s, 1H), 6.50 (s, 1H), 5.58 (s, 2H). MS (ES): 398 [M+H]$^+$.

Example 119

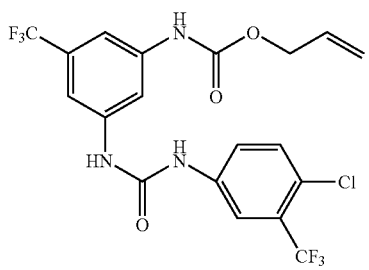

To a solution amino urea compound from Example 118 (0.100 g, 0.25 mmol), TEA (0.140 ml, 1 mmol) in DCM (1.5 ml) at 0° C. was added allyl chloroformate (0.120 ml, 1 mmol). The mixture was warmed to rt and stayed for 2 hr at rt. It was poured into water and extracted with EtOAc. The organic layer was separated, washed with brine, dried with anhydrous Na$_2$SO$_4$, concentrated by rotary evaporation and purified by flash chromatography on silica gel with a gradient elution of 30–60% EtOAc/hexanes to give the title compound as a white solid (0.015 g, 12%). $^1$H NMR (DMSO-d$_6$): δ 10.08 (s, 1H), 9.26 (s, 1H), 9.15 (s, 1H), 8.11 (d, J=2.1 Hz, 1H), 7.76 (s, 1H), 7.63 (m, 3H), 7.50 (s, 1H), 5.98 (m, 1H), 5.37 (d, J=17.8 Hz, 1H), 5.26 (d, J=11.1 Hz, 1H), 4.62 (m, 2H). MS (ES): 480 [M−H]$^+$.

Example 120

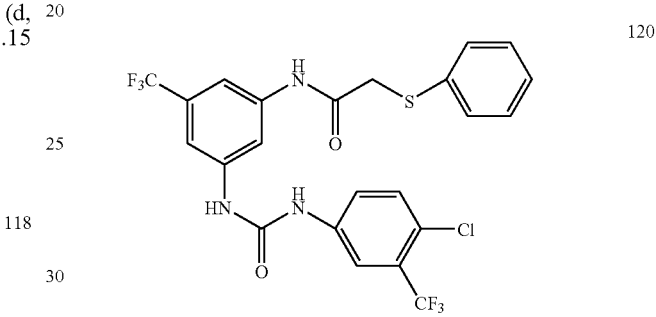

The title compound was synthesized by treating a sample of the compound from Example 118 with phenylthioacetyl chloride in the presence of triethylamine in DCM at 0° C. for 2 hr. $^1$H NMR (DMSO-d$_6$): δ 10.54 (s, 1H), 9.30 (s, 1H), 9.19 (s, 1H), 8.14 (d, J=1.8 Hz, 1H), 7.95 (s, 1H), 7.63 (m, 4H), 7.42 (m, 2H), 7.33 (m, 2H), 7.20 (dd, J=6.7, 6.7 Hz, 1H), 3.88 (s, 2H). MS (ES): 546 [M−H]$^+$.

Example 121

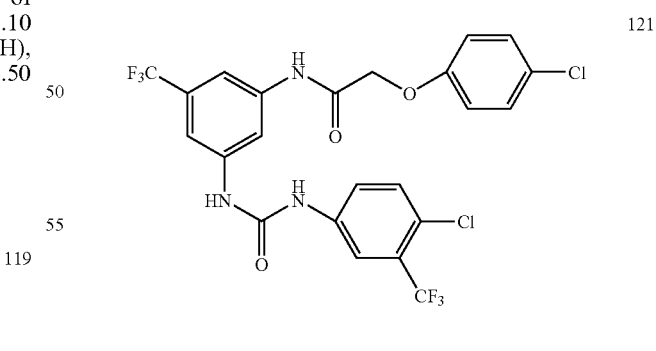

The title compound was synthesized following conditions for Example 120 except substituting 4-chlorophenoxyacetyl chloride for phenylthioacetyl chloride. $^1$H NMR (DMSO-d$_6$): δ 10.43 (s, 1H), 9.30 (s, 1H), 9.19 (s, 1H), 8.13 (d, J=2.2 Hz, 1H), 8.03 (s, 1H), 7.71 (s, 1H), 7.63 (m, 3H), 7.36 (m, 2H), 7.03 (m, 2H), 4.74 (s, 2H). MS (ES): 564 [M−H]$^+$.

Example 122

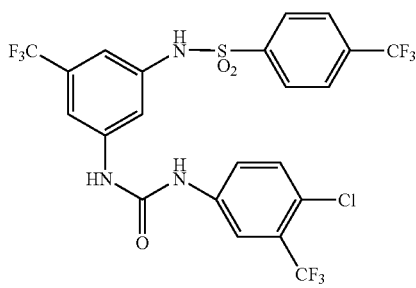

The title compound was synthesized from the treatment of a sample of compound from Example 118 with 4-trifluoromethylbenzenesulfonyl and triethylamine in DCM. $^1$H NMR (DMSO-d$_6$): δ 10.93 (s, 1H), 9.33 (s, 1H), 9.19 (s, 1H), 8.08 (s, 1H), 8.00 (m, 4H), 7.63 (m, 3H), 7.52 (s, 1H), 6.99 (s, 1H). MS (ES): 604 [M–H]$^−$.

Example 123

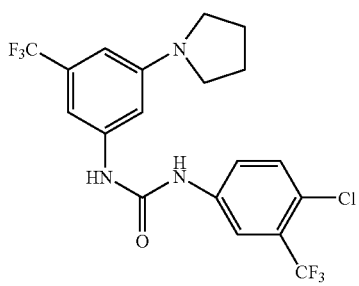

The title compound was synthesized in 4 steps according to the following sequence.

Step a. A mixture of 1-fluoro-3-iodo-5-nitrobenzene (2.733 g, 10.24 mmol), FSO$_2$CF$_2$CO$_2$Me (3.26 mL, 25.6 mmol), CuI (2.342 g, 12.3 mmol) in DMF (30 mL) was heated to 90° C. for 2 days under an nitrogen atmosphere. It was then poured into water and extracted with EtOAc. The organic layer was separated, washed with brine, dried with anhydrous Na$_2$SO$_4$, concentrated by rotary evaporation and purified by flash chromatography on silica gel with a gradient elution of 10–30% EtOAc/hexanes to yield 3-fluoro-5-nitrobenzotrifluoride as an oil (1.76 g, 82%).

Step b. A mixture of 3-fluoro-5-nitrobenzotrifluoride (0.120 g, 0.57 mmol), pyrrolidine (0.200 mL, 2.4 mmol) and DMSO (1.2 mL) was stirred for 1 hr. It was then poured into water and extracted with EtOAc. The organic layer was separated, washed with brine, dried with anhydrous Na$_2$SO$_4$, concentrated by rotary evaporation and purified by flash chromatography on silica gel with a gradient elution of 20–30% EtOAc/hexanes to yield the pyrrolino substituted product as a bright yellow solid (0.085 g, 57%).

Step c. The above intermediate (0.083 g, 0.32 mmol) was heated with SnCl$_2$.2H$_2$O (0.287 g, 1.27 mmol) in EtOAc (3 mL) to 80° C. in a sealed vial for 1 hr. It was then cooled to rt, basified with sat. NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 30–60% EtOAc/hexanes to afford the corresponding amine as an oil (0.055 g, 72%).

Step d. The obtained aniline above (0.055 g, 0.23 mmol) was stirred with 4-chloro-3-(trifluoromethyl)phenyl isocyanate (0.111 g, 0.5 mmol) in DCM (1.5 mL) at rt for 10 min. It was then poured into water and extracted with EtOAc. The organic layer was separated, washed with brine, dried with anhydrous Na$_2$SO$_4$, concentrated by rotary evaporation and purified by flash chromatography on silica gel with a gradient elution of 0–40% EtOAc/DCM to yield the title compound as a white solid (0.090 g, 87%). $^1$H NMR (DMSO-d$_6$): δ 9.15 (s, 1H), 9.00 (s, 1H), 8.09 (s, 1H), 7.62 (m, 2H), 7.10 (s, 1H), 6.80 (s, 1H), 6.40 (s, 1H), 3.24 (m, 4H), 1.96 (m, 4H). MS (ES): 452 [M+H]$^+$.

Example 124

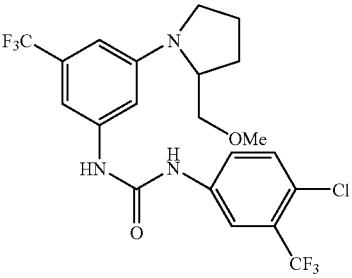

The title compound was synthesized according to the same sequence as was used for Example 123 except replacing pyrrolidine with 2-methoxymethylpyrrolidine in Step b. $^1$H NMR (DMSO-d$_6$): δ 9.15 (s, 1H), 9.02 (s, 1H), 8.08 (d, J=2.5 Hz, 1H), 7.63 (m, 2H), 7.20 (s, 1H), 6.86 (s, 1H), 6.48 (s, 1H), 3.86 (m, 1H), 3.20 ~3.40 (m, 3H), 3.29 (s, 3H), 3.09 (m, 1H), 1.94 (m, 4H). MS (ES): 496 [M+H]$^+$.

Example 125

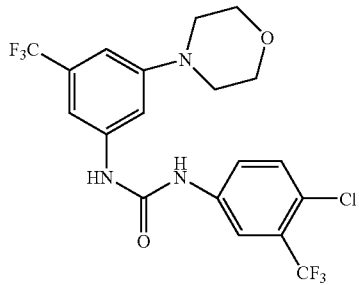

The title compound was synthesized according to the same sequence as was used for Example 123 with slightly modified conditions starting with 3-fluoro-5-nitrobenzotrifluoride and morpholine in Step b. $^1$H NMR (DMSO-d$_6$): δ 9.24 (s, 1H), 9.05 (s, 1H), 8.09 (d, J=2.5 Hz, 1H), 7.62 (m, 2H), 7.31 (s, 1H), 7.23 (s, 1H), 6.86 (s, 1H), 3.74 (m, 4H), 3.16 (m, 4H). MS (ES): 468 [M+H]$^+$.

Example 126

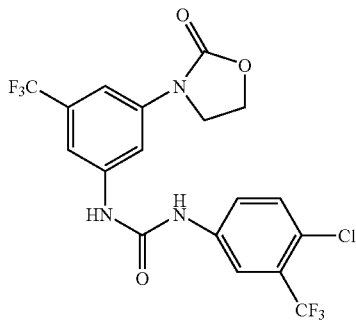

The title compound was synthesized following a similar sequence of reactions as described in Example 123.

Step a. A sample of 3-fluoro-5-nitrobenzotrifluoride (0.209 g, 1 mmol), 2-aminoethanol (0.244 g, 4 mmol) and DMSO (3.5 mL) was stirred for 20 hrs at 70° C. It was then cooled to rt, poured into brine and extracted with EtOAc. The organic layer was separated, washed with brine, dried with anhydrous $Na_2SO_4$, concentrated by rotary evaporation and purified by flash chromatography on silica gel eluting with 80% EtOAc/hexanes to yield the 2-hydroxyethylamino substituted product as a bright yellow solid (0.222 g, 89%).

Step b. This intermediate (0.075 g, 0.3 mmol) was heated with triphosgene (0.300 g, 1 mmol) in DCM (2 mL) to 80° C. in a sealed vial for 2 hrs. It was then cooled to rt, poured into water and extracted with EtOAc. The organic layer was separated, washed with brine, dried with anhydrous $Na_2SO_4$, concentrated by rotary evaporation and purified by flash chromatography on silica gel with a gradient elution of 30–70% EtOAc/hexanes to afford the corresponding oxolidinone as a white solid (0.036 g, 43%).

Step c. The above intermediate (0.031 g, 0.112 mmol) was heated with $SnCl_2 \cdot 2H_2O$ (0.101 g, 0.45 mmol) in EtOAc (3 ml) to 80° C. in a sealed vial for 1 hr. It was then cooled to rt, basified with sat. $NaHCO_3$ and extracted with EtOAc. The organic layer was separated, washed with brine, dried with anhydrous $Na_2SO_4$, concentrated by rotary evaporation and purified by flash chromatography on silica gel with a gradient elution of 60–90% EtOAc/hexanes to afford the corresponding aniline.

Step d. The aniline obtained above (0.011 g, 0.04 mmol) was stirred with 4-chloro-3-(trifluoromethyl)phenyl isocyanate (0.040 g, 0.18 mmol) in DCM (2 ml) and DMF (0.5 ml) at rt for 30 min. It was poured into water and extracted with EtOAc. The organic layer was separated, washed with brine, dried with anhydrous $Na_2SO_4$, concentrated by rotary evaporation and purified by flash chromatography on silica gel with a gradient elution of 70–100% EtOAc/hexanes to afford the title compound as white solid (0.011 g, 59%). $^1$H NMR (DMSO-$d_6$): δ 9.39 (s, 1H), 9.24 (s, 1H), 8.10 (s, 1H), 7.86 (s, 1H), 7.74 (s, 1H), 7.63 (m, 2H), 7.53 (s, 1H), 4.46 (t, J8.3 Hz, 2H), 4.10 (t, J=8.3 Hz, 2H). MS (ES): 466 [M–H]$^+$.

Example 127

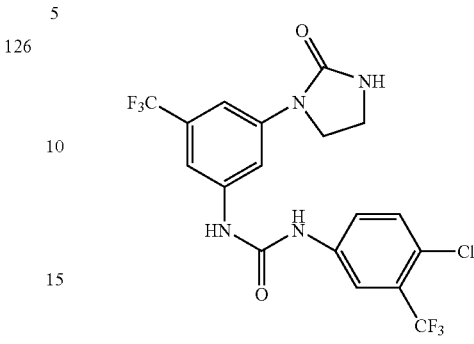

The title compound was synthesized according to the same sequence as was used in Example 126 with slightly modified conditions substituting ethylenediamine for 2-aminoethanol in Step a in an overall yield of 37%. $^1$H NMR (DMSO-$d_6$): δ 9.25 (s, 1H), 9.15 (s, 1H), 8.09 (d, J=2.3 Hz, 1H), 7.78 (s, 1H), 7.60 (s, 4H), 7.19 (s, 1H), 3.88 (t, J=8.3 Hz, 2H), 3.42 (t, J=8.3 Hz, 2H). MS (ES): 465 [M–H]$^+$.

Example 128

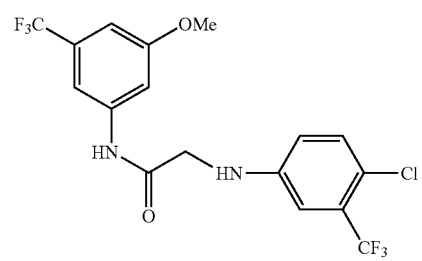

A mixture of 3-methoxy-5-trifluoromethylaniline (0.077 g, 0.4 mmol, available from Oakwood), N-(4-chloro-3-trifluoromethylphenyl)glycine (0.051 g, 0.2 mmol), EDC (0.153 g, 0.8 mmol), HOBt (0.109 g, 0.8 mmol) in DMF (2.5 mL) was stirred at rt overnight. It was then poured into sat. $NaHCO_3$ and extracted with EtOAc. The organic layer was separated, washed with brine, dried with anhydrous $Na_2SO_4$, concentrated by rotary evaporation and purified by flash chromatography on silica gel with a gradient elution of 30–60% EtOAc/hexanes to afford the title compound as a white solid (0.035 g, 41%). $^1$H NMR (DMSO-$d_6$): δ 10.36 (s, 1H), 7.61 (s, 1H), 7.47 (s, 1H), 7.37 (d, J=8.8 Hz, 1H), 7.05 (d, J=2.6 Hz, 1H), 6.94 (s, 1H), 6.81 (d, J=8.8 Hz, 1H), 6.70 (s, 1H), 3.98 (s, 2H), 3.80 (s, 3H). MS (ES): 425 [M–H]$^+$.

The required N-(4-chloro-3-trifluoromethylphenyl)glycine was prepared as follows. A mixture of 4-chloro-3-trifluoromethylaniline (1.369 g, 7 mmol), ethyl bromoacetate (1.55 mL, 14 mmol), $K_2CO_3$ (2.764 g, 20 mmol) in DMF (40 mL) was heated at 70° C. overnight. It was then poured into water and extracted with EtOAc. The organic layer was separated, washed with brine, dried with anhydrous $Na_2SO_4$, concentrated by rotary evaporation and purified by flash chromatography on silica gel with a gradient elution of 20–40% EtOAc/hexanes to afford ethyl N-(4-chloro-3-trifluoromethylphenyl)glycine as a white solid (0.180 g, 9%).

The glycine ester (0.180 g, 0.64 mmol) was stirred with LiOH.H₂O (0.054 g, 1.28 mmol) in a mixed solvent of THF (2 mL), MeOH (2 mL) and water (1 ml) for 30 min. The mixture was then adjusted to pH=6 with HOAc. It was then poured into water and extracted with EtOAc. The organic layer was separated, washed with brine, dried with anhydrous Na₂SO₄, concentrated by rotary evaporation and purified by flash chromatography on silica gel with a gradient elution of 0–100% MeOH/EtOAc to afford N-(4-chloro-3-trifluoromethylphenyl)glycine as a foam solid (0.160 g, 98%).

Example 129

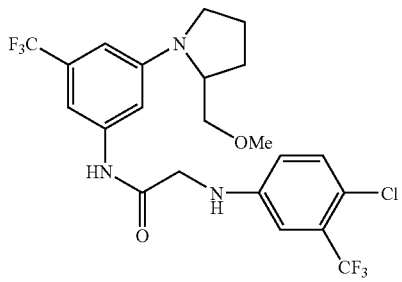

129

A mixture of 3-(2-methoxymethylpyrrolidino)-5-trifluoromethylaniline (0.083 g, 0.3 mmol, obtained as an intermediate for the preparation of the compound in Example 124, N-(4-chloro-3-trifluoromethylphenyl)glycine (0.051 g, 0.2 mmol), EDC (0.115 g, 0.6 mmol), HOBt (0.082 g, 0.6 mmol) in DMF (2 ml) was stirred at rt overnight. It was then poured into sat. NaHCO₃ and extracted with EtOAc. The organic layer was separated, washed with brine, dried with anhydrous Na₂SO₄, concentrated by rotary evaporation and purified by flash chromatography on silica gel with a gradient elution of 30–60% EtOAc/hexanes to give the title compound as a white solid (0.055 g, 55%). ¹H NMR (DMSO-d₆): δ 10.18 (s, 1H), 7.37 (d, J=7.8 Hz, 1H), 7.29 (s, 1H), 7.10 (s, 1H), 7.03 (s, 1H), 6.80 (m, 1H), 6.68 (m, 1H), 6.52 (s, 1H), 3.95 (s, 2H), 3.83 (m, 1H), 3.30 (m, 1H), 3.27 (s, 3H), 3.07 (m, 1H), 1.93 (m, 4H). MS (ES): 510 [M+H]⁺.

Example 130

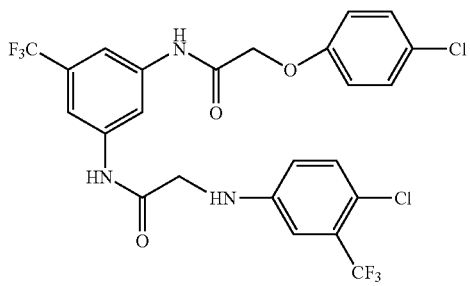

130

This compound was prepared in two steps. To a solution of 3,5-diaminobenzotrifluoride (0.705 g, 4 mmol) in DCM (20 ml) at 0° C. was added 4-chlorophenoxy acetyl chloride (0.624 ml, 4 mmol). The mixture was warmed to rt and stirred for 1 hr at rt. It was then poured into water and extracted with EtOAc. The organic layer was separated, washed with brine, dried with anhydrous Na₂SO₄, concentrated by rotary evaporation and purified by flash chromatography on silica gel with a gradient elution of 30–70% EtOAc/hexanes to mono acylated compound as an off-white solid (0.420 g, 30%).

The mono aniline from above (0.138 g, 0.4 mmol), N-(4-chloro-3-trifluoromethylphenyl)glycine (0.051 g, 0.2 mmol), EDC (0.153 g, 0.8 mmol), HOBt (0.109 g, 0.8 mmol) in DMF (2.5 ml) was stirred at rt overnight. It was then poured into sat. NaHCO₃ and extracted with EtOAc. The organic layer was separated, washed with brine, dried with anhydrous Na₂SO₄, concentrated by rotary evaporation and purified by flash chromatography on silica gel with a gradient elution of 40–70% EtOAc/hexanes to give the title compound as an off-white solid (0.046 g, 39%). ¹H NMR (DMSO-d₆): δ 10.44 (m, 2H), 8.19 (s, 1H), 7.76 (m, 2H), 7.36 (m, 3H), 7.02 (m, 3H), 6.82 (d, J=10.0 Hz, 1H), 6.70 (m, 1H), 4.73 (s, 2H), 3.98 (d, J=5.9 Hz, 2H). MS (ES): 580 [M+H]⁺.

Example 131

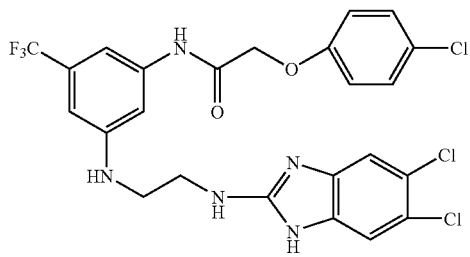

131

The title compound was prepared according the reaction sequence described below.

Step a. A mixture of 3-fluoro-5-nitrobenzotrifluoride (0.125 g, 0.6 mmol), ethylenediamine (0.180 ml, 2.4 mmol) was heated to 70° C. overnight. The mixture was then cooled to rt, poured into water and extracted with EtOAc. The organic layer was separated, washed with brine, dried with anhydrous Na₂SO₄, concentrated by rotary evaporation and purified by flash chromatography on silica gel with a gradient elution of 0–15% NH₄OH in 30 MeOH/DCM to the N-(2-aminoethyl)aniline as a white solid (0.103 g, 41%).

Step b. A mixture of the aniline from above (0.050 g, 0.2 mmol), 2,5,6-trichlorobenzimidazole (0.050 g, 0.226 mmol), diisopropylethylamine (0.1 mL, 0.57 mmol) in DMSO (1 mL) was heated to 150° C. for 1.5 hrs. The mixture was then cooled to rt, poured into water and extracted with EtOAc. The organic layer was separated, washed with brine, dried with anhydrous Na₂SO₄, concentrated by rotary evaporation and purified by flash chromatography on silica gel with a gradient elution of 0–20% MeOH/EtOAc to yield the coupled compound as a yellow oil (0.028 g, 32%).

Step c. The product from above (0.027 mg, 0.062 mmol) was then heated with SnCl₂.2H₂O (0.070 g, 0.3 mmol) in EtOAc (1 ml) to 80° C. in a sealed vial for 30 min. It was then cooled to rt, basified with sat. NaHCO₃ and extracted with EtOAc. The organic layer was separated, washed with brine, dried with anhydrous Na$_2$SO$_4$, concentrated by rotary evaporation and purified by flash chromatography on silica gel with a gradient elution of 0–30% MeOH/EtOAc to give the aniline as a brownish solid (0.020 g, 80%).

Step d. To a solution of the aniline form above (0.020 g, 0.05 mmol), TEA (0.030 ml, 0.21 mmol) in DCM (1 mL) at rt was added 4-chlorophenoxyacetyl chloride (0.015 mL, 0.1 mmol). After stirred for 10 min, it was poured into water and extracted with EtOAc. The organic layer was separated, washed with brine, dried with anhydrous Na$_2$SO$_4$, concentrated by rotary evaporation and purified preparative TLC using 5% MeOH/DCM as the developing solvent to yield the desired product as a solid (2 mg, 6.8%). $^1$H NMR (DMSO-d$_6$): δ 11.06 (s, 1H), 10.11 (s, 1H), 7.33 (m, 4H), 7.18 (m 2H), 7.01 (m, 3H), 6.70 (s, 1H), 6.38 (m, 1H), 4.70 (s, 2H), 3.46 (m, 2H), 3.28 (m, 2H). MS (ES): 572 [M+H]$^+$.

Example 132

1-(4-Chloro-3-trifluoromethyl-phenyl)-3-(3-methoxymethoxy-5-trifluoromethyl-phenyl)-urea (132)

Step a. Methoxymethyl chloride (1.6 mL, 20.9 mmol) was added to a dichloromethane (50 mL) solution containing 3-nitro-5-trifluoraomethylphenol (2.89 g, 13.9 mmol) and diisopropylethylamine (4.8 mL, 27.8 mmol). After 3 hours of stirring at room temperature, the solution was washed with water (100 mL), brine (50 mL), dried over Na$_2$SO$_4$, and concentrated. The resulting oil was then hydrogenated over 10% Pd/C (300 mg) in ethanol (70 mL) at atmospheric pressure for 3 h. The suspension was filtered though a cake of celite and concentrated to give 3-Methoxymethoxy-5-trifluoromethyl-phenylamine as a light yellow oil.

Step b. 3-Methoxymethoxy-5-trifluoromethyl-phenylamine (237 mg, 1.07 mmol) and 4-choloro-3-trifluoromethylphenyl isocyanate (238 mg, 1.07 mmol) were dissolved in acetonitrile (20 mL) and heated at reflux for 6 hours. The solvent was then removed using reduced pressure and the resulting solid was purified using silica gel flash chromatography eluting with a solution of 20% EtOAc/hexanes. Similar fractions were pooled and concentrated to give the urea product (0.421 g, 89%) as an off-white solid. $^1$H NMR (CD$_3$OD) δ 7.80 (d, J=2 Hz, 1 H), 7.65 (d, J=8 Hz, 1 H), 7.50 (d, J=8 Hz, 1 H), 7.45 (s, 1 H), 7.43 (s, 1 H), 6.96 (s, 1 H), 5.31 (s, 2 H), 3.50 (s, 3 H); Electrospray MS (MH$^+$) m/z 443.

Example 133

1-(4-Chloro-3-trifluoromethyl-phenyl)-3-(3-hydroxy-5-trifluoromethyl-phenyl)-urea (133)

1-(4-Chloro-3-trifluoromethyl-phenyl)-3-(3-methoxymethoxy-5-trifluoromethyl-phenyl)-urea (100 mg, 0.25 mmol) from above was dissolved in a 1:1 solution of 3N HCl/ethyl acetate (20 mL) and stirred vigorously at room temperature for 16 h. Additional ethyl acetate was then added (50 mL) and the mixture was washed with water (2×50 mL), brine (50 mL), dried over Na$_2$SO$_4$, and concentrated. The resulting residue was purified using silica gel flash chromatography eluting with a 3:1 hexane/ethyl acetate solution. Similar fractions were pooled and concentrated to the title compound (72 mg, 72%) as an off-white solid. $^1$H NMR (CD$_3$OD) δ 7.97 (d, J=2 Hz, 1 H), 7.64 (dd, J=2 Hz, J=8 Hz, 1 H), 7.50 (d, J=8 Hz, 1 H), 7.22(s, 1 H), 7.21 (s, 1 H), 6.75 (s, 1 H); Electrospray MS (MH$^+$) m/z 399.

Example 134

1-(4-chloro-3-trifluoromethyl-phenyl)-3-(3-allyl-5-trifluoromethyl-phenyl)-urea (134)

The phenol compound obtained from Example 133 was treated with allyl bromide (1 eq.), and K$_2$CO$_3$ (2 eq.) in DMF at 60° C. for 24 h. After the reaction was finished, the resulting solution was directly injected on a preparative reverse phase HPLC column and fractions, which contained the desired product mass, were collected and concentrated using the Genevac system. $^1$H NMR (CD$_3$OD) δ 7.98 (d, J=2 Hz, 1 H), 7.65 (dd, J=2 Hz, J=8 Hz, 1 H) 7.50 (d, J=8 Hz, 1 H), 7.38 (s, 1 H), 7.34 (s, 1 H), 6.86 (s, 1 H), 6.07 (m, 1 H), 5.42 (dq, J=2 Hz, J=17 Hz, 1 H), 5.29 (dq, J=2 Hz, J=12 Hz, 1 H), 4.61 (dt, J=2 Hz, J=5 Hz, 2 H).

Example 135

1-(4-chloro-3-trifluoromethyl-phenyl)-3-(3-(3-chlorobenzyl)-5-trifluoromethyl-phenyl)-urea (135)

The title compound was synthesized following the same procedure described in Example 134. $^1$H NMR (CD$_3$OD) δ 7.99 (d, J=2 Hz, 1 H), 7.65 (dd, J=2 Hz, J=8 Hz, 1 H), 7.51 (d, J=8 Hz, 1 H), 7.46 (m, 2 H), 7.40 (m, 2 H), 7.32 (s, 1 H), 6.93 (s, 1 H), 5.14 (s, 2 H).

Example 136

N-[3-(3-Chloro-phenoxymethyl)-5-trifluoromethyl-phenyl]-2-(4-piperidin-1-yl-3-trifluoromethyl-phenylamino)-acetamide (136)

Step a. Preparation of 4-Piperidin-1-yl-3-trifluoromethyl-phenylamine: Piperidine (1.7 mL, 17.2 mmol) and 2-fluoro-5-nitrobenzotrifluoride (3 g, 14.3 mmol, available Aldrich Chemical) were dissolved in DMF (25 mL) and heated to 110° C. in a sealed tube for 24 h. The reaction was then cooled to room temperature diluted with ethyl acetate (100 mL) and washed with water (2×150 mL), brine (50 mL), dried over N$_2$SO$_4$, and concentrated to give a yellow orange oil; Electrospray MS (MH$^+$), m/z 275. The oil was then hydrogenated over 10% Pd/C (300 mg) in ethanol (50 mL) at atmospheric pressure for 24 h. The suspension was then filtered though a cake of celite and concentrated to give the corresponding aniline (3.50 g, 100%) as a light yellow oil. This material was used in the next step without further purification.

Step b. α-Bromoacetyl bromide (11.6 μL, 0.13 mmol) was added to a dichloromethane solution (2 μL) containing 3-(3-chlorophenyl)-5-trifluoromethylaniline (40 mg, 0.13 mmol) and triethylamine (18 μL, 0.13 mmol) at room temperature. After stirring overnight, excess solvent was removed, DMF (2 mL) and the 4-piperidin-1-yl-3-trifluoromethylaniline obtained above were added, and the entire mixture was heated at 70° C. for 8 h. The resulting solution was directly injected on a preparative reverse phase HPLC column and fractions, which contained the desired product mass, were collected and concentrated. $^1$H NMR (CD$_3$OD) δ 8.00 (s, 1 H), 7.88 (s, 1 H), 7.52 (s, 1 H), 7.42 (d, J=8 Hz, 1 H), 7.26 (t, J=8 Hz, 1 H), 7.04 (t, J=2 Hz, 1 H), 6.89–6.98 (m, 3 H), 6.88 (dd, J=2 Hz, J=8 Hz, 1 H), 5.14 (s, 2 H), 4.00 (s, 2 H), 3.02 (m, 4 H), 1.77 (m, 4 H), 1.61 (m, 2 H); Electrospray MS (MH$^+$) m/z 586.

Example 137

Compound 137. Step a. Methyl 3-amino-5-trifluoromethylbenzozate (2.0 g, 9.13 mmol, obtained from the esterification of the commercially available 3-nitro-5-trifluoromethylbenzoic acid followed by reduction of the nitro group over Pd/C under atmospheric hydrogen) and 2,5-dimethoxytetrahydrofuran (5.91 g, 45.7 mmol) in acetic acid (15 mL) were heated at 60° C. for 1.5 hrs. After cooled to rt, the reaction mixture was diluted with ethyl acetate and washed with saturated $NaHCO_3$ and brine. The organic layer was dried with $Na_2SO_4$, filtered, and concentrated. The crude product was purified by flash chromatography on silica gel eluted with 4:1 to 3:1 hexanes/AcOEt. This product was then further purified by recrystallization from ether/hexanes to give pyrrole product (1.71 g, 69.6%). $^1$H ($CDCl_3$) δ 8.25 (s, 1H), 8.12 (s, 1H), 7.80 (s, 1H), 7.16 (d, J=6.0 Hz, 1H), 6.40 (d, J=6.0 Hz, 1H), 3.97 (s, 3H).

Step b. A portion of the pyrrole from Step a (0.766 g, 285 mmol) was treated with LAH (1 M solution in THF, 8.6 mL) in THF (15 mL) at 0° C. After standard work-up, the corresponding alcohol was obtained (0.707 g, 87.0%)

Step c. A sample of the alcohol form Step b (57 mg, 0.224 mmol) and 4-chloro-3-3trifluoromethylphenyl isocyanate (55 mg, 0.248 mmol) were stirred at rt in DCM. At the completion of the reaction, which typically takes overnight stirring, the reaction mixture was diluted with DCM and washed with $NaHCO_3$. The organic layer was dried over $MgSO_4$, filtered and concentrated. The crude product was purified by chromatography on Silica gel eluted with 4:1 hexanes/EtOAc to give the desired product (71 mg, 69.3%). $^1$H NMR (DMSO) δ 10.3 (s, 1H) 8.01 (s, 1+1H), 7.91 (s, 1H), 7.70 (d, J=7.0 Hz, 1H), 7.65 (s, 1H), 7.62 (d, J=7.0 Hz, 1H), 7.55 (s, 1H), 7.53 (s, 1H), 6.31 (d, J=6.0 Hz, 2H), 5.30 (d, J=6.0 Hz, 2H), 2.5 (s, 2H).

Example 138

Compound 138. Step a. A sample of the alcohol compound from Step b of Example 137 above was converted to the benzylamine in a three-step operation, activation of the alcohol to its mesylate, displacement of the mesylate by azide, and reduction of the azide to amine.

Step b. A sample of the amine from Step a above was treated with and 4-chloro-3-trifluoromethylphenyl isocyanate following the same conditions described to give the title compound. $^1$H NMR (DMSO) δ 9.20 (s, 1H), 8.05 (s, 1H), 7.83 (s, 1H), 7.81 (s, 1H), 7.62 (d, J=7.0 Hz, 1H), 7.55 (d, J=7.0 Hz, 1H), 7.50 (d, J=5.0 Hz, 2H), 7.50 (s, 1H), 7.00 (t, J=2.5 Hz, 1H), 6.30 (d, J=5.0 Hz, 2H), 4.40 (d, J=2.5 Hz, 2H).

Example 139

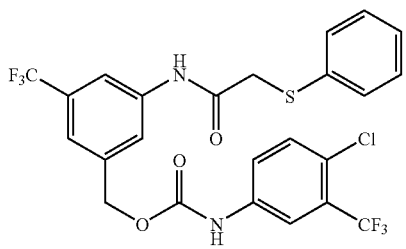

139

(4-Chloro-3-trifluoromethyl-phenyl)-carbamic acid 3-(2-phenylsulfanyl-acetylamino)-5-trifluoromethyl benzyl ester (139)

Step 1a. To a THF/ethanol(10:1) solution of 3-(2-Phenylsulfanyl-acetylamino)-5-trifluoromethyl-benzoic acid methyl ester (252 mg, 0.68 mmol) was added sodium borohydride (46 mg, 1.4 mmol), and the mixture was stirred at 65° C. for 2 hours. The reaction mixture was left overnight. The mixture was diluted with ethyl acetate, washed with 1 N HCl (2x) and brine. The organic layer was dried over $MgSO_4$, filtered and stripped. The crude product was purified by flash chromatography on silica gel eluted with hexane/ethyl acetate (4:1) to give 126 mg of N-(3-Hydroxymethyl-5-trifluoromethyl-phenyl)-2-phenylsulfanyl-acetamide in 54% yield.

Step 1b. To a $CH_2Cl_2$ solution of N-(3-Hydroxymethyl-5-trifluoromethyl-phenyl)-2-phenylsulfanyl-acetamide (126 mg, 0.37mmol) was added 1-Chloro-4-isocyanato-2-trifluoromethyl-benzene (86 mg, 0.38 mmol), and the mixture was stirred at room temperature for 2 hours. The organic solvent was removed under vacuum and the crude product was purified by flash chromatography on silica gel eluted with hexane/ethyl acetate (3:1) to give 170.9 mg of (4-Chloro-3-trifluoromethyl-phenyl)-carbamic acid 3-(2-phenylsulfanyl-acetylamino)-5-trifluoromethyl benzyl ester in 82% yield. $^1$H NMR ($CDCl_3$): δ 3.80(s, 3H), 5.19(s, 2H), 7.05(bs, 1H), 7.24–7.28(m, 2H), 7.31(d, J=10 Hz, 1H), 7.35(m, 5H), 7.42(d, J=9.6 Hz, 1H), 7.50(dd, J=9.6, 2 Hz, 1H), 7.54(m, 2H), 7.64(s, 1H), 7.74(d, J=2 Hz, 1H), 7.82(s, 1H), 8.75(s, 1H). MS SEI m/z relative intensity: M+H, 563.2(100)

Example 140

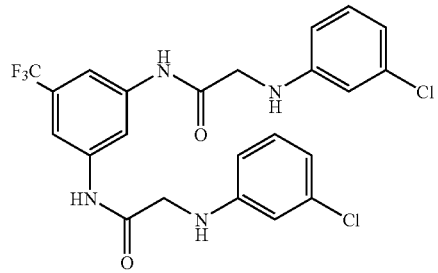

140

2-(3-Chloro-phenylamino)-N-{3-[2-(3-chloro-phenylamino)-acetylamino]-5-trifluoromethyl-phenyl}acetamide (140)

To a $CH_2Cl_2$ solution of 2-Bromo-N-[3-(2-bromo-acetylamino)-5-trifluoromethyl-phenyl]-acetamide (150 mg, 0.30 mmol) at room temperature was added 3-chloroaniline (100 μL), the mixture was stirred at room temperature for 1 hour. The mixture was diluted with ethyl acetate, washed with $NaHCO_3$ solution followed byl N HCl (2x) and brine. The organic layer was dried over $MgSO_4$, filtered and stripped and the crude product was purified by flash chromatography on silica gel eluted with hexane/ethyl acetate (2:1) to give 132 mg of the title compound in 92% yield. $^1$H NMR (400 MHz, $CDCl_3$): δ 3.87(s, 4H), 6.49(dd, J=2, 8.4 Hz, 2H), 6.63(s, 2H), 6.79(d, J=2, 8.4 Hz, 2H), 7.10(t, J=8.0 Hz, 2H), 7.46(s, 2H), 8.20(s, 1H), 8.77(s, 2H). MS SEI m/z relative intensity:M+H, 511.2(100).

Example 141

This example illustrates the levels of activity associated with representative compounds of the invention.

TABLE 1

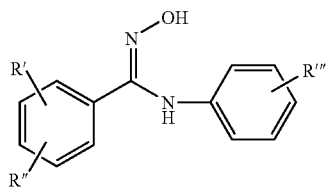

| R' | R'' | R''' | IC50 | B. su | S. au | E. c(tolC) |
|---|---|---|---|---|---|---|
| 3-CF$_3$ | 4-Cl | 3-Cl | +++ | +++ | +++ | +++ |
| 3-CF$_3$ | 4-F | H | ++ | ++ | + | +++ |
| 3-NO$_2$ | 4-Cl | H | ++ | + | + | + |
| 3-CF$_3$ | 4-Cl | H | +++ | ++ | +++ | +++ |
| 3-OCF$_3$ | H | 3-Cl | ++ | +++ | ++ | +++ |
| 3-Cl | 4-Cl | 3-F | ++ | ++ | ++ | +++ |
| 3-CF$_3$ | H | 3-F | ++ | ++ | ++ | +++ |
| 3-CF$_3$ | H | 3-Br | ++ | +++ | ++ | +++ |
| 3-CF$_3$ | H | 3-CN | + | + | + | ++ |
| 3-CF$_3$ | H | 3-OPh | + | +++ | +++ | +++ |
| 4-Cl | H | 3-Cl | + | ++ | ++ | +++ |
| 3-CF$_3$ | 5-CF$_3$ | H | + | ++ | ++ | +++ |

IC50: less than 10 μM,
+++; from 10 to 50 μM,
++; greater than 50 μM, +.
Bacterial MICs: less than 40 μM,
+++; from 40 to 125 μM,
++; greater than 125 μM, +.

Example 141

This example illustrates the levels of RNA polymerase inhibitory and antibacterial activity associate with representative compounds of the invention.

TABLE 2

| Compound | RNA-pol IC$_{50}$ (μM) S. aureus | MIC (μM) S. aureus | RNA-pol IC$_{50}$ (μM) E. coli | MIC (μM) E. coli (tolC) |
|---|---|---|---|---|
| 109 | + | +++ | ++ | +++ |
| 110 | + | ++ | + | + |
| 111 | | + | ++ | +++ |
| 112 | + | + | ++ | +++ |
| 113 | | +++ | ++ | +++ |
| 114 | + | +++ | +++ | +++ |
| 115 | + | +++ | + | +++ |
| 116 | + | +++ | +++ | +++ |
| 117 | +++ | +++ | | + |
| 118 | + | +++ | | +++ |
| 119 | | +++ | | +++ |
| 120 | ++ | +++ | + | +++ |
| 121 | + | +++ | | + |
| 122 | ++ | +++ | | + |
| 123 | +++ | +++ | | + |
| 124 | ++ | +++ | | + |
| 125 | ++ | +++ | | +++ |
| 126 | +++ | + | | +++ |
| 127 | ++ | + | | + |
| 128 | + | +++ | | +++ |
| 129 | + | +++ | | + |
| 130 | + | +++ | | + |
| 131 | +++ | +++ | | + |
| 132 | ++ | +++ | | +++ |
| 133 | ++ | +++ | | +++ |
| 134 | +++ | +++ | | + |
| 135 | ++ | +++ | | + |
| 136 | +++ | +++ | | + |
| 137 | ++ | +++ | | +++ |
| 138 | ++ | +++ | | +++ |

TABLE 2-continued

| Compound | RNA-pol IC$_{50}$ (μM) S. aureus | MIC (μM) S. aureus | RNA-pol IC$_{50}$ (μM) E. coli | MIC (μM) E. coli (tolC) |
|---|---|---|---|---|
| 139 | ++ | +++ | | +++ |
| 140 | | +++ | | + |

IC$_{50}$s: less than 10 μM, +++; from 10–50 μM, ++; greater than 50 μM, +
Bacterial MICs: less than 40 μM, +++; from 40 to 125 μM, ++; greater than 125 μM, +

All publications and patent applications cited in this specification are herein icorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

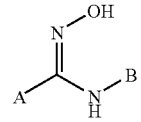

wherein A is a phenyl group substituted with from one to three substituents selected from the group consisting of (C$_1$–C$_4$)alkyl, (C$_1$–C$_4$)alkoxy, (C$_1$–C$_4$)haloalkyl, (C$_1$–C$_4$)haloalkoxy and —NR$^{16}$R$^{17}$, wherein R$^{16}$ and R$^{17}$ are independently selected from the group consisting of hydrogen, (C$_1$–C$_8$)alkyl and (C$_1$–C$_8$)heteroalkyl; and wherein B is substituted or unsubstituted phenyl.

2. A compound of claim 1, wherein B is a phenyl group substituted with from one to three substituents selected from the group consisting of (C$_1$–C$_4$)alkyl, (C$_1$–C$_4$)alkoxy, (C$_1$–C$_4$)heteroalkyl, (C$_1$–C$_4$)haloalkyl, (C$_1$–C$_4$)haloalkoxy, and halogen.

3. The compound of claim 2, wherein A is a phenyl group substituted with from one to three substituents selected from the group consisting of (C$_1$–C$_4$)alkyl, (C$_1$–C$_4$)haloalkyl and —NR$^{16}$R$^{17}$; wherein R$^{16}$ is hydrogen and R$^{17}$ is a (C$_1$–C$_4$) alkyl group optionally substituted with substituents selected from the group consisting of: =O, =NR', =N—OR', —NR'R'', —OR' and —SR'; and wherein R' and R'' are independently selected from the group consisting of hydrogen, unsubstituted (C$_1$–C$_8$) alkyl, heteroalkyl, unsubstituted aryl, aryl substituted with substituents selected from the group consisting of 1–3 halogens, unsubstituted alkyl, alkoxy, thioalkoxy and aryl(C$_1$–C$_4$)alkyl.

4. The compound of claim 3, wherein R' is hydrogen; and wherein R'' is an aryl group substituted with 1–3 halogens selected form the group consisting fluoro, chloro and bromo.

5. The compound of claim 2, wherein B is a phenyl group having 1–3 substituents selected from the group consisting of fluoro, chloro and bromo.

* * * * *